United States Patent
Sakai et al.

(10) Patent No.: US 7,038,028 B1
(45) Date of Patent: May 2, 2006

(54) GENE ENCODING PROMOTER DOMAIN OF TUMOR SUPPRESSOR GENE P51 AND USE THEREOF

(75) Inventors: Toshiyuki Sakai, Kyoto (JP); Shigehide Kagaya, Omiya (JP); Takamichi Sato, Yono (JP); Yoshikazu Sukenaga, Tokyo (JP); Hideji Fujii, Tokyo (JP)

(73) Assignees: Toshiyuki Sakai, Tokyo (JP); Oncolys Biopharma Inc., Tokyo (JP)

( * ) Notice: Subject to any disclaimer, the term of this patent is extended or adjusted under 35 U.S.C. 154(b) by 460 days.

(21) Appl. No.: 10/030,294

(22) PCT Filed: Jun. 28, 2000

(86) PCT No.: PCT/JP00/04261

§ 371 (c)(1),
(2), (4) Date: Dec. 27, 2001

(87) PCT Pub. No.: WO01/00818

PCT Pub. Date: Jan. 4, 2001

(30) Foreign Application Priority Data

Jun. 29, 1999 (JP) ................................. 11-183195

(51) Int. Cl.
*C12N 15/11* (2006.01)

(52) U.S. Cl. .................... 536/23.1; 435/325; 435/320.1

(58) Field of Classification Search ................ 536/24.1; 435/325, 69.1
See application file for complete search history.

(56) References Cited

FOREIGN PATENT DOCUMENTS

| WO | 99/50412 | 10/1999 |
|----|----------|---------|
| WO | 99/61610 | 12/1999 |

OTHER PUBLICATIONS

Darnell et al., (1990, Molecular Cell Biology, 2nd Edition, pp. 344-345 only).*
GenBank Acc. No. AQ168656 (Oct. 16, 1998).*
Yang et al., (1998, Molecular Cell, vol. 2, pp. 305-316).*
GenBank Acc. No. AF124528 (Jan. 4, 2001).*
Voet et al., (1990, Biochemistry, John Wiley & Sons, p. 865).*
Motonobu Osada et al., "Cloning and functional analysis of human p51, which structurally and functionally resembles p53", Nature Medicine (1998), vol. 4, No. 7, p. 839-843.
Martin Augustin et al., "Cloning and chromosomal mapping of the human p53-related Ket gene to Chromosome 3q27 and its murine homolog Ket to mouse Chromosome 16", Mammalian Genome (1998), vol. 9, No. 11, p. 899-902.
Hartwig Schmale et al., "A novel protein with strong homology to the tumor suppressor p53", Oncogene (1997), vol. 15, No. 11, p. 1363-1367.
Copy of the International Search dated Sep. 26, 2000.

* cited by examiner

*Primary Examiner*—Misook Yu
(74) *Attorney, Agent, or Firm*—Nields & Lemack

(57) ABSTRACT

In accordance with the present invention, there are provided a gene encoding the promoter region of a protein p51 which is capable of inducing cell death, and a gene encoding the 5'-untranslated region of p51. These genes are useful in diagnosing and treating diseases including cancer caused by abnormal regulation of cell propagation. Furthermore, in accordance with the present invention, there are provided the antisense DNAs and the antisense RNAs of these genes, nucleic acid probes comprising parts or all of these genes, methods of detecting the above genes of the present invention or analogous genes using the nucleic acid probes, transformants in which the above gene of the present invention has been introduced, and methods of screening drugs using them. These genes are also useful in diagnosing and treating diseases including cancer, etc.

3 Claims, 3 Drawing Sheets

SEQUENCE LISTING

```
<160> NUMBER OF SEQ ID NOS: 23

<210> SEQ ID NO 1
<211> LENGTH: 2464
<212> TYPE: DNA
<213> ORGANISM: Homo sapiens
<220> FEATURE:
<221> NAME/KEY: CDS
<222> LOCATION: (1)...(2463)

<400> SEQUENCE: 1 atg aca tcg ccc cag cta gag tgg act ctg cag acc ctt ctg gag cag      48
```

-continued

```
Met Thr Ser Pro Gln Leu Glu Trp Thr Leu Gln Thr Leu Leu Glu Gln
 1               5                  10                  15 ctg aac gag gat gaa tta aag agt ttc aaa tcc ctt tta tgg gct ttt       96
Leu Asn Glu Asp Glu Leu Lys Ser Phe Lys Ser Leu Leu Trp Ala Phe
                 20                  25                  30 ccc ctc gaa gac gtg cta cag aag acc cca tgg tct gag gtg gaa gag      144
Pro Leu Glu Asp Val Leu Gln Lys Thr Pro Trp Ser Glu Val Glu Glu
             35                  40                  45 gct gat ggc aag aaa ctg gca gaa att ctg gtc aac acc tcc tca gaa      192
Ala Asp Gly Lys Lys Leu Ala Glu Ile Leu Val Asn Thr Ser Ser Glu
         50                  55                  60 aat tgg ata agg aat gcg act gtg aac atc ttg gaa gag atg aat ctc      240
Asn Trp Ile Arg Asn Ala Thr Val Asn Ile Leu Glu Glu Met Asn Leu
 65                  70                  75                  80 acg gaa ttg tgt aag atg gca aag gct gag atg atg gag gac gga cag      288
Thr Glu Leu Cys Lys Met Ala Lys Ala Glu Met Met Glu Asp Gly Gln
                 85                  90                  95 gtg caa gaa ata gat aat cct gag ctg gga gat gca gaa gaa gac tcg      336
Val Gln Glu Ile Asp Asn Pro Glu Leu Gly Asp Ala Glu Glu Asp Ser
            100                 105                 110 gag tta gca aag cca ggt gaa aag gaa gga tgg aga aat tca atg gag      384
Glu Leu Ala Lys Pro Gly Glu Lys Glu Gly Trp Arg Asn Ser Met Glu
        115                 120                 125 aaa caa tct ttg gtc tgg aag aac acc ttt tgg caa gga gac att gac      432
Lys Gln Ser Leu Val Trp Lys Asn Thr Phe Trp Gln Gly Asp Ile Asp
130                 135                 140 aat ttc cat gac gac gtc act ctg aga aac caa cgg ttc att cca ttc      480
Asn Phe His Asp Asp Val Thr Leu Arg Asn Gln Arg Phe Ile Pro Phe
145                 150                 155                 160 ttg aat ccc aga aca ccc agg aag cta aca cct tac acg gtg gtg ctg      528
Leu Asn Pro Arg Thr Pro Arg Lys Leu Thr Pro Tyr Thr Val Val Leu
                165                 170                 175 cac ggc ccc gca ggc gtg ggg aaa acc acg ctg gcc aaa aag tgt atg      576
His Gly Pro Ala Gly Val Gly Lys Thr Thr Leu Ala Lys Lys Cys Met
            180                 185                 190 ctg gac tgg aca gac tgc aac ctc agc ccg acg ctc aga tac gcg ttc      624
Leu Asp Trp Thr Asp Cys Asn Leu Ser Pro Thr Leu Arg Tyr Ala Phe
        195                 200                 205 tac ctc agc tgc aag gag ctc agc cgc atg ggc ccc tgc agt ttt gca      672
Tyr Leu Ser Cys Lys Glu Leu Ser Arg Met Gly Pro Cys Ser Phe Ala
    210                 215                 220 gag ctg atc tcc aaa gac tgg cct gaa ttg cag gat gac att cca agc      720
Glu Leu Ile Ser Lys Asp Trp Pro Glu Leu Gln Asp Asp Ile Pro Ser
225                 230                 235                 240 atc cta gcc caa gca cag aga atc ctg ttc gtg gtc gat ggc ctt gat      768
Ile Leu Ala Gln Ala Gln Arg Ile Leu Phe Val Val Asp Gly Leu Asp
                245                 250                 255 gag ctg aaa gtc cca cct ggg gcg ctg atc cag gac atc tgc ggg gac      816
Glu Leu Lys Val Pro Pro Gly Ala Leu Ile Gln Asp Ile Cys Gly Asp
            260                 265                 270 tgg gag aag aag aag ccg gtg ccc gtc ctc ctg ggg agt ttg ctg aag      864
Trp Glu Lys Lys Lys Pro Val Pro Val Leu Leu Gly Ser Leu Leu Lys
        275                 280                 285 agg aag atg tta ccc agg gca gcc ttg ctg gtc acc acg cgg ccc agg      912
Arg Lys Met Leu Pro Arg Ala Ala Leu Leu Val Thr Thr Arg Pro Arg
    290                 295                 300 gca ctg agg gac ctc cag ctc ctg gcg cag cag ccg atc tac ata agg      960
Ala Leu Arg Asp Leu Gln Leu Leu Ala Gln Gln Pro Ile Tyr Ile Arg
305                 310                 315                 320
```

```
gtg gag ggc ttc ctg gag gag gac agg agg gcc tat ttc ctg aga cac    1008
Val Glu Gly Phe Leu Glu Glu Asp Arg Arg Ala Tyr Phe Leu Arg His
            325             330             335 ttt gga gac gag gac caa gcc atg cgt gcc ttt gag cta atg agg agc    1056
Phe Gly Asp Glu Asp Gln Ala Met Arg Ala Phe Glu Leu Met Arg Ser
            340             345             350 aac gcg gcc ctg ttc cag ctg ggc tcg gcc ccc gcg gtg tgc tgg att    1104
Asn Ala Ala Leu Phe Gln Leu Gly Ser Ala Pro Ala Val Cys Trp Ile
            355             360             365 gtg tgc acg act ctg aag ctg cag atg gag aag ggg gag gac ccg ccg    1152
Val Cys Thr Thr Leu Lys Leu Gln Met Glu Lys Gly Glu Asp Pro Pro
    370             375             380 gtt ccc gca ggg cgc aca gct gcg ggg cgc gct gcg gac gct gag cct    1200
Val Pro Ala Gly Arg Thr Ala Ala Gly Arg Ala Ala Asp Ala Glu Pro
385             390             395             400 cct ggc cgc gca ggg ctg tgg gcg cag atg tcc gtg ttc cac cga gag    1248
Pro Gly Arg Ala Gly Leu Trp Ala Gln Met Ser Val Phe His Arg Glu
            405             410             415 gac ctg gaa agg ctc ggg gtg cag gag tcc gac ctc cgt ctg ttc ctg    1296
Asp Leu Glu Arg Leu Gly Val Gln Glu Ser Asp Leu Arg Leu Phe Leu
            420             425             430 gac gga gac atc ctc cgc cag gac aga gtc tcc aaa ggc tgc tac tcc    1344
Asp Gly Asp Ile Leu Arg Gln Asp Arg Val Ser Lys Gly Cys Tyr Ser
            435             440             445 ttc atc cac ctc agc ttc cag cag ttt ctc act gcc ctg ttc tac gcc    1392
Phe Ile His Leu Ser Phe Gln Gln Phe Leu Thr Ala Leu Phe Tyr Ala
    450             455             460 ctg gag aag gag gag gag gag gac agg gac ggc cac gcc tgg gac att    1440
Leu Glu Lys Glu Glu Glu Glu Asp Arg Asp Gly His Ala Trp Asp Ile
465             470             475             480 ggg gac gta cag aag ctg ctt tcc gga gaa gaa aga ctc aag aac ccc    1488
Gly Asp Val Gln Lys Leu Leu Ser Gly Glu Glu Arg Leu Lys Asn Pro
            485             490             495 gac ctg att caa gta gga cac ttc tta ttc ggc ctc gct aac gag aag    1536
Asp Leu Ile Gln Val Gly His Phe Leu Phe Gly Leu Ala Asn Glu Lys
            500             505             510 aga gcc aag gag ttg gag gcc act ttt ggc tgc cgg atg tca ccg gac    1584
Arg Ala Lys Glu Leu Glu Ala Thr Phe Gly Cys Arg Met Ser Pro Asp
            515             520             525 atc aaa cag gaa ttg ctg caa tgc aaa gca cat ctt cat gca aat aag    1632
Ile Lys Gln Glu Leu Leu Gln Cys Lys Ala His Leu His Ala Asn Lys
            530             535             540 ccc tta tcc gtg acc gac ctg aag gag gtc ttg ggc tgc ctg tat gag    1680
Pro Leu Ser Val Thr Asp Leu Lys Glu Val Leu Gly Cys Leu Tyr Glu
545             550             555             560 tct cag gag gag gag ctg gcg aag gtg gtg gtg gcc ccg ttc aag gaa    1728
Ser Gln Glu Glu Glu Leu Ala Lys Val Val Val Ala Pro Phe Lys Glu
            565             570             575 att tct att cac ctg aca aat act tct gaa gtg atg cat tgt tcc ttc    1776
Ile Ser Ile His Leu Thr Asn Thr Ser Glu Val Met His Cys Ser Phe
            580             585             590 agc ctg aag cat tgt caa gac ttg cag aaa ctc tca ctg cag gta gca    1824
Ser Leu Lys His Cys Gln Asp Leu Gln Lys Leu Ser Leu Gln Val Ala
            595             600             605 aag ggg gtg ttc ctg gag aat tac atg gat ttt gaa ctg gac att gaa    1872
Lys Gly Val Phe Leu Glu Asn Tyr Met Asp Phe Glu Leu Asp Ile Glu
            610             615             620 ttt gaa agc tca aac agc aac ctc aag ttt ctg gaa gtg aaa caa agc    1920
Phe Glu Ser Ser Asn Ser Asn Leu Lys Phe Leu Glu Val Lys Gln Ser
625             630             635             640
```

-continued

```
ttc ctg agt gac tct tct gtg cgg att ctt tgt gac cac gta acc cgt    1968
Phe Leu Ser Asp Ser Ser Val Arg Ile Leu Cys Asp His Val Thr Arg
            645                 650                 655 agc acc tgt cat ctg cag aaa gtg gag att aaa aac gtc acc cct gac    2016
Ser Thr Cys His Leu Gln Lys Val Glu Ile Lys Asn Val Thr Pro Asp
        660                 665                 670 acc gcg tac cgg gac ttc tgt ctt gct ttc att ggg aag aag acc ctc    2064
Thr Ala Tyr Arg Asp Phe Cys Leu Ala Phe Ile Gly Lys Lys Thr Leu
    675                 680                 685 acg cac ctg acc ctg gca ggg cac atc gag tgg gaa cgc acg atg atg    2112
Thr His Leu Thr Leu Ala Gly His Ile Glu Trp Glu Arg Thr Met Met
690                 695                 700 ctg atg ctg tgt gac ctg ctc aga aat cat aaa tgc aac ctg cag tac    2160
Leu Met Leu Cys Asp Leu Leu Arg Asn His Lys Cys Asn Leu Gln Tyr
705                 710                 715                 720 ctg agg ttg gga ggt cac tgt gcc acc ccg gag cag tgg gct gaa ttc    2208
Leu Arg Leu Gly Gly His Cys Ala Thr Pro Glu Gln Trp Ala Glu Phe
                725                 730                 735 ttc tat gtc ctc aaa gcc aac cag tcc ctg aag cac ctg cgt ctc tca    2256
Phe Tyr Val Leu Lys Ala Asn Gln Ser Leu Lys His Leu Arg Leu Ser
            740                 745                 750 gcc aat gtg ctc ctg gat gag ggt gcc atg ttg ctg tac aag acc atg    2304
Ala Asn Val Leu Leu Asp Glu Gly Ala Met Leu Leu Tyr Lys Thr Met
        755                 760                 765 aca cgc cca aaa cac ttc ctg cag atg ttg tcg ttg gaa aac tgt cgt    2352
Thr Arg Pro Lys His Phe Leu Gln Met Leu Ser Leu Glu Asn Cys Arg
    770                 775                 780 ctt aca gaa gcc agt tgc aag gac ctt gct gct gtc ttg gtt gtc agc    2400
Leu Thr Glu Ala Ser Cys Lys Asp Leu Ala Ala Val Leu Val Val Ser
785                 790                 795                 800 aag aag ctg aca cac ctg tgc ttg gcc aag aac ccc att ggg gat aca    2448
Lys Lys Leu Thr His Leu Cys Leu Ala Lys Asn Pro Ile Gly Asp Thr
                805                 810                 815 ggg gtg aag ttt ctg t                                              2464
Gly Val Lys Phe Leu
                820
```

<210> SEQ ID NO 2
<211> LENGTH: 821
<212> TYPE: PRT
<213> ORGANISM: Homo sapiens

<400> SEQUENCE: 2

```
Met Thr Ser Pro Gln Leu Glu Trp Thr Leu Gln Thr Leu Leu Glu Gln
  1               5                  10                  15

Leu Asn Glu Asp Glu Leu Lys Ser Phe Lys Ser Leu Leu Trp Ala Phe
                 20                  25                  30

Pro Leu Glu Asp Val Leu Gln Lys Thr Pro Trp Ser Glu Val Glu Glu
             35                  40                  45

Ala Asp Gly Lys Lys Leu Ala Glu Ile Leu Val Asn Thr Ser Ser Glu
         50                  55                  60

Asn Trp Ile Arg Asn Ala Thr Val Asn Ile Leu Glu Glu Met Asn Leu
 65                  70                  75                  80

Thr Glu Leu Cys Lys Met Ala Lys Ala Glu Met Met Glu Asp Gly Gln
                 85                  90                  95

Val Gln Glu Ile Asp Asn Pro Glu Leu Gly Asp Ala Glu Glu Asp Ser
            100                 105                 110

Glu Leu Ala Lys Pro Gly Glu Lys Glu Gly Trp Arg Asn Ser Met Glu
```

-continued

```
            115                 120                 125
Lys Gln Ser Leu Val Trp Lys Asn Thr Phe Trp Gln Gly Asp Ile Asp
            130                 135                 140
Asn Phe His Asp Asp Val Thr Leu Arg Asn Gln Arg Phe Ile Pro Phe
145                 150                 155                 160
Leu Asn Pro Arg Thr Pro Arg Lys Leu Thr Pro Tyr Thr Val Val Leu
                165                 170                 175
His Gly Pro Ala Gly Val Gly Lys Thr Thr Leu Ala Lys Lys Cys Met
                180                 185                 190
Leu Asp Trp Thr Asp Cys Asn Leu Ser Pro Thr Leu Arg Tyr Ala Phe
            195                 200                 205
Tyr Leu Ser Cys Lys Glu Leu Ser Arg Met Gly Pro Cys Ser Phe Ala
            210                 215                 220
Glu Leu Ile Ser Lys Asp Trp Pro Glu Leu Gln Asp Asp Ile Pro Ser
225                 230                 235                 240
Ile Leu Ala Gln Ala Gln Arg Ile Leu Phe Val Val Asp Gly Leu Asp
                245                 250                 255
Glu Leu Lys Val Pro Pro Gly Ala Leu Ile Gln Asp Ile Cys Gly Asp
                260                 265                 270
Trp Glu Lys Lys Pro Val Pro Val Leu Leu Gly Ser Leu Leu Lys
                275                 280                 285
Arg Lys Met Leu Pro Arg Ala Ala Leu Leu Val Thr Thr Arg Pro Arg
            290                 295                 300
Ala Leu Arg Asp Leu Gln Leu Ala Gln Gln Pro Ile Tyr Ile Arg
305                 310                 315                 320
Val Glu Gly Phe Leu Glu Glu Asp Arg Arg Ala Tyr Phe Leu Arg His
                325                 330                 335
Phe Gly Asp Glu Asp Gln Ala Met Arg Ala Phe Glu Leu Met Arg Ser
                340                 345                 350
Asn Ala Ala Leu Phe Gln Leu Gly Ser Ala Pro Ala Val Cys Trp Ile
            355                 360                 365
Val Cys Thr Thr Leu Lys Leu Gln Met Glu Lys Gly Glu Asp Pro Pro
            370                 375                 380
Val Pro Ala Gly Arg Thr Ala Ala Gly Arg Ala Ala Asp Ala Glu Pro
385                 390                 395                 400
Pro Gly Arg Ala Gly Leu Trp Ala Gln Met Ser Val Phe His Arg Glu
                405                 410                 415
Asp Leu Glu Arg Leu Gly Val Gln Glu Ser Asp Leu Arg Leu Phe Leu
                420                 425                 430
Asp Gly Asp Ile Leu Arg Gln Asp Arg Val Ser Lys Gly Cys Tyr Ser
                435                 440                 445
Phe Ile His Leu Ser Phe Gln Gln Phe Leu Thr Ala Leu Phe Tyr Ala
            450                 455                 460
Leu Glu Lys Glu Glu Glu Asp Arg Asp Gly His Ala Trp Asp Ile
465                 470                 475                 480
Gly Asp Val Gln Lys Leu Leu Ser Gly Glu Glu Arg Leu Lys Asn Pro
                485                 490                 495
Asp Leu Ile Gln Val Gly His Phe Leu Phe Gly Leu Ala Asn Glu Lys
                500                 505                 510
Arg Ala Lys Glu Leu Glu Ala Thr Phe Gly Cys Arg Met Ser Pro Asp
            515                 520                 525
Ile Lys Gln Glu Leu Leu Gln Cys Lys Ala His Leu His Ala Asn Lys
            530                 535                 540
```

```
Pro Leu Ser Val Thr Asp Leu Lys Glu Val Leu Gly Cys Leu Tyr Glu
545                 550                 555                 560

Ser Gln Glu Glu Glu Leu Ala Lys Val Val Ala Pro Phe Lys Glu
            565                 570                 575

Ile Ser Ile His Leu Thr Asn Thr Ser Glu Val Met His Cys Ser Phe
                580                 585                 590

Ser Leu Lys His Cys Gln Asp Leu Gln Lys Leu Ser Leu Gln Val Ala
            595                 600                 605

Lys Gly Val Phe Leu Glu Asn Tyr Met Asp Phe Glu Leu Asp Ile Glu
        610                 615                 620

Phe Glu Ser Ser Asn Ser Asn Leu Lys Phe Leu Glu Val Lys Gln Ser
625                 630                 635                 640

Phe Leu Ser Asp Ser Ser Val Arg Ile Leu Cys Asp His Val Thr Arg
                645                 650                 655

Ser Thr Cys His Leu Gln Lys Val Glu Ile Lys Asn Val Thr Pro Asp
            660                 665                 670

Thr Ala Tyr Arg Asp Phe Cys Leu Ala Phe Ile Gly Lys Lys Thr Leu
        675                 680                 685

Thr His Leu Thr Leu Ala Gly His Ile Glu Trp Glu Arg Thr Met Met
690                 695                 700

Leu Met Leu Cys Asp Leu Leu Arg Asn His Lys Cys Asn Leu Gln Tyr
705                 710                 715                 720

Leu Arg Leu Gly Gly His Cys Ala Thr Pro Glu Gln Trp Ala Glu Phe
                725                 730                 735

Phe Tyr Val Leu Lys Ala Asn Gln Ser Leu Lys His Leu Arg Leu Ser
            740                 745                 750

Ala Asn Val Leu Leu Asp Glu Gly Ala Met Leu Leu Tyr Lys Thr Met
        755                 760                 765

Thr Arg Pro Lys His Phe Leu Gln Met Leu Ser Leu Glu Asn Cys Arg
770                 775                 780

Leu Thr Glu Ala Ser Cys Lys Asp Leu Ala Ala Val Leu Val Val Ser
785                 790                 795                 800

Lys Lys Leu Thr His Leu Cys Leu Ala Lys Asn Pro Ile Gly Asp Thr
                805                 810                 815

Gly Val Lys Phe Leu
            820

<210> SEQ ID NO 3
<211> LENGTH: 1895
<212> TYPE: DNA
<213> ORGANISM: Homo sapiens
<220> FEATURE:
<221> NAME/KEY: CDS
<222> LOCATION: (1)...(1893)

<400> SEQUENCE: 3 atg gca gaa tcg gat tct act gac ttt gac ctg ctg tgg tat cta gag     48
Met Ala Glu Ser Asp Ser Thr Asp Phe Asp Leu Leu Trp Tyr Leu Glu
1               5                   10                  15 aat ctc agt gac aag gaa ttt cag agt ttt aag aag tat ctg gca cgc     96
Asn Leu Ser Asp Lys Glu Phe Gln Ser Phe Lys Lys Tyr Leu Ala Arg
            20                  25                  30 aag att ctt gat ttc aaa ctg cca cag ttt cca ctg ata cag atg aca    144
Lys Ile Leu Asp Phe Lys Leu Pro Gln Phe Pro Leu Ile Gln Met Thr
        35                  40                  45 aaa gaa gaa ctg gct aac gtg ttg cca atc tct tat gag gga cag tat    192
```

```
                Lys Glu Glu Leu Ala Asn Val Leu Pro Ile Ser Tyr Glu Gly Gln Tyr
                    50                  55                  60 ata tgg aat atg ctc ttc agc ata ttt tca atg atg cgt aag gaa gat            240
Ile Trp Asn Met Leu Phe Ser Ile Phe Ser Met Met Arg Lys Glu Asp
 65                  70                  75                  80 ctt tgt agg aag atc att ggc aga cga aac cat gtg ttc tac ata ctt            288
Leu Cys Arg Lys Ile Ile Gly Arg Arg Asn His Val Phe Tyr Ile Leu
                 85                  90                  95 caa tta gcc tat gat tct acc agc tat tat tca gca aac aat ctc aat            336
Gln Leu Ala Tyr Asp Ser Thr Ser Tyr Tyr Ser Ala Asn Asn Leu Asn
                100                 105                 110 gtg ttc ctg atg gga gag aga gca tct gga aaa act att gtt ata aat            384
Val Phe Leu Met Gly Glu Arg Ala Ser Gly Lys Thr Ile Val Ile Asn
            115                 120                 125 ctg gct gtg ttg agg tgg atc aag ggt gag atg tgg cag aac atg atc            432
Leu Ala Val Leu Arg Trp Ile Lys Gly Glu Met Trp Gln Asn Met Ile
    130                 135                 140 tcg tac gtc gtt cac ctc act gct cac gaa ata aac cag atg acc aac            480
Ser Tyr Val Val His Leu Thr Ala His Glu Ile Asn Gln Met Thr Asn
145                 150                 155                 160 agc agc ttg gct gag cta atc gcc aag gac tgg cct gac ggc cag gct            528
Ser Ser Leu Ala Glu Leu Ile Ala Lys Asp Trp Pro Asp Gly Gln Ala
                165                 170                 175 ccc att gca gac atc ctg tct gat ccc aag aaa ctc ctt ttc atc ctc            576
Pro Ile Ala Asp Ile Leu Ser Asp Pro Lys Lys Leu Leu Phe Ile Leu
                180                 185                 190 gag gac ttg gac aac ata aga ttc gag tta aat gtc aat gaa agt gct            624
Glu Asp Leu Asp Asn Ile Arg Phe Glu Leu Asn Val Asn Glu Ser Ala
            195                 200                 205 ttg tgt agt aac agc acc cag aaa gtt ccc att cca gtt ctc ctg gtc            672
Leu Cys Ser Asn Ser Thr Gln Lys Val Pro Ile Pro Val Leu Leu Val
    210                 215                 220 agt ttg ctg aag aga aaa atg gct cca ggc tgc tgg ttc ctc atc tcc            720
Ser Leu Leu Lys Arg Lys Met Ala Pro Gly Cys Trp Phe Leu Ile Ser
225                 230                 235                 240 tca agg ccc aca cgt ggg aat aat gta aaa acg ttc ttg aaa gag gta            768
Ser Arg Pro Thr Arg Gly Asn Asn Val Lys Thr Phe Leu Lys Glu Val
                245                 250                 255 gat tgc tgc acg acc ttg cag ctg tcg aat ggg aag agg gag ata tat            816
Asp Cys Cys Thr Thr Leu Gln Leu Ser Asn Gly Lys Arg Glu Ile Tyr
                260                 265                 270 ttt aac tct ttc ttt aaa gac cgc cag agg gcg tcg gca gcc ctc cag            864
Phe Asn Ser Phe Phe Lys Asp Arg Gln Arg Ala Ser Ala Ala Leu Gln
            275                 280                 285 ctt gta cat gag gat gaa ata ctc gtg ggt ctg tgc cga gtc gcc atc            912
Leu Val His Glu Asp Glu Ile Leu Val Gly Leu Cys Arg Val Ala Ile
    290                 295                 300 tta tgc tgg atc acg tgt act gtc ctg aag cgg cag atg gac aag ggg            960
Leu Cys Trp Ile Thr Cys Thr Val Leu Lys Arg Gln Met Asp Lys Gly
305                 310                 315                 320 cgt gac ttc cag ctc tgc tgc caa aca ccc act gat cta cat gcc cac           1008
Arg Asp Phe Gln Leu Cys Cys Gln Thr Pro Thr Asp Leu His Ala His
                325                 330                 335 ttt ctt gct gat gcg ttg aca tca gag gct gga ctt act gcc aat cag           1056
Phe Leu Ala Asp Ala Leu Thr Ser Glu Ala Gly Leu Thr Ala Asn Gln
                340                 345                 350 tat cac cta ggt ctc cta aaa cgt ctg tgt ttg ctg gct gca gga gga           1104
Tyr His Leu Gly Leu Leu Lys Arg Leu Cys Leu Leu Ala Ala Gly Gly
            355                 360                 365
```

| | | | |
|---|---|---|---|
| ctg ttt ctg agc acc ctg aat ttc agt ggt gaa gac ctc aga tgt gtt | | | 1152 |
| Leu Phe Leu Ser Thr Leu Asn Phe Ser Gly Glu Asp Leu Arg Cys Val | | | |
| 370 | 375 | 380 | |
| ggg ttt act gag gct gat gtc tct gtg ttg cag gcc gcg aat att ctt | | | 1200 |
| Gly Phe Thr Glu Ala Asp Val Ser Val Leu Gln Ala Ala Asn Ile Leu | | | |
| 385 | 390 | 395 | 400 |
| ttg ccg agc aac act cat aaa gac cgt tac aag ttc ata cac ttg aac | | | 1248 |
| Leu Pro Ser Asn Thr His Lys Asp Arg Tyr Lys Phe Ile His Leu Asn | | | |
| | 405 | 410 | 415 |
| gtc cag gag ttt tgt aca gcc att gca ttt ctg atg gca gta ccc aac | | | 1296 |
| Val Gln Glu Phe Cys Thr Ala Ile Ala Phe Leu Met Ala Val Pro Asn | | | |
| | 420 | 425 | 430 |
| tat ctg atc ccc tca ggc agc aga gag tat aaa gag aag aga gaa caa | | | 1344 |
| Tyr Leu Ile Pro Ser Gly Ser Arg Glu Tyr Lys Glu Lys Arg Glu Gln | | | |
| | 435 | 440 | 445 |
| tac tct gac ttt aat caa gtg ttc act ttc att ttt ggt ctt cta aat | | | 1392 |
| Tyr Ser Asp Phe Asn Gln Val Phe Thr Phe Ile Phe Gly Leu Leu Asn | | | |
| 450 | 455 | 460 | |
| gca aac agg aga aag att ctt gag aca tcc ttt gga tac cag cta ccg | | | 1440 |
| Ala Asn Arg Arg Lys Ile Leu Glu Thr Ser Phe Gly Tyr Gln Leu Pro | | | |
| 465 | 470 | 475 | 480 |
| atg gta gac agc ttc aag tgg tac tcg gtg gga tac atg aaa cat ttg | | | 1488 |
| Met Val Asp Ser Phe Lys Trp Tyr Ser Val Gly Tyr Met Lys His Leu | | | |
| | 485 | 490 | 495 |
| gac cgt gac ccg gaa aag ttg acg cac cat atg cct ttg ttt tac tgt | | | 1536 |
| Asp Arg Asp Pro Glu Lys Leu Thr His His Met Pro Leu Phe Tyr Cys | | | |
| | 500 | 505 | 510 |
| ctc tat gag aat cgg gaa gaa gaa ttt gtg aag acg att gtg gat gct | | | 1584 |
| Leu Tyr Glu Asn Arg Glu Glu Glu Phe Val Lys Thr Ile Val Asp Ala | | | |
| | 515 | 520 | 525 |
| ctc atg gag gtt aca gtt tac ctt caa tca gac aag gat atg atg gtc | | | 1632 |
| Leu Met Glu Val Thr Val Tyr Leu Gln Ser Asp Lys Asp Met Met Val | | | |
| 530 | 535 | 540 | |
| tca tta tac tgt ctg gat tac tgc tgt cac ctg agg aca ctt aag ttg | | | 1680 |
| Ser Leu Tyr Cys Leu Asp Tyr Cys Cys His Leu Arg Thr Leu Lys Leu | | | |
| 545 | 550 | 555 | 560 |
| agt gtt cag cgc atc ttt caa aac aaa gag cca ctt ata agg cca act | | | 1728 |
| Ser Val Gln Arg Ile Phe Gln Asn Lys Glu Pro Leu Ile Arg Pro Thr | | | |
| | 565 | 570 | 575 |
| gct agt caa atg aag agc ctt gtc tac tgg aga gag atc tgc tct ctt | | | 1776 |
| Ala Ser Gln Met Lys Ser Leu Val Tyr Trp Arg Glu Ile Cys Ser Leu | | | |
| | 580 | 585 | 590 |
| ttt tat aca atg gag agc ctc cgg gag ctg cat atc ttt gac aat gac | | | 1824 |
| Phe Tyr Thr Met Glu Ser Leu Arg Glu Leu His Ile Phe Asp Asn Asp | | | |
| | 595 | 600 | 605 |
| ctt aat ggt att tca gaa agg att ctg tct aaa gcc ctg gag cat tct | | | 1872 |
| Leu Asn Gly Ile Ser Glu Arg Ile Leu Ser Lys Ala Leu Glu His Ser | | | |
| 610 | 615 | 620 | |
| agc tgt aaa ctt cgc aca ctc aa | | | 1895 |
| Ser Cys Lys Leu Arg Thr Leu | | | |
| 625 | 630 | | |

<210> SEQ ID NO 4
<211> LENGTH: 631
<212> TYPE: PRT
<213> ORGANISM: Homo sapiens

<400> SEQUENCE: 4

Met Ala Glu Ser Asp Ser Thr Asp Phe Asp Leu Leu Trp Tyr Leu Glu
1               5                   10                  15

-continued

```
Asn Leu Ser Asp Lys Glu Phe Gln Ser Phe Lys Lys Tyr Leu Ala Arg
             20                  25                  30

Lys Ile Leu Asp Phe Lys Leu Pro Gln Phe Pro Leu Ile Gln Met Thr
             35                  40                  45

Lys Glu Glu Leu Ala Asn Val Leu Pro Ile Ser Tyr Glu Gly Gln Tyr
 50                  55                  60

Ile Trp Asn Met Leu Phe Ser Ile Phe Ser Met Met Arg Lys Glu Asp
 65                  70                  75                  80

Leu Cys Arg Lys Ile Ile Gly Arg Arg Asn His Val Phe Tyr Ile Leu
             85                  90                  95

Gln Leu Ala Tyr Asp Ser Thr Ser Tyr Tyr Ser Ala Asn Asn Leu Asn
            100                 105                 110

Val Phe Leu Met Gly Glu Arg Ala Ser Gly Lys Thr Ile Val Ile Asn
            115                 120                 125

Leu Ala Val Leu Arg Trp Ile Lys Gly Glu Met Trp Gln Asn Met Ile
130                 135                 140

Ser Tyr Val Val His Leu Thr Ala His Glu Ile Asn Gln Met Thr Asn
145                 150                 155                 160

Ser Ser Leu Ala Glu Leu Ile Ala Lys Asp Trp Pro Asp Gly Gln Ala
            165                 170                 175

Pro Ile Ala Asp Ile Leu Ser Asp Pro Lys Lys Leu Leu Phe Ile Leu
            180                 185                 190

Glu Asp Leu Asp Asn Ile Arg Phe Glu Leu Asn Val Asn Glu Ser Ala
            195                 200                 205

Leu Cys Ser Asn Ser Thr Gln Lys Val Pro Ile Pro Val Leu Leu Val
            210                 215                 220

Ser Leu Leu Lys Arg Lys Met Ala Pro Gly Cys Trp Phe Leu Ile Ser
225                 230                 235                 240

Ser Arg Pro Thr Arg Gly Asn Asn Val Lys Thr Phe Leu Lys Glu Val
            245                 250                 255

Asp Cys Cys Thr Thr Leu Gln Leu Ser Asn Gly Lys Arg Glu Ile Tyr
            260                 265                 270

Phe Asn Ser Phe Lys Asp Arg Gln Arg Ala Ser Ala Ala Leu Gln
            275                 280                 285

Leu Val His Glu Asp Glu Ile Leu Val Gly Leu Cys Arg Val Ala Ile
            290                 295                 300

Leu Cys Trp Ile Thr Cys Thr Val Leu Lys Arg Gln Met Asp Lys Gly
305                 310                 315                 320

Arg Asp Phe Gln Leu Cys Cys Gln Thr Pro Thr Asp Leu His Ala His
            325                 330                 335

Phe Leu Ala Asp Ala Leu Thr Ser Glu Ala Gly Leu Thr Ala Asn Gln
            340                 345                 350

Tyr His Leu Gly Leu Leu Lys Arg Leu Cys Leu Leu Ala Ala Gly Gly
            355                 360                 365

Leu Phe Leu Ser Thr Leu Asn Phe Ser Gly Glu Asp Leu Arg Cys Val
            370                 375                 380

Gly Phe Thr Glu Ala Asp Val Ser Val Leu Gln Ala Ala Asn Ile Leu
385                 390                 395                 400

Leu Pro Ser Asn Thr His Lys Asp Arg Tyr Lys Phe Ile His Leu Asn
            405                 410                 415

Val Gln Glu Phe Cys Thr Ala Ile Ala Phe Leu Met Ala Val Pro Asn
            420                 425                 430

Tyr Leu Ile Pro Ser Gly Ser Arg Glu Tyr Lys Glu Lys Arg Glu Gln
```

-continued

```
                435                 440                 445
Tyr Ser Asp Phe Asn Gln Val Phe Thr Phe Ile Phe Gly Leu Leu Asn
    450                 455                 460

Ala Asn Arg Arg Lys Ile Leu Glu Thr Ser Phe Gly Tyr Gln Leu Pro
465                 470                 475                 480

Met Val Asp Ser Phe Lys Trp Tyr Ser Val Gly Tyr Met Lys His Leu
                485                 490                 495

Asp Arg Asp Pro Glu Lys Leu Thr His His Met Pro Leu Phe Tyr Cys
            500                 505                 510

Leu Tyr Glu Asn Arg Glu Glu Glu Phe Val Lys Thr Ile Val Asp Ala
        515                 520                 525

Leu Met Glu Val Thr Val Tyr Leu Gln Ser Asp Lys Asp Met Met Val
    530                 535                 540

Ser Leu Tyr Cys Leu Asp Tyr Cys Cys His Leu Arg Thr Leu Lys Leu
545                 550                 555                 560

Ser Val Gln Arg Ile Phe Gln Asn Lys Glu Pro Leu Ile Arg Pro Thr
                565                 570                 575

Ala Ser Gln Met Lys Ser Leu Val Tyr Trp Arg Glu Ile Cys Ser Leu
            580                 585                 590

Phe Tyr Thr Met Glu Ser Leu Arg Glu Leu His Ile Phe Asp Asn Asp
        595                 600                 605

Leu Asn Gly Ile Ser Glu Arg Ile Leu Ser Lys Ala Leu Glu His Ser
    610                 615                 620

Ser Cys Lys Leu Arg Thr Leu
625                 630
```

<210> SEQ ID NO 5
<211> LENGTH: 1566
<212> TYPE: DNA
<213> ORGANISM: Homo sapiens
<220> FEATURE:
<221> NAME/KEY: CDS
<222> LOCATION: (1)...(1563)

<400> SEQUENCE: 5

```
atg aag gct gaa cta ctg gag aca tgg gac aac atc agt tgg cct aaa      48
Met Lys Ala Glu Leu Leu Glu Thr Trp Asp Asn Ile Ser Trp Pro Lys
1               5                   10                  15 gac cac gta tat atc cgt aat aca tca aag gac gaa cat gag gaa ctg      96
Asp His Val Tyr Ile Arg Asn Thr Ser Lys Asp Glu His Glu Glu Leu
                20                  25                  30 cag cgc cta ctg gat cct aat agg act aga gcc cag gcc cag acg ata     144
Gln Arg Leu Leu Asp Pro Asn Arg Thr Arg Ala Gln Ala Gln Thr Ile
            35                  40                  45 gtc ttg gtg ggg agg gca ggg gtt ggg aag acc acc ttg gca atg cag     192
Val Leu Val Gly Arg Ala Gly Val Gly Lys Thr Thr Leu Ala Met Gln
        50                  55                  60 gct atg ctg cac tgg gca aat gga gtt ctc ttt cag caa agg ttc tcc     240
Ala Met Leu His Trp Ala Asn Gly Val Leu Phe Gln Gln Arg Phe Ser
65                  70                  75                  80 tat gtt ttc tat ctc agc tgc cat aaa ata agg tac atg aag gaa act     288
Tyr Val Phe Tyr Leu Ser Cys His Lys Ile Arg Tyr Met Lys Glu Thr
                85                  90                  95 acc ttt gct gaa ttg att tct ttg gat tgg ccc gat ttt gcc ccc         336
Thr Phe Ala Glu Leu Ile Ser Leu Asp Trp Pro Asp Phe Asp Ala Pro
                100                 105                 110 att gaa gag ttc atg tct caa cca gag aag ctc ctg ttt att att gat     384
Ile Glu Glu Phe Met Ser Gln Pro Glu Lys Leu Leu Phe Ile Ile Asp
```

|  |  |  |  |  |  |  |  |  |  |  |  |  |
|---|---|---|---|---|---|---|---|---|---|---|---|---|
|  |  | 115 |  |  |  | 120 |  |  |  | 125 |  |  |

```
ggc ttt gag gaa ata atc ata tct gag tca cgc tct gag agc ttg gat    432
Gly Phe Glu Glu Ile Ile Ile Ser Glu Ser Arg Ser Glu Ser Leu Asp
    130                 135                 140 gat ggc tcg cca tgt aca gac tgg tac cag gag ctc cca gtg acc aaa    480
Asp Gly Ser Pro Cys Thr Asp Trp Tyr Gln Glu Leu Pro Val Thr Lys
145                 150                 155                 160 atc cta cac agc ttg ttg aag aaa gaa ttg gtt ccc ctg gct acc tta    528
Ile Leu His Ser Leu Leu Lys Lys Glu Leu Val Pro Leu Ala Thr Leu
                165                 170                 175 ctg atc acg atc aag acc tgg ttt gtg aga gat ctt aag gcc tca tta    576
Leu Ile Thr Ile Lys Thr Trp Phe Val Arg Asp Leu Lys Ala Ser Leu
            180                 185                 190 gtg aat cca tgc ttt gta caa att aca ggg ttc aca ggg gac gac cta    624
Val Asn Pro Cys Phe Val Gln Ile Thr Gly Phe Thr Gly Asp Asp Leu
        195                 200                 205 cgg gta tat ttc atg aga cac ttt gat gac tca agt gaa gtt gag aaa    672
Arg Val Tyr Phe Met Arg His Phe Asp Asp Ser Ser Glu Val Glu Lys
    210                 215                 220 atc ctg cag cag cta aga aaa aac gaa act ctc ttt cat tcc tgc agt    720
Ile Leu Gln Gln Leu Arg Lys Asn Glu Thr Leu Phe His Ser Cys Ser
225                 230                 235                 240 gcc ccc atg gtg tgt tgg acc gta tgt tcc tgt ctg aag cag ccg aag    768
Ala Pro Met Val Cys Trp Thr Val Cys Ser Cys Leu Lys Gln Pro Lys
                245                 250                 255 gtg agg tat tac gat ctc cag tca atc act cag act acc agt ctg        816
Val Arg Tyr Tyr Asp Leu Gln Ser Ile Thr Gln Thr Thr Thr Ser Leu
            260                 265                 270 tat gcc tat ttt ttc tcc aac ttg ttc tcc aca gca gag gta gat ttg    864
Tyr Ala Tyr Phe Phe Ser Asn Leu Phe Ser Thr Ala Glu Val Asp Leu
        275                 280                 285 gca gat gac agc tgg cca gga caa tgg agg gcc ctc tgc agt ctg gcc    912
Ala Asp Asp Ser Trp Pro Gly Gln Trp Arg Ala Leu Cys Ser Leu Ala
    290                 295                 300 ata gaa ggg ctg tgg tct atg aac ttc acg ttt aac aaa gaa gac act    960
Ile Glu Gly Leu Trp Ser Met Asn Phe Thr Phe Asn Lys Glu Asp Thr
305                 310                 315                 320 gag atc gag ggc ctg gaa gtg cct ttc att gat tct ctc tac gag ttc   1008
Glu Ile Glu Gly Leu Glu Val Pro Phe Ile Asp Ser Leu Tyr Glu Phe
                325                 330                 335 aat att ctt caa aag atc aat gac tgt ggg ggt tgc act act ttc acc   1056
Asn Ile Leu Gln Lys Ile Asn Asp Cys Gly Gly Cys Thr Thr Phe Thr
            340                 345                 350 cac cta agt ttc cag gag ttt ttt gca gcc atg tcc ttt gtg cta gag   1104
His Leu Ser Phe Gln Glu Phe Phe Ala Ala Met Ser Phe Val Leu Glu
        355                 360                 365 gaa cct aga gaa ttc cct ccc cat tcc aca aag cca caa gag atg aag   1152
Glu Pro Arg Glu Phe Pro Pro His Ser Thr Lys Pro Gln Glu Met Lys
    370                 375                 380 atg tta ctg caa cac gtc ttg ctt gac aaa gaa gcc tac tgg act cca   1200
Met Leu Leu Gln His Val Leu Leu Asp Lys Glu Ala Tyr Trp Thr Pro
385                 390                 395                 400 gtg gtt ctg ttc ttc ttt ggt ctt tta aat aaa aac ata gca aga gaa   1248
Val Val Leu Phe Phe Phe Gly Leu Leu Asn Lys Asn Ile Ala Arg Glu
                405                 410                 415 ctg gaa gat act ttg cat tgt aaa ata tct ccc agg gta atg gag gaa   1296
Leu Glu Asp Thr Leu His Cys Lys Ile Ser Pro Arg Val Met Glu Glu
            420                 425                 430 tta tta aag tgg gga gaa gag tta ggt aag gct gaa agt gcc tct ctc   1344
```

-continued

```
Leu Leu Lys Trp Gly Glu Glu Leu Gly Lys Ala Glu Ser Ala Ser Leu
        435                 440                 445 caa ttt cac att cta cga ctt ttt cac tgc cta cac gag tcc cag gag      1392
Gln Phe His Ile Leu Arg Leu Phe His Cys Leu His Glu Ser Gln Glu
    450                 455                 460 gaa gac ttc aca aag aag atg ttg ggt cgt atc ttt gaa gtt gac ctt      1440
Glu Asp Phe Thr Lys Lys Met Leu Gly Arg Ile Phe Glu Val Asp Leu
465                 470                 475                 480 aat att ttg gag gac gaa gaa ctc caa gct tct tca ttt tgc cta aag      1488
Asn Ile Leu Glu Asp Glu Glu Leu Gln Ala Ser Ser Phe Cys Leu Lys
            485                 490                 495 cac tgt aaa agg tta aat aag cta agg ctt tct gtt agc agt cac atc      1536
His Cys Lys Arg Leu Asn Lys Leu Arg Leu Ser Val Ser Ser His Ile
        500                 505                 510 ctt gaa agg gac ttg gaa att ctg gag tga                              1566
Leu Glu Arg Asp Leu Glu Ile Leu Glu
        515                 520
```

<210> SEQ ID NO 6
<211> LENGTH: 521
<212> TYPE: PRT
<213> ORGANISM: Homo sapiens

<400> SEQUENCE: 6

```
Met Lys Ala Glu Leu Leu Glu Thr Trp Asp Asn Ile Ser Trp Pro Lys
  1               5                  10                  15

Asp His Val Tyr Ile Arg Asn Thr Ser Lys Asp Glu His Glu Glu Leu
            20                  25                  30

Gln Arg Leu Leu Asp Pro Asn Arg Thr Arg Ala Gln Ala Gln Thr Ile
        35                  40                  45

Val Leu Val Gly Arg Ala Gly Val Gly Lys Thr Thr Leu Ala Met Gln
    50                  55                  60

Ala Met Leu His Trp Ala Asn Gly Val Leu Phe Gln Gln Arg Phe Ser
65                  70                  75                  80

Tyr Val Phe Tyr Leu Ser Cys His Lys Ile Arg Tyr Met Lys Glu Thr
                85                  90                  95

Thr Phe Ala Glu Leu Ile Ser Leu Asp Trp Pro Asp Phe Asp Ala Pro
            100                 105                 110

Ile Glu Glu Phe Met Ser Gln Pro Glu Lys Leu Leu Phe Ile Ile Asp
        115                 120                 125

Gly Phe Glu Glu Ile Ile Ser Glu Ser Arg Ser Glu Ser Leu Asp
    130                 135                 140

Asp Gly Ser Pro Cys Thr Asp Trp Tyr Gln Glu Leu Pro Val Thr Lys
145                 150                 155                 160

Ile Leu His Ser Leu Leu Lys Lys Glu Leu Val Pro Leu Ala Thr Leu
                165                 170                 175

Leu Ile Thr Ile Lys Thr Trp Phe Val Arg Asp Leu Lys Ala Ser Leu
            180                 185                 190

Val Asn Pro Cys Phe Val Gln Ile Thr Gly Phe Thr Gly Asp Asp Leu
        195                 200                 205

Arg Val Tyr Phe Met Arg His Phe Asp Asp Ser Ser Glu Val Glu Lys
    210                 215                 220

Ile Leu Gln Gln Leu Arg Lys Asn Glu Thr Leu Phe His Ser Cys Ser
225                 230                 235                 240

Ala Pro Met Val Cys Trp Thr Val Cys Ser Cys Leu Lys Gln Pro Lys
                245                 250                 255
```

```
Val Arg Tyr Tyr Asp Leu Gln Ser Ile Thr Gln Thr Thr Ser Leu
            260                 265                 270

Tyr Ala Tyr Phe Phe Ser Asn Leu Phe Ser Thr Ala Glu Val Asp Leu
        275                 280                 285

Ala Asp Asp Ser Trp Pro Gly Gln Trp Arg Ala Leu Cys Ser Leu Ala
    290                 295                 300

Ile Glu Gly Leu Trp Ser Met Asn Phe Thr Phe Asn Lys Glu Asp Thr
305                 310                 315                 320

Glu Ile Glu Gly Leu Glu Val Pro Phe Ile Asp Ser Leu Tyr Glu Phe
                325                 330                 335

Asn Ile Leu Gln Lys Ile Asn Asp Cys Gly Gly Cys Thr Thr Phe Thr
            340                 345                 350

His Leu Ser Phe Gln Glu Phe Ala Ala Met Ser Phe Val Leu Glu
        355                 360                 365

Glu Pro Arg Glu Phe Pro Pro His Ser Thr Lys Pro Gln Glu Met Lys
    370                 375                 380

Met Leu Leu Gln His Val Leu Leu Asp Lys Glu Ala Tyr Trp Thr Pro
385                 390                 395                 400

Val Val Leu Phe Phe Gly Leu Leu Asn Lys Asn Ile Ala Arg Glu
                405                 410                 415

Leu Glu Asp Thr Leu His Cys Lys Ile Ser Pro Arg Val Met Glu Glu
            420                 425                 430

Leu Leu Lys Trp Gly Glu Glu Leu Gly Lys Ala Glu Ser Ala Ser Leu
        435                 440                 445

Gln Phe His Ile Leu Arg Leu Phe His Cys Leu His Glu Ser Gln Glu
    450                 455                 460

Glu Asp Phe Thr Lys Lys Met Leu Gly Arg Ile Phe Glu Val Asp Leu
465                 470                 475                 480

Asn Ile Leu Glu Asp Glu Glu Leu Gln Ala Ser Ser Phe Cys Leu Lys
                485                 490                 495

His Cys Lys Arg Leu Asn Lys Leu Arg Leu Ser Val Ser Ser His Ile
            500                 505                 510

Leu Glu Arg Asp Leu Glu Ile Leu Glu
        515                 520

<210> SEQ ID NO 7
<211> LENGTH: 2575
<212> TYPE: DNA
<213> ORGANISM: Homo sapiens
<220> FEATURE:
<221> NAME/KEY: CDS
<222> LOCATION: (2)...(2575)

<400> SEQUENCE: 7 c agc cgc tta tgg tcc agc aag tct gtc act gag att cac cta tac ttt      49
  Ser Arg Leu Trp Ser Ser Lys Ser Val Thr Glu Ile His Leu Tyr Phe
  1               5                  10                  15 gag gag gaa gtc aag caa gaa gaa tgt gac cat ttg gac cgc ctt ttt        97
Glu Glu Glu Val Lys Gln Glu Glu Cys Asp His Leu Asp Arg Leu Phe
                 20                  25                  30 gct ccc aag gaa gct ggg aaa cag cca cgt aca gtg atc att caa gga       145
Ala Pro Lys Glu Ala Gly Lys Gln Pro Arg Thr Val Ile Ile Gln Gly
             35                  40                  45 cca caa gga att gga aaa acg aca ctc ctg atg aag ctg atg atg gcc       193
Pro Gln Gly Ile Gly Lys Thr Thr Leu Leu Met Lys Leu Met Met Ala
         50                  55                  60 tgg tcg gac aac aag atc ttt cgg gat agg ttc ctg tac acg ttc tat       241
```

-continued

|  |  |
|---|---|
| Trp Ser Asp Asn Lys Ile Phe Arg Asp Arg Phe Leu Tyr Thr Phe Tyr<br>65     70      75     80 |  |
| ttc tgc tgc aga gaa ctg agg gag ttg ccg cca acg agt ttg gct gac<br>Phe Cys Cys Arg Glu Leu Arg Glu Leu Pro Pro Thr Ser Leu Ala Asp<br>     85      90     95 | 289 |
| ttg att tcc aga gag tgg cct gac ccc gct gct cct ata aca gag atc<br>Leu Ile Ser Arg Glu Trp Pro Asp Pro Ala Ala Pro Ile Thr Glu Ile<br>    100      105     110 | 337 |
| gtg tct caa ccg gag aga ctc ttg ttc gtc atc gac agc ttc gaa gag<br>Val Ser Gln Pro Glu Arg Leu Leu Phe Val Ile Asp Ser Phe Glu Glu<br>   115      120     125 | 385 |
| ctg cag ggc ggc ttg aac gaa ccc gat tcg gat ctg tgt ggt gac ttg<br>Leu Gln Gly Gly Leu Asn Glu Pro Asp Ser Asp Leu Cys Gly Asp Leu<br>130      135     140 | 433 |
| atg gag aaa cgg ccg gtg cag gtg ctt ctg agc agt ttg ctg agg aag<br>Met Glu Lys Arg Pro Val Gln Val Leu Leu Ser Ser Leu Leu Arg Lys<br>145      150      155     160 | 481 |
| aag atg ctc ccg gag gcc tcc ctg ctc atc gct atc aaa ccc gtg tgc<br>Lys Met Leu Pro Glu Ala Ser Leu Leu Ile Ala Ile Lys Pro Val Cys<br>     165      170     175 | 529 |
| ccg aag gag ctc cgg gat cag gtg acg atc tca gaa atc tac cag ccc<br>Pro Lys Glu Leu Arg Asp Gln Val Thr Ile Ser Glu Ile Tyr Gln Pro<br>    180      185     190 | 577 |
| cgg gga ttc aac gag agt gat agg tta gtg tat ttc tgc tgt ttc ttc<br>Arg Gly Phe Asn Glu Ser Asp Arg Leu Val Tyr Phe Cys Cys Phe Phe<br>   195      200     205 | 625 |
| aaa gac ccg aaa aga gcc atg gaa gcc ttc aat ctt gta aga gaa agt<br>Lys Asp Pro Lys Arg Ala Met Glu Ala Phe Asn Leu Val Arg Glu Ser<br>210      215     220 | 673 |
| gaa cag ctg ttt tcc ata tgc caa atc ccg ctc ctc tgc tgg atc ctg<br>Glu Gln Leu Phe Ser Ile Cys Gln Ile Pro Leu Leu Cys Trp Ile Leu<br>225      230      235     240 | 721 |
| tgt acc agt ctg aag caa gag atg cag aaa gga aaa gac ctg gcc ctg<br>Cys Thr Ser Leu Lys Gln Glu Met Gln Lys Gly Lys Asp Leu Ala Leu<br>     245      250     255 | 769 |
| acc tgc cag agc act acc tct gtg tac tcc tct ttc gtc ttt aac ctg<br>Thr Cys Gln Ser Thr Thr Ser Val Tyr Ser Ser Phe Val Phe Asn Leu<br>    260      265     270 | 817 |
| ttc aca cct gag ggt gcc gag ggc ccg act ccg caa acc cag cac cag<br>Phe Thr Pro Glu Gly Ala Glu Gly Pro Thr Pro Gln Thr Gln His Gln<br>   275      280     285 | 865 |
| ctg aag gcc ctg tgc tcc ctg gct gca gag ggt atg tgg aca gac aca<br>Leu Lys Ala Leu Cys Ser Leu Ala Ala Glu Gly Met Trp Thr Asp Thr<br>290      295     300 | 913 |
| ttt gag ttt tgt gaa gac gac ctc cgg aga aat ggg gtt gtt gac gct<br>Phe Glu Phe Cys Glu Asp Asp Leu Arg Arg Asn Gly Val Val Asp Ala<br>305      310      315     320 | 961 |
| gac atc cct gcg ctg ctg ggc acc aag ata ctt ctg aag tac ggg gag<br>Asp Ile Pro Ala Leu Leu Gly Thr Lys Ile Leu Leu Lys Tyr Gly Glu<br>     325      330     335 | 1009 |
| cgt gag agc tcc tac gtg ttc ctc cac gtg tgt atc cag gag ttc tgt<br>Arg Glu Ser Ser Tyr Val Phe Leu His Val Cys Ile Gln Glu Phe Cys<br>    340      345     350 | 1057 |
| gcc gcc ttg ttc tat ttg ctc aag agc cac ctt gat cat cct cac cca<br>Ala Ala Leu Phe Tyr Leu Leu Lys Ser His Leu Asp His Pro His Pro<br>   355      360     365 | 1105 |
| gct gtg aga tgt gta cag gaa ttg cta gtt gcc aat ttt gaa aaa gca<br>Ala Val Arg Cys Val Gln Glu Leu Leu Val Ala Asn Phe Glu Lys Ala<br>370      375     380 | 1153 |

-continued

| | |
|---|---|
| agg aga gca cat tgg att ttt ttg ggg tgt ttt cta act ggc ctt tta<br>Arg Arg Ala His Trp Ile Phe Leu Gly Cys Phe Leu Thr Gly Leu Leu<br>385                           390                        395                    400 | 1201 |
| aat aaa aag gaa caa gaa aaa ctg gat gcg ttt ttt ggc ttc caa ctg<br>Asn Lys Lys Glu Gln Glu Lys Leu Asp Ala Phe Phe Gly Phe Gln Leu<br>                       405                       410                       415 | 1249 |
| tcc caa gag ata aag cag caa att cac cag tgc ctg aag agc tta ggg<br>Ser Gln Glu Ile Lys Gln Gln Ile His Gln Cys Leu Lys Ser Leu Gly<br>                420                       425                       430 | 1297 |
| gag cgt ggc aat cct cag gga cag gtg gat tcc ttg gcg ata ttt tac<br>Glu Arg Gly Asn Pro Gln Gly Gln Val Asp Ser Leu Ala Ile Phe Tyr<br>         435                       440                       445 | 1345 |
| tgt ctc ttt gaa atg cag gat cct gcc ttt gtg aag cag gca gtg aac<br>Cys Leu Phe Glu Met Gln Asp Pro Ala Phe Val Lys Gln Ala Val Asn<br>450                           455                       460 | 1393 |
| ctc ctc caa gaa gct aac ttt cat att att gac aac gtg gac ttg gtg<br>Leu Leu Gln Glu Ala Asn Phe His Ile Ile Asp Asn Val Asp Leu Val<br>465                           470                       475                    480 | 1441 |
| gtt tct gcc tac tgc tta aaa tac tgc tcc agc ttg agg aaa ctc tgt<br>Val Ser Ala Tyr Cys Leu Lys Tyr Cys Ser Ser Leu Arg Lys Leu Cys<br>                       485                       490                       495 | 1489 |
| ttt tcc gtt caa aat gtc ttt aag aaa gag gat gaa cac agc tct acg<br>Phe Ser Val Gln Asn Val Phe Lys Lys Glu Asp Glu His Ser Ser Thr<br>                 500                       505                       510 | 1537 |
| tcg gat tac agc ctc atc tgt tgg cat cac atc tgc tct gtg ctc acc<br>Ser Asp Tyr Ser Leu Ile Cys Trp His His Ile Cys Ser Val Leu Thr<br>             515                       520                       525 | 1585 |
| acc agc ggg cac ctc aga gag ctc cag gtg cag gac agc acc ctc agc<br>Thr Ser Gly His Leu Arg Glu Leu Gln Val Gln Asp Ser Thr Leu Ser<br>         530                       535                       540 | 1633 |
| gag tcg acc ttt gtg acc tgg tgt aac cag ctg agg cat ccc agc tgt<br>Glu Ser Thr Phe Val Thr Trp Cys Asn Gln Leu Arg His Pro Ser Cys<br>545                           550                       555                    560 | 1681 |
| cgc ctt cag aag ctt gga ata aat aac gtt tcc ttt tct ggc cag agt<br>Arg Leu Gln Lys Leu Gly Ile Asn Asn Val Ser Phe Ser Gly Gln Ser<br>                       565                       570                       575 | 1729 |
| gtt ctg ctc ttt gag gtg ctc ttt tat cag cca gac ttg aaa tac ctg<br>Val Leu Leu Phe Glu Val Leu Phe Tyr Gln Pro Asp Leu Lys Tyr Leu<br>                 580                       585                       590 | 1777 |
| agc ttc acc ctc acg aaa ctc tct cgt gat gac atc agg tcc ctc tgt<br>Ser Phe Thr Leu Thr Lys Leu Ser Arg Asp Asp Ile Arg Ser Leu Cys<br>             595                       600                       605 | 1825 |
| gat gcc ttg aac tac cca gca ggc aac gtc aaa gag cta gcg ctg gta<br>Asp Ala Leu Asn Tyr Pro Ala Gly Asn Val Lys Glu Leu Ala Leu Val<br>         610                       615                       620 | 1873 |
| aat tgt cac ctc tca ccc att gat tgt gaa gtc ctt gct ggc ctt cta<br>Asn Cys His Leu Ser Pro Ile Asp Cys Glu Val Leu Ala Gly Leu Leu<br>625                           630                       635                    640 | 1921 |
| acc aac aac aag aag ctg acg tat ctg aat gta tcc tgc aac cag tta<br>Thr Asn Asn Lys Lys Leu Thr Tyr Leu Asn Val Ser Cys Asn Gln Leu<br>                       645                       650                       655 | 1969 |
| gac aca ggc gtg ccc ctt ttg tgt gaa gcc ctg tgc agc cca gac acg<br>Asp Thr Gly Val Pro Leu Leu Cys Glu Ala Leu Cys Ser Pro Asp Thr<br>         660                       665                       670 | 2017 |
| gtc ctg gta tac ctg atg ttg gct ttc tgc cac ctc agc gag cag tgc<br>Val Leu Val Tyr Leu Met Leu Ala Phe Cys His Leu Ser Glu Gln Cys<br>             675                       680                       685 | 2065 |
| tgc gaa tac atc tct gaa atg ctt ctg cgt aac aag agc gtg cgc tat<br>Cys Glu Tyr Ile Ser Glu Met Leu Leu Arg Asn Lys Ser Val Arg Tyr<br>         690                       695                       700 | 2113 |

-continued

```
cta gac ctc agt gcc aat gtc ctg aag gac gaa gga ctg aaa act ctc    2161
Leu Asp Leu Ser Ala Asn Val Leu Lys Asp Glu Gly Leu Lys Thr Leu
705                 710                 715                 720 tgc gag gcc ttg aaa cat ccg gac tgc tgc ctg gat tca ctg tgt ttg    2209
Cys Glu Ala Leu Lys His Pro Asp Cys Cys Leu Asp Ser Leu Cys Leu
            725                 730                 735 gta aaa tgt ttt atc act gct gct ggc tgt gaa gac ctc gcc tct gct    2257
Val Lys Cys Phe Ile Thr Ala Ala Gly Cys Glu Asp Leu Ala Ser Ala
        740                 745                 750 ctc atc agc aat caa aac ctg aag att ctg caa att ggg tgc aat gaa    2305
Leu Ile Ser Asn Gln Asn Leu Lys Ile Leu Gln Ile Gly Cys Asn Glu
    755                 760                 765 atc gga gat gtg ggt gtg cag ctg ttg tgt cgg gct ctg acg cat acg    2353
Ile Gly Asp Val Gly Val Gln Leu Leu Cys Arg Ala Leu Thr His Thr
770                 775                 780 gat tgc cgc tta gag att ctt ggg ttg gaa gaa tgt ggg tta acg agc    2401
Asp Cys Arg Leu Glu Ile Leu Gly Leu Glu Glu Cys Gly Leu Thr Ser
785                 790                 795                 800 acc tgc tgt aag gat ctc gcg tct gtt ctc acc tgc agt aag acc ctg    2449
Thr Cys Cys Lys Asp Leu Ala Ser Val Leu Thr Cys Ser Lys Thr Leu
            805                 810                 815 cag cag ctc aac ctg acc ttg aac acc ttg gac cac aca ggg gtg gtt    2497
Gln Gln Leu Asn Leu Thr Leu Asn Thr Leu Asp His Thr Gly Val Val
        820                 825                 830 gta ctc tgt gag gcc ctg aga cac cca gag tgt gcc ctg cag gtg ctc    2545
Val Leu Cys Glu Ala Leu Arg His Pro Glu Cys Ala Leu Gln Val Leu
    835                 840                 845 ggg gtt gtt gca gga gta aga acc aag cag                            2575
Gly Val Val Ala Gly Val Arg Thr Lys Gln
850                 855
```

<210> SEQ ID NO 8
<211> LENGTH: 858
<212> TYPE: PRT
<213> ORGANISM: Homo sapiens

<400> SEQUENCE: 8

```
Ser Arg Leu Trp Ser Ser Lys Ser Val Thr Glu Ile His Leu Tyr Phe
1               5                   10                  15

Glu Glu Glu Val Lys Gln Glu Glu Cys Asp His Leu Asp Arg Leu Phe
            20                  25                  30

Ala Pro Lys Glu Ala Gly Lys Gln Pro Arg Thr Val Ile Ile Gln Gly
        35                  40                  45

Pro Gln Gly Ile Gly Lys Thr Thr Leu Leu Met Lys Leu Met Met Ala
    50                  55                  60

Trp Ser Asp Asn Lys Ile Phe Arg Asp Arg Phe Leu Tyr Thr Phe Tyr
65                  70                  75                  80

Phe Cys Cys Arg Glu Leu Arg Glu Leu Pro Thr Ser Leu Ala Asp
                85                  90                  95

Leu Ile Ser Arg Glu Trp Pro Asp Pro Ala Ala Pro Ile Thr Glu Ile
            100                 105                 110

Val Ser Gln Pro Glu Arg Leu Leu Phe Val Ile Asp Ser Phe Glu Glu
        115                 120                 125

Leu Gln Gly Gly Leu Asn Glu Pro Asp Ser Asp Leu Cys Gly Asp Leu
    130                 135                 140

Met Glu Lys Arg Pro Val Gln Val Leu Leu Ser Ser Leu Leu Arg Lys
145                 150                 155                 160
```

-continued

```
Lys Met Leu Pro Glu Ala Ser Leu Leu Ile Ala Ile Lys Pro Val Cys
            165                 170                 175
Pro Lys Glu Leu Arg Asp Gln Val Thr Ile Ser Glu Ile Tyr Gln Pro
            180                 185                 190
Arg Gly Phe Asn Glu Ser Asp Arg Leu Val Tyr Phe Cys Cys Phe Phe
            195                 200                 205
Lys Asp Pro Lys Arg Ala Met Glu Ala Phe Asn Leu Val Arg Glu Ser
210                 215                 220
Glu Gln Leu Phe Ser Ile Cys Gln Ile Pro Leu Leu Cys Trp Ile Leu
225                 230                 235                 240
Cys Thr Ser Leu Lys Gln Glu Met Gln Lys Gly Lys Asp Leu Ala Leu
            245                 250                 255
Thr Cys Gln Ser Thr Thr Ser Val Tyr Ser Ser Phe Val Phe Asn Leu
            260                 265                 270
Phe Thr Pro Glu Gly Ala Glu Gly Pro Thr Pro Gln Thr Gln His Gln
            275                 280                 285
Leu Lys Ala Leu Cys Ser Leu Ala Ala Glu Gly Met Trp Thr Asp Thr
            290                 295                 300
Phe Glu Phe Cys Glu Asp Asp Leu Arg Arg Asn Gly Val Val Asp Ala
305                 310                 315                 320
Asp Ile Pro Ala Leu Leu Gly Thr Lys Ile Leu Leu Lys Tyr Gly Glu
            325                 330                 335
Arg Glu Ser Ser Tyr Val Phe Leu His Val Cys Ile Gln Glu Phe Cys
            340                 345                 350
Ala Ala Leu Phe Tyr Leu Leu Lys Ser His Leu Asp His Pro His Pro
            355                 360                 365
Ala Val Arg Cys Val Gln Glu Leu Leu Val Ala Asn Phe Glu Lys Ala
            370                 375                 380
Arg Arg Ala His Trp Ile Phe Leu Gly Cys Phe Leu Thr Gly Leu Leu
385                 390                 395                 400
Asn Lys Lys Glu Gln Glu Lys Leu Asp Ala Phe Phe Gly Phe Gln Leu
            405                 410                 415
Ser Gln Glu Ile Lys Gln Ile His Gln Cys Leu Lys Ser Leu Gly
            420                 425                 430
Glu Arg Gly Asn Pro Gln Gly Gln Val Asp Ser Leu Ala Ile Phe Tyr
            435                 440                 445
Cys Leu Phe Glu Met Gln Asp Pro Ala Phe Val Lys Gln Ala Val Asn
450                 455                 460
Leu Leu Gln Glu Ala Asn Phe His Ile Ile Asp Asn Val Asp Leu Val
465                 470                 475                 480
Val Ser Ala Tyr Cys Leu Lys Tyr Cys Ser Ser Leu Arg Lys Leu Cys
            485                 490                 495
Phe Ser Val Gln Asn Val Phe Lys Lys Glu Asp Glu His Ser Ser Thr
            500                 505                 510
Ser Asp Tyr Ser Leu Ile Cys Trp His His Ile Cys Ser Val Leu Thr
            515                 520                 525
Thr Ser Gly His Leu Arg Glu Leu Gln Val Gln Asp Ser Thr Leu Ser
            530                 535                 540
Glu Ser Thr Phe Val Thr Trp Cys Asn Gln Leu Arg His Pro Ser Cys
545                 550                 555                 560
Arg Leu Gln Lys Leu Gly Ile Asn Asn Val Ser Phe Ser Gly Gln Ser
            565                 570                 575
Val Leu Leu Phe Glu Val Leu Phe Tyr Gln Pro Asp Leu Lys Tyr Leu
```

```
                    580                 585                 590
Ser Phe Thr Leu Thr Lys Leu Ser Arg Asp Asp Ile Arg Ser Leu Cys
        595                 600                 605

Asp Ala Leu Asn Tyr Pro Ala Gly Asn Val Lys Glu Leu Ala Leu Val
        610                 615                 620

Asn Cys His Leu Ser Pro Ile Asp Cys Glu Val Leu Ala Gly Leu Leu
625                 630                 635                 640

Thr Asn Asn Lys Lys Leu Thr Tyr Leu Asn Val Ser Cys Asn Gln Leu
                645                 650                 655

Asp Thr Gly Val Pro Leu Leu Cys Glu Ala Leu Cys Ser Pro Asp Thr
            660                 665                 670

Val Leu Val Tyr Leu Met Leu Ala Phe Cys His Leu Ser Glu Gln Cys
        675                 680                 685

Cys Glu Tyr Ile Ser Glu Met Leu Arg Asn Lys Ser Val Arg Tyr
        690                 695                 700

Leu Asp Leu Ser Ala Asn Val Leu Lys Asp Glu Gly Leu Lys Thr Leu
705                 710                 715                 720

Cys Glu Ala Leu Lys His Pro Asp Cys Cys Leu Asp Ser Leu Cys Leu
                725                 730                 735

Val Lys Cys Phe Ile Thr Ala Ala Gly Cys Glu Asp Leu Ala Ser Ala
            740                 745                 750

Leu Ile Ser Asn Gln Asn Leu Lys Ile Leu Gln Ile Gly Cys Asn Glu
        755                 760                 765

Ile Gly Asp Val Gly Val Gln Leu Leu Cys Arg Ala Leu Thr His Thr
    770                 775                 780

Asp Cys Arg Leu Glu Ile Leu Gly Leu Glu Glu Cys Gly Leu Thr Ser
785                 790                 795                 800

Thr Cys Cys Lys Asp Leu Ala Ser Val Leu Thr Cys Ser Lys Thr Leu
                805                 810                 815

Gln Gln Leu Asn Leu Thr Leu Asn Thr Leu Asp His Thr Gly Val Val
            820                 825                 830

Val Leu Cys Glu Ala Leu Arg His Pro Glu Cys Ala Leu Gln Val Leu
        835                 840                 845

Gly Val Val Ala Gly Val Arg Thr Lys Gln
    850                 855

<210> SEQ ID NO 9
<211> LENGTH: 15
<212> TYPE: PRT
<213> ORGANISM: Homo sapiens

<400> SEQUENCE: 9

Ile Val Gly Met Gly Gly Ile Gly Lys Thr Thr Leu Ala Lys Gln
1               5                   10                  15

<210> SEQ ID NO 10
<211> LENGTH: 28
<212> TYPE: PRT
<213> ORGANISM: Homo sapiens

<400> SEQUENCE: 10

Asn Pro Ser Leu Arg Glu Leu Asp Leu Ser Asn Asn Lys Leu Gly Asp
1               5                   10                  15

Glu Gly Ala Arg Ala Leu Ala Glu Ala Leu Lys Ser
            20                  25
```

```
<210> SEQ ID NO 11
<211> LENGTH: 28
<212> TYPE: PRT
<213> ORGANISM: Homo sapiens

<400> SEQUENCE: 11

Ile Val Gly Met Gly Gly Ile Gly Lys Thr Thr Leu Ala Lys Gln Ile
1               5                   10                  15

Tyr Asn Asp Glu Ser Gln Glu Val Gln Arg His Phe
            20                  25

<210> SEQ ID NO 12
<211> LENGTH: 3263
<212> TYPE: DNA
<213> ORGANISM: Homo sapiens
<220> FEATURE:
<221> NAME/KEY: CDS
<222> LOCATION: (59)...(2998)

<400> SEQUENCE: 12
gaattcgaat tcggggaagt tcttcagcct taacctaagg tctcatactc ggagcact         58 atg aca tcg ccc cag cta gag tgg act ctg cag acc ctt ctg gag cag        106
Met Thr Ser Pro Gln Leu Glu Trp Thr Leu Gln Thr Leu Leu Glu Gln
1               5                   10                  15 ctg aac gag gat gaa tta aag agt ttc aaa tcc ctt tta tgg gct ttt        154
Leu Asn Glu Asp Glu Leu Lys Ser Phe Lys Ser Leu Leu Trp Ala Phe
            20                  25                  30 ccc ctc gaa gac gtg cta cag aag acc cca tgg tct gag gtg gaa gag        202
Pro Leu Glu Asp Val Leu Gln Lys Thr Pro Trp Ser Glu Val Glu Glu
        35                  40                  45 gct gat ggc aag aaa ctg gca gaa att ctg gtc aac acc tcc tca gaa        250
Ala Asp Gly Lys Lys Leu Ala Glu Ile Leu Val Asn Thr Ser Ser Glu
    50                  55                  60 aat tgg ata agg aat gcg act gtg aac atc ttg gaa gag atg aat ctc        298
Asn Trp Ile Arg Asn Ala Thr Val Asn Ile Leu Glu Glu Met Asn Leu
65                  70                  75                  80 acg gaa ttg tgt aag atg gca aag gct gag atg atg gag gac gga cag        346
Thr Glu Leu Cys Lys Met Ala Lys Ala Glu Met Met Glu Asp Gly Gln
                85                  90                  95 gtg caa gaa ata gat aat cct gag ctg gga gat gca gaa gaa gac tcg        394
Val Gln Glu Ile Asp Asn Pro Glu Leu Gly Asp Ala Glu Glu Asp Ser
            100                 105                 110 gag tta gca aag cca ggt gaa aag gaa gga tgg aga aat tca atg gag        442
Glu Leu Ala Lys Pro Gly Glu Lys Glu Gly Trp Arg Asn Ser Met Glu
        115                 120                 125 aaa cag tct ttg gtc tgg aag aac acc ttt tgg caa gga gac att gac        490
Lys Gln Ser Leu Val Trp Lys Asn Thr Phe Trp Gln Gly Asp Ile Asp
    130                 135                 140 aat ttc cat gac gac gtc act ctg aga aac caa cgg ttc att cca ttc        538
Asn Phe His Asp Asp Val Thr Leu Arg Asn Gln Arg Phe Ile Pro Phe
145                 150                 155                 160 ttg aat ccc aga aca ccc agg aag cta aca cct tac acg gtg gtg ctg        586
Leu Asn Pro Arg Thr Pro Arg Lys Leu Thr Pro Tyr Thr Val Val Leu
                165                 170                 175 cac ggc ccc gca ggc gtg ggg aaa acc acg ctg gcc aaa aag tgt atg        634
His Gly Pro Ala Gly Val Gly Lys Thr Thr Leu Ala Lys Lys Cys Met
            180                 185                 190 ctg gac tgg aca gac tgc aac ctc agc ccg acg ctg aga tac gcg ttc        682
Leu Asp Trp Thr Asp Cys Asn Leu Ser Pro Thr Leu Arg Tyr Ala Phe
        195                 200                 205 tac ctc agc tgc aag gag ctc agc cgc atg ggc ccc tgc agt ttt gca        730
```

```
                Tyr Leu Ser Cys Lys Glu Leu Ser Arg Met Gly Pro Cys Ser Phe Ala
                    210                 215                 220 gag ctg atc tcc aaa gac tgg cct gaa ttg cag gat gac att cca agc        778
Glu Leu Ile Ser Lys Asp Trp Pro Glu Leu Gln Asp Asp Ile Pro Ser
225                 230                 235                 240 atc cta gcc caa gca cag aga atc ctg ttc gtg gtc gat ggc ctt gat        826
Ile Leu Ala Gln Ala Gln Arg Ile Leu Phe Val Val Asp Gly Leu Asp
                245                 250                 255 gag ctg aaa gtc cca cct ggg gcg ctg atc cag gac atc tgc ggg gac        874
Glu Leu Lys Val Pro Pro Gly Ala Leu Ile Gln Asp Ile Cys Gly Asp
            260                 265                 270 tgg gag aag aag aag ccg gtg ccc gtc ctc ctg ggg agt ttg ctg aag        922
Trp Glu Lys Lys Lys Pro Val Pro Val Leu Leu Gly Ser Leu Leu Lys
        275                 280                 285 agg aag atg tta ccc agg gca gcc ttg ctg gtc acc acg cgg ccc agg        970
Arg Lys Met Leu Pro Arg Ala Ala Leu Leu Val Thr Thr Arg Pro Arg
    290                 295                 300 gca ctg agg gac ctc cag ctc ctg gcg cag cag ccg atc tac gta agg       1018
Ala Leu Arg Asp Leu Gln Leu Leu Ala Gln Gln Pro Ile Tyr Val Arg
305                 310                 315                 320 gtg gag ggc ttc ctg gag gag gac agg agg gcc tat ttc ctg aga cac       1066
Val Glu Gly Phe Leu Glu Glu Asp Arg Arg Ala Tyr Phe Leu Arg His
                325                 330                 335 ttt gga gac gag gac caa gcc atg cgt gcc ttt gag cta atg agg agc       1114
Phe Gly Asp Glu Asp Gln Ala Met Arg Ala Phe Glu Leu Met Arg Ser
                340                 345                 350 aac gcg gcc ctg ttc cag ctg ggc tcg gcc ccc gcg gtg tgc tgg att       1162
Asn Ala Ala Leu Phe Gln Leu Gly Ser Ala Pro Ala Val Cys Trp Ile
            355                 360                 365 gtg tgc acg act ctg aag ctg cag atg gag aag ggg gag gac ccg gtc       1210
Val Cys Thr Thr Leu Lys Leu Gln Met Glu Lys Gly Glu Asp Pro Val
        370                 375                 380 ccc acc tgc ctc acc cgc acg ggg ctg ttc ctg cgt ttc ctc tgc agc       1258
Pro Thr Cys Leu Thr Arg Thr Gly Leu Phe Leu Arg Phe Leu Cys Ser
385                 390                 395                 400 cgg ttc ccg cag ggc gca cag ctg cgg ggc gcg ctg cgg acg ctg agc       1306
Arg Phe Pro Gln Gly Ala Gln Leu Arg Gly Ala Leu Arg Thr Leu Ser
                405                 410                 415 ctc ctg gcc gcg cag ggc ctg tgg gcg cag atg tcc gtg ttc cac cga       1354
Leu Leu Ala Ala Gln Gly Leu Trp Ala Gln Met Ser Val Phe His Arg
                420                 425                 430 gag gac ctg gaa agg ctc ggg gtg cag gag tcc gac ctc cgt ctg ttc       1402
Glu Asp Leu Glu Arg Leu Gly Val Gln Glu Ser Asp Leu Arg Leu Phe
            435                 440                 445 ctg gac gga gac atc ctc cgc cag gac aga gtc tcc aaa ggc tgc tac       1450
Leu Asp Gly Asp Ile Leu Arg Gln Asp Arg Val Ser Lys Gly Cys Tyr
        450                 455                 460 tcc ttc atc cac ctc agc ttc cag cag ttt ctc act gcc ctg ttc tac       1498
Ser Phe Ile His Leu Ser Phe Gln Gln Phe Leu Thr Ala Leu Phe Tyr
465                 470                 475                 480 gcc ctg gag aag gag gag ggg gag gac agg gac ggc cac gcc tgg gac       1546
Ala Leu Glu Lys Glu Glu Gly Glu Asp Arg Asp Gly His Ala Trp Asp
                485                 490                 495 atc ggg gac gta cag aag ctg ctt tcc gga gaa gaa aga ctc aag aac       1594
Ile Gly Asp Val Gln Lys Leu Leu Ser Gly Glu Glu Arg Leu Lys Asn
                500                 505                 510 ccc gac ctg att caa gta gga cac ttc tta ttc ggc ctc gct aac gag       1642
Pro Asp Leu Ile Gln Val Gly His Phe Leu Phe Gly Leu Ala Asn Glu
            515                 520                 525
```

```
aag aga gcc aag gag ttg gag gcc act ttt ggc tgc cgg atg tca ccg      1690
Lys Arg Ala Lys Glu Leu Glu Ala Thr Phe Gly Cys Arg Met Ser Pro
530                 535                 540 gac atc aaa cag gaa ttg ctg caa tgc aaa gca cat ctt cat gca aat      1738
Asp Ile Lys Gln Glu Leu Leu Gln Cys Lys Ala His Leu His Ala Asn
545                 550                 555                 560 aag ccc tta tcc gtg acc gac ctg aag gag gtc ttg ggc tgc ctg tat      1786
Lys Pro Leu Ser Val Thr Asp Leu Lys Glu Val Leu Gly Cys Leu Tyr
                565                 570                 575 gag tct cag gag gag gag ctg gcg aag gtg gtg gtg gcc ccg ttc aag      1834
Glu Ser Gln Glu Glu Glu Leu Ala Lys Val Val Val Ala Pro Phe Lys
            580                 585                 590 gaa att tct att cac ctg aca aat act tct gaa gtg atg cat tgt tcc      1882
Glu Ile Ser Ile His Leu Thr Asn Thr Ser Glu Val Met His Cys Ser
        595                 600                 605 ttc agc ctg aag cat tgt caa gac ttg cag aaa ctc tca ctg cag gta      1930
Phe Ser Leu Lys His Cys Gln Asp Leu Gln Lys Leu Ser Leu Gln Val
    610                 615                 620 gca aag ggg gtg ttc ctg gag aat tac atg gat ttt gaa ctg gac att      1978
Ala Lys Gly Val Phe Leu Glu Asn Tyr Met Asp Phe Glu Leu Asp Ile
625                 630                 635                 640 gaa ttt gaa agg tgc act tac cta acc att ccg aac tgg gct cgg cag      2026
Glu Phe Glu Arg Cys Thr Tyr Leu Thr Ile Pro Asn Trp Ala Arg Gln
                645                 650                 655 gat ctt cgc tct ctt cgc ctc tgg aca gat ttc tgc tct ctc ttc agc      2074
Asp Leu Arg Ser Leu Arg Leu Trp Thr Asp Phe Cys Ser Leu Phe Ser
            660                 665                 670 tca aac agc aac ctc aag ttt ctg gaa gtg aaa caa agc ttc ctg agt      2122
Ser Asn Ser Asn Leu Lys Phe Leu Glu Val Lys Gln Ser Phe Leu Ser
        675                 680                 685 gac tct tct gtg cgg att ctt tgt gac cac gta acc cgt agc acc tgt      2170
Asp Ser Ser Val Arg Ile Leu Cys Asp His Val Thr Arg Ser Thr Cys
    690                 695                 700 cat ctg cag aaa gtg gag att aaa aac gtc acc cct gac acc gcg tac      2218
His Leu Gln Lys Val Glu Ile Lys Asn Val Thr Pro Asp Thr Ala Tyr
705                 710                 715                 720 cgg gac ttc tgt ctt gct ttc att ggg aag aag acc ctc acg cac ctg      2266
Arg Asp Phe Cys Leu Ala Phe Ile Gly Lys Lys Thr Leu Thr His Leu
                725                 730                 735 acc ctg gca ggg cac atc gag tgg gaa cgc acg atg atg ctg atg ctg      2314
Thr Leu Ala Gly His Ile Glu Trp Glu Arg Thr Met Met Leu Met Leu
            740                 745                 750 tgt gac ctg ctc aga aat cat aaa tgc aac ctg cag tac ctg agg ttg      2362
Cys Asp Leu Leu Arg Asn His Lys Cys Asn Leu Gln Tyr Leu Arg Leu
        755                 760                 765 gga ggt cac tgt gcc acc ccg gag cag tgg gct gaa ttc ttc tat gtc      2410
Gly Gly His Cys Ala Thr Pro Glu Gln Trp Ala Glu Phe Phe Tyr Val
    770                 775                 780 ctc aaa gcc aac cag tcc ctg aag cac ctg cgt ctc tca gcc aat gtg      2458
Leu Lys Ala Asn Gln Ser Leu Lys His Leu Arg Leu Ser Ala Asn Val
785                 790                 795                 800 ctc ctg gat gag ggt gcc atg ttg ctg tac aag acc atg aca cgc cca      2506
Leu Leu Asp Glu Gly Ala Met Leu Leu Tyr Lys Thr Met Thr Arg Pro
                805                 810                 815 aaa cac ttc ctg cag atg ttg tcg ttg gaa aac tgt cgt ctt aca gaa      2554
Lys His Phe Leu Gln Met Leu Ser Leu Glu Asn Cys Arg Leu Thr Glu
            820                 825                 830 gcc agt tgc aag gac ctt gct gct gtc ttg gtt gtc agc aag aag ctg      2602
Ala Ser Cys Lys Asp Leu Ala Ala Val Leu Val Val Ser Lys Lys Leu
        835                 840                 845
```

```
aca cac ctg tgc ttg gcc aag aac ccc att ggg gat aca ggg gtg aag         2650
Thr His Leu Cys Leu Ala Lys Asn Pro Ile Gly Asp Thr Gly Val Lys
    850                 855                 860 ttt ctg tgt gag ggc ttg agt tac cct gat tgt aaa ctg cag acc ttg         2698
Phe Leu Cys Glu Gly Leu Ser Tyr Pro Asp Cys Lys Leu Gln Thr Leu
865                 870                 875                 880 gtg tta cag caa tgc agc ata acc aag ctt ggc tgt aga tat ctc tca         2746
Val Leu Gln Gln Cys Ser Ile Thr Lys Leu Gly Cys Arg Tyr Leu Ser
                885                 890                 895 gag gcg ctc caa gaa gcc tgc agc ctc aca aac ctg gac ttg agt atc         2794
Glu Ala Leu Gln Glu Ala Cys Ser Leu Thr Asn Leu Asp Leu Ser Ile
            900                 905                 910 aac cag ata gct cgt gga ttg tgg att ctc tgt cag gca tta gag aat         2842
Asn Gln Ile Ala Arg Gly Leu Trp Ile Leu Cys Gln Ala Leu Glu Asn
        915                 920                 925 cca aac tgt aac cta aaa cac cta cgg ttg aag acc tat gaa act aat         2890
Pro Asn Cys Asn Leu Lys His Leu Arg Leu Lys Thr Tyr Glu Thr Asn
    930                 935                 940 ttg gaa atc aag aag ctg ttg gag gaa gtg aaa gaa aag aat ccc aag         2938
Leu Glu Ile Lys Lys Leu Leu Glu Glu Val Lys Glu Lys Asn Pro Lys
945                 950                 955                 960 ctg act att gat tgc aat gct tcc ggg gca acg gca cct ccg tgc tgt         2986
Leu Thr Ile Asp Cys Asn Ala Ser Gly Ala Thr Ala Pro Pro Cys Cys
                965                 970                 975 gac ttt ttt tgc tgagcagcct gggatcgctc tacgaattac acaggaagcg             3038
Asp Phe Phe Cys
                980 ggattcgggt ctctaagatg tcttatgaat gcaggtcaga gggtcacatg ttaacactag       3098 agtctgtcga gaggtaggat ttgacactgg ttttctcact attttggga gattctgcac        3158 gagtcacgca ccccttcac atgacgctat gtactttctc acagggataa taaagttaga       3218 gcactctcaa aaaaaaaaaa aaaaaaaaaa aaaaaaaaaa aaaaa                       3263

<210> SEQ ID NO 13
<211> LENGTH: 980
<212> TYPE: PRT
<213> ORGANISM: Homo sapiens

<400> SEQUENCE: 13

Met Thr Ser Pro Gln Leu Glu Trp Thr Leu Gln Thr Leu Leu Glu Gln
1               5                   10                  15

Leu Asn Glu Asp Glu Leu Lys Ser Phe Lys Ser Leu Leu Trp Ala Phe
            20                  25                  30

Pro Leu Glu Asp Val Leu Gln Lys Thr Pro Trp Ser Glu Val Glu Glu
        35                  40                  45

Ala Asp Gly Lys Lys Leu Ala Glu Ile Leu Val Asn Thr Ser Ser Glu
    50                  55                  60

Asn Trp Ile Arg Asn Ala Thr Val Asn Ile Leu Glu Met Asn Leu
65                  70                  75                  80

Thr Glu Leu Cys Lys Met Ala Lys Ala Glu Met Met Glu Asp Gly Gln
                85                  90                  95

Val Gln Glu Ile Asp Asn Pro Glu Leu Gly Asp Ala Glu Glu Asp Ser
            100                 105                 110

Glu Leu Ala Lys Pro Gly Glu Lys Glu Gly Trp Arg Asn Ser Met Glu
        115                 120                 125

Lys Gln Ser Leu Val Trp Lys Asn Thr Phe Trp Gln Gly Asp Ile Asp
    130                 135                 140
```

```
Asn Phe His Asp Asp Val Thr Leu Arg Asn Gln Arg Phe Ile Pro Phe
145                 150                 155                 160

Leu Asn Pro Arg Thr Pro Arg Lys Leu Thr Pro Tyr Thr Val Val Leu
            165                 170                 175

His Gly Pro Ala Gly Val Gly Lys Thr Thr Leu Ala Lys Lys Cys Met
        180                 185                 190

Leu Asp Trp Thr Asp Cys Asn Leu Ser Pro Thr Leu Arg Tyr Ala Phe
            195                 200                 205

Tyr Leu Ser Cys Lys Glu Leu Ser Arg Met Gly Pro Cys Ser Phe Ala
    210                 215                 220

Glu Leu Ile Ser Lys Asp Trp Pro Glu Leu Gln Asp Asp Ile Pro Ser
225                 230                 235                 240

Ile Leu Ala Gln Ala Gln Arg Ile Leu Phe Val Val Asp Gly Leu Asp
                245                 250                 255

Glu Leu Lys Val Pro Pro Gly Ala Leu Ile Gln Asp Ile Cys Gly Asp
            260                 265                 270

Trp Glu Lys Lys Lys Pro Val Pro Val Leu Leu Gly Ser Leu Leu Lys
            275                 280                 285

Arg Lys Met Leu Pro Arg Ala Ala Leu Leu Val Thr Thr Arg Pro Arg
    290                 295                 300

Ala Leu Arg Asp Leu Gln Leu Ala Gln Gln Pro Ile Tyr Val Arg
305                 310                 315                 320

Val Glu Gly Phe Leu Glu Glu Asp Arg Arg Ala Tyr Phe Leu Arg His
                325                 330                 335

Phe Gly Asp Glu Asp Gln Ala Met Arg Ala Phe Glu Leu Met Arg Ser
            340                 345                 350

Asn Ala Ala Leu Phe Gln Leu Gly Ser Ala Pro Ala Val Cys Trp Ile
                355                 360                 365

Val Cys Thr Thr Leu Lys Leu Gln Met Glu Lys Gly Glu Asp Pro Val
    370                 375                 380

Pro Thr Cys Leu Thr Arg Thr Gly Leu Phe Leu Arg Phe Leu Cys Ser
385                 390                 395                 400

Arg Phe Pro Gln Gly Ala Gln Leu Arg Gly Ala Leu Arg Thr Leu Ser
                405                 410                 415

Leu Leu Ala Ala Gln Gly Leu Trp Ala Gln Met Ser Val Phe His Arg
            420                 425                 430

Glu Asp Leu Glu Arg Leu Gly Val Gln Glu Ser Asp Leu Arg Leu Phe
            435                 440                 445

Leu Asp Gly Asp Ile Leu Arg Gln Asp Arg Val Ser Lys Gly Cys Tyr
450                 455                 460

Ser Phe Ile His Leu Ser Phe Gln Gln Phe Leu Thr Ala Leu Phe Tyr
465                 470                 475                 480

Ala Leu Glu Lys Glu Glu Gly Glu Asp Arg Asp Gly His Ala Trp Asp
            485                 490                 495

Ile Gly Asp Val Gln Lys Leu Leu Ser Gly Glu Glu Arg Leu Lys Asn
            500                 505                 510

Pro Asp Leu Ile Gln Val Gly His Phe Leu Phe Gly Leu Ala Asn Glu
            515                 520                 525

Lys Arg Ala Lys Glu Leu Glu Ala Thr Phe Gly Cys Arg Met Ser Pro
            530                 535                 540

Asp Ile Lys Gln Glu Leu Leu Gln Cys Lys Ala His Leu His Ala Asn
545                 550                 555                 560
```

-continued

```
Lys Pro Leu Ser Val Thr Asp Leu Lys Glu Val Leu Gly Cys Leu Tyr
                565                 570                 575
Glu Ser Gln Glu Glu Leu Ala Lys Val Val Ala Pro Phe Lys
            580                 585                 590
Glu Ile Ser Ile His Leu Thr Asn Thr Ser Glu Val Met His Cys Ser
            595                 600                 605
Phe Ser Leu Lys His Cys Gln Asp Leu Gln Lys Leu Ser Leu Gln Val
        610                 615                 620
Ala Lys Gly Val Phe Leu Glu Asn Tyr Met Asp Phe Glu Leu Asp Ile
625                 630                 635                 640
Glu Phe Glu Arg Cys Thr Tyr Leu Thr Ile Pro Asn Trp Ala Arg Gln
                645                 650                 655
Asp Leu Arg Ser Leu Arg Leu Trp Thr Asp Phe Cys Ser Leu Phe Ser
                660                 665                 670
Ser Asn Ser Asn Leu Lys Phe Leu Glu Val Lys Gln Ser Phe Leu Ser
            675                 680                 685
Asp Ser Ser Val Arg Ile Leu Cys Asp His Val Thr Arg Ser Thr Cys
690                 695                 700
His Leu Gln Lys Val Glu Ile Lys Asn Val Thr Pro Asp Thr Ala Tyr
705                 710                 715                 720
Arg Asp Phe Cys Leu Ala Phe Ile Gly Lys Lys Thr Leu Thr His Leu
                725                 730                 735
Thr Leu Ala Gly His Ile Glu Trp Glu Arg Thr Met Met Leu Met Leu
                740                 745                 750
Cys Asp Leu Leu Arg Asn His Lys Cys Asn Leu Gln Tyr Leu Arg Leu
            755                 760                 765
Gly Gly His Cys Ala Thr Pro Glu Gln Trp Ala Glu Phe Phe Tyr Val
770                 775                 780
Leu Lys Ala Asn Gln Ser Leu Lys His Leu Arg Leu Ser Ala Asn Val
785                 790                 795                 800
Leu Leu Asp Glu Gly Ala Met Leu Leu Tyr Lys Thr Met Thr Arg Pro
                805                 810                 815
Lys His Phe Leu Gln Met Leu Ser Leu Glu Asn Cys Arg Leu Thr Glu
                820                 825                 830
Ala Ser Cys Lys Asp Leu Ala Ala Val Leu Val Val Ser Lys Lys Leu
            835                 840                 845
Thr His Leu Cys Leu Ala Lys Asn Pro Ile Gly Asp Thr Gly Val Lys
850                 855                 860
Phe Leu Cys Glu Gly Leu Ser Tyr Pro Asp Cys Lys Leu Gln Thr Leu
865                 870                 875                 880
Val Leu Gln Gln Cys Ser Ile Thr Lys Leu Gly Cys Arg Tyr Leu Ser
                885                 890                 895
Glu Ala Leu Gln Glu Ala Cys Ser Leu Thr Asn Leu Asp Leu Ser Ile
                900                 905                 910
Asn Gln Ile Ala Arg Gly Leu Trp Ile Leu Cys Gln Ala Leu Glu Asn
            915                 920                 925
Pro Asn Cys Asn Leu Lys His Leu Arg Leu Lys Thr Tyr Glu Thr Asn
930                 935                 940
Leu Glu Ile Lys Lys Leu Leu Glu Glu Val Lys Glu Lys Asn Pro Lys
945                 950                 955                 960
Leu Thr Ile Asp Cys Asn Ala Ser Gly Ala Thr Ala Pro Pro Cys Cys
                965                 970                 975
Asp Phe Phe Cys
```

-continued

980

<210> SEQ ID NO 14
<211> LENGTH: 2940
<212> TYPE: DNA
<213> ORGANISM: Homo sapiens

<400> SEQUENCE: 14

| | | | | | |
|---|---|---|---|---|---|
| atgacatcgc | cccagctaga | gtggactctg | cagacccttc | tggagcagct | gaacgaggat | 60 |
| gaattaaaga | gtttcaaatc | ccttttatgg | gcttttcccc | tcgaagacgt | gctacagaag | 120 |
| accccatggt | ctgaggtgga | agaggctgat | ggcaagaaac | tggcagaaat | tctggtcaac | 180 |
| acctcctcag | aaaattggat | aaggaatgcg | actgtgaaca | tcttggaaga | gatgaatctc | 240 |
| acggaattgt | gtaagatggc | aaaggctgag | atgatggagg | acggacaggt | gcaagaaata | 300 |
| gataatcctg | agctgggaga | tgcagaagaa | gactcggagt | tagcaaagcc | aggtgaaaag | 360 |
| gaaggatgga | gaaattcaat | ggagaaacag | tcttttggtct | ggaagaacac | cttttggcaa | 420 |
| ggagacattg | acaatttcca | tgacgacgtc | actctgagaa | accaacggtt | cattccattc | 480 |
| ttgaatccca | gaacacccag | gaagctaaca | ccttacacgg | tggtgctgca | cggccccgca | 540 |
| ggcgtgggga | aaccacgct | ggccaaaaag | tgtatgctgg | actggacaga | ctgcaacctc | 600 |
| agcccgacgc | tcagatacgc | gttctacctc | agctgcaagg | agctcagccg | catgggcccc | 660 |
| tgcagttttg | cagagctgat | ctccaaagac | tggcctgaat | gcaggatga | cattccaagc | 720 |
| atcctagccc | aagcacagag | aatcctgttc | gtggtcgatg | ccttgatga | gctgaaagtc | 780 |
| ccacctgggg | cgctgatcca | ggacatctgc | ggggactggg | agaagaagaa | gccggtgccc | 840 |
| gtcctcctgg | ggagtttgct | gaagaggaag | atgttaccca | gggcagcctt | gctggtcacc | 900 |
| acgcggccca | gggcactgag | ggacctccag | ctcctggcgc | agcagccgat | ctacgtaagg | 960 |
| gtggagggct | tcctggagga | ggacaggagg | gcctatttcc | tgagacactt | tggagacgag | 1020 |
| gaccaagcca | tgcgtgcctt | tgagctaatg | aggagcaacg | cggccctgtt | ccagctgggc | 1080 |
| tcggccccg | cggtgtgctg | gattgtgtgc | acgactctga | agctgcagat | ggagaagggg | 1140 |
| gaggacccgg | tccccacctg | cctcacccgc | acggggctgt | tcctgcgttt | cctctgcagc | 1200 |
| cggttcccgc | agggcgcaca | gctgcggggc | gcgctgcgga | cgctgagcct | cctgccgcg | 1260 |
| cagggcctgt | gggcgcagat | gtccgtgttc | caccgagagg | acctggaaag | gctcggggtg | 1320 |
| caggagtccg | acctccgtct | gttcctggac | ggagacatcc | tccgccagga | cagagtctcc | 1380 |
| aaaggctgct | actccttcat | ccacctcagc | ttccagcagt | ttctcactgc | cctgttctac | 1440 |
| gccctggaga | aggaggaggg | ggaggacagg | gacggccacg | cctgggacat | cggggacgta | 1500 |
| cagaagctgc | tttccggaga | agaaagactc | aagaaccccg | acctgattca | agtaggacac | 1560 |
| ttcttattcg | gcctcgctaa | cgagaagaga | gccaaggagt | tggaggccac | ttttggctgc | 1620 |
| cggatgtcac | cggacatcaa | acaggaattg | ctgcaatgca | aagcacatct | tcatgcaaat | 1680 |
| aagcccttat | ccgtgaccga | cctgaaggag | gtcttgggct | gcctgtatga | gtctcaggag | 1740 |
| gaggagctgg | cgaaggtggt | ggtggccccg | ttcaaggaaa | tttctattca | cctgacaaat | 1800 |
| acttctgaag | tgatgcattg | ttccttcagc | ctgaagcatt | gtcaagactt | gcagaaactc | 1860 |
| tcactgcagg | tagcaaaggg | ggtgttcctg | gagaattaca | tggattttga | actggacatt | 1920 |
| gaatttgaaa | ggtgcactta | cctaaccatt | ccgaactggg | ctcggcagga | tcttcgctct | 1980 |
| cttcgcctct | ggacagattt | ctgctctctc | ttcagctcaa | acagcaacct | caagtttctg | 2040 |
| gaagtgaaac | aaagcttcct | gagtgactct | tctgtgcgga | ttctttgtga | ccacgtaacc | 2100 |

-continued

```
cgtagcacct gtcatctgca gaaagtggag attaaaaacg tcacccctga caccgcgtac    2160
cgggacttct gtcttgcttt cattgggaag aagaccctca cgcacctgac cctggcaggg    2220
cacatcgagt gggaacgcac gatgatgctg atgctgtgtg acctgctcag aaatcataaa    2280
tgcaacctgc agtacctgag gttgggaggt cactgtgcca ccccggagca gtgggctgaa    2340
ttcttctatg tcctcaaagc caaccagtcc ctgaagcacc tcgtctctc agccaatgtg    2400 ctcctggatg agggtgccat gttgctgtac aagaccatga cacgcccaaa acacttcctg    2460
cagatgttgt cgttggaaaa ctgtcgtctt acagaagcca gttgcaagga ccttgctgct    2520
gtcttggttg tcagcaagaa gctgacacac ctgtgcttgg ccaagaaccc cattggggat    2580 acagggtga agtttctgtg tgagggcttg agttaccctg attgtaaact gcagaccttg    2640
gtgttacagc aatgcagcat aaccaagctt ggctgtagat atctctcaga ggcgctccaa    2700
gaagcctgca gcctcacaaa cctggacttg agtatcaacc agatagctcg tggattgtgg    2760
attctctgtc aggcattaga gaatccaaac tgtaacctaa acacctacg gttgaagacc    2820 tatgaaacta atttggaaat caagaagctg ttggaggaag tgaaagaaaa gaatcccaag    2880
ctgactattg attgcaatgc ttccggggca acggcacctc cgtgctgtga ctttttttgc    2940
```

<210> SEQ ID NO 15
<211> LENGTH: 2628
<212> TYPE: DNA
<213> ORGANISM: Homo sapiens
<220> FEATURE:
<221> NAME/KEY: CDS
<222> LOCATION: (1)...(2625)

<400> SEQUENCE: 15

```
atg gca gaa tcg gat tct act gac ttt gac ctg ctg tgg tat cta gag      48
Met Ala Glu Ser Asp Ser Thr Asp Phe Asp Leu Leu Trp Tyr Leu Glu
 1               5                  10                  15 aat ctc agt gac aag gaa ttt cag agt ttt aag aag tat ctg gca cgc      96
Asn Leu Ser Asp Lys Glu Phe Gln Ser Phe Lys Lys Tyr Leu Ala Arg
             20                  25                  30 aag att ctt gat ttc aaa ctg cca cag ttt cca ctg ata cag atg aca     144
Lys Ile Leu Asp Phe Lys Leu Pro Gln Phe Pro Leu Ile Gln Met Thr
         35                  40                  45 aaa gaa gaa ctg gct aac gtg ttg cca atc tct tat gag gga cag tat     192
Lys Glu Glu Leu Ala Asn Val Leu Pro Ile Ser Tyr Glu Gly Gln Tyr
     50                  55                  60 ata tgg aat atg ctc ttc agc ata ttt tca atg atg cgt aag gaa gat     240
Ile Trp Asn Met Leu Phe Ser Ile Phe Ser Met Met Arg Lys Glu Asp
 65                  70                  75                  80 ctt tgt agg aag atc att ggc aga cga aac cat gtg ttc tac ata ctt     288
Leu Cys Arg Lys Ile Ile Gly Arg Arg Asn His Val Phe Tyr Ile Leu
                 85                  90                  95 caa tta gcc tat gat tct acc agc tat tat tca gca aac aat ctc aat     336
Gln Leu Ala Tyr Asp Ser Thr Ser Tyr Tyr Ser Ala Asn Asn Leu Asn
            100                 105                 110 gtg ttc ctg atg gga gag aga gca tct gga aaa act att gtt ata aat     384
Val Phe Leu Met Gly Glu Arg Ala Ser Gly Lys Thr Ile Val Ile Asn
        115                 120                 125 ctg gct gtg ttg agg tgg atc aag ggt gag atg tgg cag aac atg atc     432
Leu Ala Val Leu Arg Trp Ile Lys Gly Glu Met Trp Gln Asn Met Ile
    130                 135                 140 tcg tac gtc gtt cac ctc act tct cac gaa ata aac cag atg acc aac     480
Ser Tyr Val Val His Leu Thr Ser His Glu Ile Asn Gln Met Thr Asn
145                 150                 155                 160
```

```
                                     -continued agc agc ttg gct gag cta atc gcc aag gac tgg cct gac ggc cag gct      528
Ser Ser Leu Ala Glu Leu Ile Ala Lys Asp Trp Pro Asp Gly Gln Ala
            165                 170                 175 ccc att gca gac atc ctg tct gat ccc aag aaa ctc ctt ttc att ctc      576
Pro Ile Ala Asp Ile Leu Ser Asp Pro Lys Lys Leu Leu Phe Ile Leu
        180                 185                 190 gag gac ttg gac aac ata aga ttc gag tta aat gtc aat gaa agt gct      624
Glu Asp Leu Asp Asn Ile Arg Phe Glu Leu Asn Val Asn Glu Ser Ala
    195                 200                 205 ttg tgt agt aac agc acc cag aaa gtt ccc att cca gtt ctc ctg gtc      672
Leu Cys Ser Asn Ser Thr Gln Lys Val Pro Ile Pro Val Leu Leu Val
210                 215                 220 agt ttg ctg aag aga aaa atg gct cca ggc tgc tgg ttc ctc atc tcc      720
Ser Leu Leu Lys Arg Lys Met Ala Pro Gly Cys Trp Phe Leu Ile Ser
225                 230                 235                 240 tca agg ccc aca cgt ggg aat aat gta aaa acg ttc ttg aaa gag gta      768
Ser Arg Pro Thr Arg Gly Asn Asn Val Lys Thr Phe Leu Lys Glu Val
                245                 250                 255 gat tgc tgc acg acc ttg cag ctg tcg aat ggg aag agg gag ata tat      816
Asp Cys Cys Thr Thr Leu Gln Leu Ser Asn Gly Lys Arg Glu Ile Tyr
            260                 265                 270 ttt aac tct ttc ttt aaa gac cgc cag agg gcg tcg gca gcc ctc cag      864
Phe Asn Ser Phe Phe Lys Asp Arg Gln Arg Ala Ser Ala Ala Leu Gln
        275                 280                 285 ctt gta cat gag gat gaa ata ctc gtg ggt ctg tgc cga gtc gcc atc      912
Leu Val His Glu Asp Glu Ile Leu Val Gly Leu Cys Arg Val Ala Ile
    290                 295                 300 tta tgc tgg atc acg tgt act gtc ctg aag cgg cag atg gac aag ggg      960
Leu Cys Trp Ile Thr Cys Thr Val Leu Lys Arg Gln Met Asp Lys Gly
305                 310                 315                 320 cgt gac ttc cag ctc tgc tgc caa aca ccc act gat cta cat gcc cac     1008
Arg Asp Phe Gln Leu Cys Cys Gln Thr Pro Thr Asp Leu His Ala His
                325                 330                 335 ttt ctt gct gat gcg ttg aca tca gag gct gga ctt act gcc aat cag     1056
Phe Leu Ala Asp Ala Leu Thr Ser Glu Ala Gly Leu Thr Ala Asn Gln
            340                 345                 350 tat cac cta ggt ctc cta aaa cgt ctg tgt ttg ctg gct gca gga gga     1104
Tyr His Leu Gly Leu Leu Lys Arg Leu Cys Leu Leu Ala Ala Gly Gly
        355                 360                 365 ctg ttt ctg agc acc ctg aat ttc agt ggt gaa gac ctc aga tgt gtt     1152
Leu Phe Leu Ser Thr Leu Asn Phe Ser Gly Glu Asp Leu Arg Cys Val
    370                 375                 380 ggg ttt act gag gct gat gtc tct gtg ttg cag gcc gcg aat att ctt     1200
Gly Phe Thr Glu Ala Asp Val Ser Val Leu Gln Ala Ala Asn Ile Leu
385                 390                 395                 400 ttg ccg agc aac act cat aaa gac cgt tac aag ttc ata cac ttg aac     1248
Leu Pro Ser Asn Thr His Lys Asp Arg Tyr Lys Phe Ile His Leu Asn
                405                 410                 415 gtc cag gag ttt tgt aca gcc att gca ttt ctg atg gca gta ccc aac     1296
Val Gln Glu Phe Cys Thr Ala Ile Ala Phe Leu Met Ala Val Pro Asn
            420                 425                 430 tat ctg atc ccc tca ggc agc aga gag tat aaa gag aag aga gaa caa     1344
Tyr Leu Ile Pro Ser Gly Ser Arg Glu Tyr Lys Glu Lys Arg Glu Gln
        435                 440                 445 tac tct gac ttt aat caa gtg ttt act ttc att ttt ggt ctt cta aat     1392
Tyr Ser Asp Phe Asn Gln Val Phe Thr Phe Ile Phe Gly Leu Leu Asn
    450                 455                 460 gca aac agg aga aag att ctt gag aca tcc ttt gga tac cag cta ccg     1440
Ala Asn Arg Arg Lys Ile Leu Glu Thr Ser Phe Gly Tyr Gln Leu Pro
```

-continued

```
            465                 470                 475                 480
atg gta gac agc ttc aag tgg tac tcg gtg gga tac atg aaa cat ttg        1488
Met Val Asp Ser Phe Lys Trp Tyr Ser Val Gly Tyr Met Lys His Leu
                    485                 490                 495 gac cgt gac ccg gaa aag ttg acg cac cat atg cct ttg ttt tac tgt        1536
Asp Arg Asp Pro Glu Lys Leu Thr His His Met Pro Leu Phe Tyr Cys
500                 505                 510 ctc tat gag aat cgg gaa gaa gaa ttt gtg aag acg att gtg gat gct        1584
Leu Tyr Glu Asn Arg Glu Glu Glu Phe Val Lys Thr Ile Val Asp Ala
        515                 520                 525 ctc atg gag gtt aca gtt tac ctt caa tca gac aag gat atg atg gtc        1632
Leu Met Glu Val Thr Val Tyr Leu Gln Ser Asp Lys Asp Met Met Val
530                 535                 540 tca tta tac tgt ctg gat tac tgc tgt cac ctg agg aca ctt aag ttg        1680
Ser Leu Tyr Cys Leu Asp Tyr Cys Cys His Leu Arg Thr Leu Lys Leu
545                 550                 555                 560 agt gtt cag cgc atc ttt caa aac aaa gag cca ctt ata agg cca act        1728
Ser Val Gln Arg Ile Phe Gln Asn Lys Glu Pro Leu Ile Arg Pro Thr
                565                 570                 575 gct agt caa atg aag agc ctt gtc tac tgg aga gag atc tgc tct ctt        1776
Ala Ser Gln Met Lys Ser Leu Val Tyr Trp Arg Glu Ile Cys Ser Leu
        580                 585                 590 ttt tat aca atg gag agc ctc cgg gag ctg cat atc ttt gac aat gac        1824
Phe Tyr Thr Met Glu Ser Leu Arg Glu Leu His Ile Phe Asp Asn Asp
595                 600                 605 ctt aat ggt att tca gaa agg att ctg tct aaa gcc ctg gag cat tct        1872
Leu Asn Gly Ile Ser Glu Arg Ile Leu Ser Lys Ala Leu Glu His Ser
610                 615                 620 agc tgt aaa ctt cgc aca ctc aag ttg tcc tat gtc tcg act gct tct        1920
Ser Cys Lys Leu Arg Thr Leu Lys Leu Ser Tyr Val Ser Thr Ala Ser
625                 630                 635                 640 ggt ttt gaa gac tta ctc aag gct ttg gct cgt aat cgg agc ctg aca        1968
Gly Phe Glu Asp Leu Leu Lys Ala Leu Ala Arg Asn Arg Ser Leu Thr
                645                 650                 655 tac ctg agt atc aac tgt acg tcc att tcc cta aat atg ttt tca ctt        2016
Tyr Leu Ser Ile Asn Cys Thr Ser Ile Ser Leu Asn Met Phe Ser Leu
        660                 665                 670 ctg cat gac atc ctg cac gag ccc aca tgc caa ata agt cat ctg agc        2064
Leu His Asp Ile Leu His Glu Pro Thr Cys Gln Ile Ser His Leu Ser
675                 680                 685 ttg atg aaa tgt gat ttg cga gcc agc gaa tgc gaa gaa atc gcc tct        2112
Leu Met Lys Cys Asp Leu Arg Ala Ser Glu Cys Glu Glu Ile Ala Ser
690                 695                 700 ctc ctc atc agt ggc ggg agt ctg aga aaa ctg acc tta tcc agc aat        2160
Leu Leu Ile Ser Gly Gly Ser Leu Arg Lys Leu Thr Leu Ser Ser Asn
705                 710                 715                 720 ccg ctg agg agc gac ggg atg aac ata ctg tgt gat gcc ttg ctt cat        2208
Pro Leu Arg Ser Asp Gly Met Asn Ile Leu Cys Asp Ala Leu Leu His
                725                 730                 735 ccc aac tgc act ctt ata tca ctg gtt ctg tct ggc tgt ttc ttt agc        2256
Pro Asn Cys Thr Leu Ile Ser Leu Val Leu Ser Gly Cys Phe Phe Ser
        740                 745                 750 agc gat atc tgt caa tat att gcc ata gtt att gct act aat gaa aaa        2304
Ser Asp Ile Cys Gln Tyr Ile Ala Ile Val Ile Ala Thr Asn Glu Lys
755                 760                 765 ctg agg agc ctg gag att ggg agc aac aaa ata gaa gat gca gga atg        2352
Leu Arg Ser Leu Glu Ile Gly Ser Asn Lys Ile Glu Asp Ala Gly Met
770                 775                 780 cag ctg cta tgt ggt ggt ttg aga cat ccc aac tgc atg ttg gtg aat        2400
```

```
Gln Leu Leu Cys Gly Gly Leu Arg His Pro Asn Cys Met Leu Val Asn
785                 790                 795                 800 att ggg cta gaa gag tgc atg tta acc agt gcc tgt tgt cga tct ctt         2448
Ile Gly Leu Glu Glu Cys Met Leu Thr Ser Ala Cys Cys Arg Ser Leu
            805                 810                 815 gcc tct gtt ctt acc acc aac aaa aca cta gaa aga ctc aac ttg ctt         2496
Ala Ser Val Leu Thr Thr Asn Lys Thr Leu Glu Arg Leu Asn Leu Leu
820                 825                 830 caa aat cac ttg ggc aat gat gga gtt gca aaa ctt ctt gag agc ttg         2544
Gln Asn His Leu Gly Asn Asp Gly Val Ala Lys Leu Leu Glu Ser Leu
    835                 840                 845 atc agc cca gat tgt gta ctt aag gta gtt ggc ttg atg gct gct gag         2592
Ile Ser Pro Asp Cys Val Leu Lys Val Val Gly Leu Met Ala Ala Glu
850                 855                 860 aac atg gag tcc ctc att ccc agg cca gca cgc tga                         2628
Asn Met Glu Ser Leu Ile Pro Arg Pro Ala Arg
865                 870                 875
```

<210> SEQ ID NO 16
<211> LENGTH: 875
<212> TYPE: PRT
<213> ORGANISM: Homo sapiens

<400> SEQUENCE: 16

```
Met Ala Glu Ser Asp Ser Thr Asp Phe Asp Leu Leu Trp Tyr Leu Glu
1               5                   10                  15

Asn Leu Ser Asp Lys Glu Phe Gln Ser Phe Lys Lys Tyr Leu Ala Arg
                20                  25                  30

Lys Ile Leu Asp Phe Lys Leu Pro Gln Phe Pro Leu Ile Gln Met Thr
            35                  40                  45

Lys Glu Glu Leu Ala Asn Val Leu Pro Ile Ser Tyr Glu Gly Gln Tyr
        50                  55                  60

Ile Trp Asn Met Leu Phe Ser Ile Phe Ser Met Met Arg Lys Glu Asp
65              70                  75                  80

Leu Cys Arg Lys Ile Ile Gly Arg Arg Asn His Val Phe Tyr Ile Leu
                85                  90                  95

Gln Leu Ala Tyr Asp Ser Thr Ser Tyr Tyr Ser Ala Asn Asn Leu Asn
            100                 105                 110

Val Phe Leu Met Gly Glu Arg Ala Ser Gly Lys Thr Ile Val Ile Asn
        115                 120                 125

Leu Ala Val Leu Arg Trp Ile Lys Gly Glu Met Trp Gln Asn Met Ile
    130                 135                 140

Ser Tyr Val Val His Leu Thr Ser His Glu Ile Asn Gln Met Thr Asn
145                 150                 155                 160

Ser Ser Leu Ala Glu Leu Ile Ala Lys Asp Trp Pro Asp Gly Gln Ala
                165                 170                 175

Pro Ile Ala Asp Ile Leu Ser Asp Pro Lys Lys Leu Leu Phe Ile Leu
            180                 185                 190

Glu Asp Leu Asp Asn Ile Arg Phe Glu Leu Asn Val Asn Glu Ser Ala
        195                 200                 205

Leu Cys Ser Asn Ser Thr Gln Lys Val Pro Ile Pro Val Leu Leu Val
    210                 215                 220

Ser Leu Leu Lys Arg Lys Met Ala Pro Gly Cys Trp Phe Leu Ile Ser
225                 230                 235                 240

Ser Arg Pro Thr Arg Gly Asn Asn Val Lys Thr Phe Leu Lys Glu Val
                245                 250                 255
```

-continued

```
Asp Cys Cys Thr Thr Leu Gln Leu Ser Asn Gly Lys Arg Glu Ile Tyr
            260                 265                 270

Phe Asn Ser Phe Phe Lys Asp Arg Gln Arg Ala Ser Ala Ala Leu Gln
        275                 280                 285

Leu Val His Glu Asp Glu Ile Leu Val Gly Leu Cys Arg Val Ala Ile
        290                 295                 300

Leu Cys Trp Ile Thr Cys Thr Val Leu Lys Arg Gln Met Asp Lys Gly
305                 310                 315                 320

Arg Asp Phe Gln Leu Cys Cys Gln Thr Pro Thr Asp Leu His Ala His
                325                 330                 335

Phe Leu Ala Asp Ala Leu Thr Ser Glu Ala Gly Leu Thr Ala Asn Gln
                340                 345                 350

Tyr His Leu Gly Leu Leu Lys Arg Leu Cys Leu Leu Ala Ala Gly Gly
            355                 360                 365

Leu Phe Leu Ser Thr Leu Asn Phe Ser Gly Glu Asp Leu Arg Cys Val
370                 375                 380

Gly Phe Thr Glu Ala Asp Val Ser Val Leu Gln Ala Ala Asn Ile Leu
385                 390                 395                 400

Leu Pro Ser Asn Thr His Lys Asp Arg Tyr Lys Phe Ile His Leu Asn
                405                 410                 415

Val Gln Glu Phe Cys Thr Ala Ile Ala Phe Leu Met Ala Val Pro Asn
            420                 425                 430

Tyr Leu Ile Pro Ser Gly Ser Arg Glu Tyr Lys Glu Lys Arg Glu Gln
            435                 440                 445

Tyr Ser Asp Phe Asn Gln Val Phe Thr Phe Ile Phe Gly Leu Leu Asn
        450                 455                 460

Ala Asn Arg Arg Lys Ile Leu Glu Thr Ser Phe Gly Tyr Gln Leu Pro
465                 470                 475                 480

Met Val Asp Ser Phe Lys Trp Tyr Ser Val Gly Tyr Met Lys His Leu
                485                 490                 495

Asp Arg Asp Pro Glu Lys Leu Thr His His Met Pro Leu Phe Tyr Cys
            500                 505                 510

Leu Tyr Glu Asn Arg Glu Glu Phe Val Lys Thr Ile Val Asp Ala
        515                 520                 525

Leu Met Glu Val Thr Val Tyr Leu Gln Ser Asp Lys Asp Met Met Val
    530                 535                 540

Ser Leu Tyr Cys Leu Asp Tyr Cys Cys His Leu Arg Thr Leu Lys Leu
545                 550                 555                 560

Ser Val Gln Arg Ile Phe Gln Asn Lys Glu Pro Leu Ile Arg Pro Thr
                565                 570                 575

Ala Ser Gln Met Lys Ser Leu Val Tyr Trp Arg Glu Ile Cys Ser Leu
            580                 585                 590

Phe Tyr Thr Met Glu Ser Leu Arg Glu Leu His Ile Phe Asp Asn Asp
        595                 600                 605

Leu Asn Gly Ile Ser Glu Arg Ile Leu Ser Lys Ala Leu Glu His Ser
        610                 615                 620

Ser Cys Lys Leu Arg Thr Leu Lys Leu Ser Tyr Val Ser Thr Ala Ser
625                 630                 635                 640

Gly Phe Glu Asp Leu Leu Lys Ala Leu Ala Arg Asn Arg Ser Leu Thr
                645                 650                 655

Tyr Leu Ser Ile Asn Cys Thr Ser Ile Ser Leu Asn Met Phe Ser Leu
            660                 665                 670

Leu His Asp Ile Leu His Glu Pro Thr Cys Gln Ile Ser His Leu Ser
```

-continued

```
               675                 680                 685
Leu Met Lys Cys Asp Leu Arg Ala Ser Glu Cys Glu Ile Ala Ser
    690                 695                 700
Leu Leu Ile Ser Gly Gly Ser Leu Arg Lys Leu Thr Leu Ser Ser Asn
705                 710                 715                 720
Pro Leu Arg Ser Asp Gly Met Asn Ile Leu Cys Asp Ala Leu Leu His
                725                 730                 735
Pro Asn Cys Thr Leu Ile Ser Leu Val Leu Ser Gly Cys Phe Phe Ser
            740                 745                 750
Ser Asp Ile Cys Gln Tyr Ile Ala Ile Val Ile Ala Thr Asn Glu Lys
        755                 760                 765
Leu Arg Ser Leu Glu Ile Gly Ser Asn Lys Ile Glu Asp Ala Gly Met
    770                 775                 780
Gln Leu Leu Cys Gly Gly Leu Arg His Pro Asn Cys Met Leu Val Asn
785                 790                 795                 800
Ile Gly Leu Glu Glu Cys Met Leu Thr Ser Ala Cys Cys Arg Ser Leu
                805                 810                 815
Ala Ser Val Leu Thr Thr Asn Lys Thr Leu Glu Arg Leu Asn Leu Leu
            820                 825                 830
Gln Asn His Leu Gly Asn Asp Gly Val Ala Lys Leu Leu Glu Ser Leu
        835                 840                 845
Ile Ser Pro Asp Cys Val Leu Lys Val Val Gly Leu Met Ala Ala Glu
    850                 855                 860
Asn Met Glu Ser Leu Ile Pro Arg Pro Ala Arg
865                 870                 875

<210> SEQ ID NO 17
<211> LENGTH: 2625
<212> TYPE: DNA
<213> ORGANISM: Homo sapiens

<400> SEQUENCE: 17
atggcagaat cggattctac tgactttgac ctgctgtggt atctagagaa tctcagtgac      60
aaggaatttc agagttttaa gaagtatctg gcacgcaaga ttcttgattt caaactgcca     120
cagtttccac tgatacagat gacaaaagaa gaactggcta acgtgttgcc aatctcttat     180
gagggacagt atatatggaa tatgctcttc agcatatttt caatgatgcg taaggaagat     240
ctttgtagga agatcattgg cagacgaaac catgtgttct acatacttca attagcctat     300
gattctacca gctattattc agcaaacaat ctcaatgtgt tcctgatggg agagagagca     360
tctggaaaaa ctattgttat aaatctggct gtgttgaggt ggatcaaggg tgagatgtgg     420
cagaacatga tctcgtacgt cgttcacctc acttctcacg aaataaacca gatgaccaac     480
agcagcttgg ctgagctaat cgccaaggac tggcctgacg ccaggctcc cattgcagac     540 atcctgtctg atcccaagaa actccttttc attctcgagg acttggacaa cataagattc     600
gagttaaatg tcaatgaaag tgctttgtgt agtaacagca cccagaaagt tcccattcca     660
gttctcctgg tcagtttgct gaagagaaaa atggctccag ctgctggtt cctcatctcc     720 tcaaggccca cacgtgggaa taatgtaaaa acgttcttga agaggtaga ttgctgcacg     780 accttgcagc tgtcgaatgg gaagagggag atatatttta actctttctt taaagaccgc     840
cagagggcgt cggcagccct ccagcttgta catgaggatg aaatactcgt gggtctgtgc     900
cgagtcgcca tctatgctg atcacgtgt actgtcctga gcggcagat ggacaagggg     960 cgtgacttcc agctctgctg ccaaacaccc actgatctac atgcccactt tcttgctgat    1020
```

-continued

```
gcgttgacat cagaggctgg acttactgcc aatcagtatc acctaggtct cctaaaacgt    1080
ctgtgtttgc tggctgcagg aggactgttt ctgagcaccc tgaatttcag tggtgaagac    1140
ctcagatgtg ttgggtttac tgaggctgat gtctctgtgt gcaggccgc gaatattctt     1200 ttgccgagca acactcataa agaccgttac aagttcatac acttgaacgt ccaggagttt    1260
tgtacagcca ttgcatttct gatggcagta cccaactatc tgatcccctc aggcagcaga   1320
gagtataaag agaagagaga acaatactct gactttaatc aagtgtttac tttcattttt    1380
ggtcttctaa atgcaaacag gagaaagatt cttgagacat cctttggata ccagctaccg    1440
atggtagaca gcttcaagtg gtactcggtg ggatacatga acatttgga ccgtgacccg     1500 gaaaagttga cgcaccatat gcctttgttt tactgtctct atgagaatcg ggaagaagaa    1560
tttgtgaaga cgattgtgga tgctctcatg gaggttacag tttaccttca atcagacaag    1620
gatatgatgg tctcattata ctgtctggat tactgctgtc acctgaggac acttaagttg    1680
agtgttcagc gcatctttca aaacaaagag ccacttataa ggccaactgc tagtcaaatg    1740
aagagccttg tctactggag agagatctgc tctcttttt atacaatgga gagcctccgg     1800
gagctgcata tctttgacaa tgaccttaat ggtatttcag aaaggattct gtctaaagcc    1860
ctggagcatt ctagctgtaa acttcgcaca ctcaagttgt cctatgtctc gactgcttct    1920
ggttttgaag acttactcaa ggctttggct cgtaatcgga gcctgacata cctgagtatc    1980
aactgtacgt ccatttccct aaatatgttt tcacttctgc atgacatcct gcacgagccc    2040
acatgccaaa taagtcatct gagcttgatg aaatgtgatt tgcgagccag cgaatgcgaa    2100
gaaatcgcct ctctcctcat cagtggcggg agtctgagaa aactgacctt atccagcaat    2160
ccgctgagga gcgacgggat gaacatactg tgtgatgcct tgcttcatcc caactgcact    2220
cttatatcac tggttctgtc tggctgtttc tttagcagcg atatctgtca atatattgcc    2280
atagttattg ctactaatga aaaactgagg agcctggaga ttgggagcaa caaaatagaa    2340
gatgcaggaa tgcagctgct atgtggtggt ttgagacatc ccaactgcat gttggtgaat    2400
attgggctag aagagtgcat gttaaccagt gcctgctgtc gatctcttgc ctctgttctt    2460
accaccaaca aaacactaga aagactcaac ttgcttcaaa atcacttggg caatgatgga    2520
gttgcaaaac ttcttgagag cttgatcagc ccagattgtg tacttaaggt agttggcttg    2580
atggctgctg agaacatgga gtccctcatt cccaggccag cacgc                    2625
```

<210> SEQ ID NO 18
<211> LENGTH: 3051
<212> TYPE: DNA
<213> ORGANISM: Homo sapiens
<220> FEATURE:
<221> NAME/KEY: CDS
<222> LOCATION: (1)...(3048)

<400> SEQUENCE: 18

```
atg tat gag ttt tat att cac aaa ggt tat gat gat gtg tct tca gac       48
Met Tyr Glu Phe Tyr Ile His Lys Gly Tyr Asp Asp Val Ser Ser Asp
1               5                   10                  15 aac agc aga gag aaa atc aaa ggt gaa ccc tct gaa tgt gag ttg ggg       96
Asn Ser Arg Glu Lys Ile Lys Gly Glu Pro Ser Glu Cys Glu Leu Gly
                20                  25                  30 cac ttc ccg cgt atc ccc tgg gca aac ttg aga gct gcc gac cct ttg      144
His Phe Pro Arg Ile Pro Trp Ala Asn Leu Arg Ala Ala Asp Pro Leu
            35                  40                  45 aat ctg tcc ttt ctt ttg gat gaa cac ttc cca aaa ggt cag gca tgg      192
```

```
                Asn Leu Ser Phe Leu Leu Asp Glu His Phe Pro Lys Gly Gln Ala Trp
                    50                  55                  60 aaa gtg gtc ctc ggc atc ttc cag aca atg aat ctg acc tca ctg tgt          240
Lys Val Val Leu Gly Ile Phe Gln Thr Met Asn Leu Thr Ser Leu Cys
 65              70                  75                  80 gag aaa gtt aga gcc gag atg aaa gag aat gtg cag acc caa gag ctg          288
Glu Lys Val Arg Ala Glu Met Lys Glu Asn Val Gln Thr Gln Glu Leu
                 85                  90                  95 caa gat cca acc cag gaa gat cta gag atg cta gaa gca gca gca ggg          336
Gln Asp Pro Thr Gln Glu Asp Leu Glu Met Leu Glu Ala Ala Ala Gly
            100                 105                 110 aat atg cag acc cag gga tgc caa gat cca aac caa gaa gaa cta gac          384
Asn Met Gln Thr Gln Gly Cys Gln Asp Pro Asn Gln Glu Glu Leu Asp
        115                 120                 125 gag cta gaa gaa gaa aca ggg aat gta cag gcc cag gga tgc caa gat          432
Glu Leu Glu Glu Glu Thr Gly Asn Val Gln Ala Gln Gly Cys Gln Asp
    130                 135                 140 cca aac caa gaa gaa cca gag atg cta gag gaa gca gac cac aga aga          480
Pro Asn Gln Glu Glu Pro Glu Met Leu Glu Glu Ala Asp His Arg Arg
145                 150                 155                 160 aaa tac aga gag aac atg aag gct gaa cta ctg gag aca tgg gac aac          528
Lys Tyr Arg Glu Asn Met Lys Ala Glu Leu Leu Glu Thr Trp Asp Asn
                165                 170                 175 atc agt tgg cct aaa gac cac gta tat atc cgt aat aca tca aag gac          576
Ile Ser Trp Pro Lys Asp His Val Tyr Ile Arg Asn Thr Ser Lys Asp
            180                 185                 190 gaa cat gag gaa ctg cag cgc cta ctg gat cct aat agg act aga gcc          624
Glu His Glu Glu Leu Gln Arg Leu Leu Asp Pro Asn Arg Thr Arg Ala
        195                 200                 205 cag gcc cag acg ata gtc ttg gtg ggg agg gca ggg gtt ggg aag acc          672
Gln Ala Gln Thr Ile Val Leu Val Gly Arg Ala Gly Val Gly Lys Thr
    210                 215                 220 acc ttg gca atg cgg gct atg ctg cac tgg gca aat gga gtt ctc ttt          720
Thr Leu Ala Met Arg Ala Met Leu His Trp Ala Asn Gly Val Leu Phe
225                 230                 235                 240 cag caa agg ttc tcc tat gtt ttc tat ctc agc tgc cat aaa ata agg          768
Gln Gln Arg Phe Ser Tyr Val Phe Tyr Leu Ser Cys His Lys Ile Arg
                245                 250                 255 tac atg aag gaa act acc ttt gct gaa ttg att tct ttg gat tgg ccc          816
Tyr Met Lys Glu Thr Thr Phe Ala Glu Leu Ile Ser Leu Asp Trp Pro
            260                 265                 270 gat ttt gat gcc ccc att gaa gag ttc atg tct caa cca gag aag ctc          864
Asp Phe Asp Ala Pro Ile Glu Glu Phe Met Ser Gln Pro Glu Lys Leu
        275                 280                 285 ctg ttt att att gat ggc ttt gag gaa ata atc ata tct gag tca cgc          912
Leu Phe Ile Ile Asp Gly Phe Glu Glu Ile Ile Ile Ser Glu Ser Arg
    290                 295                 300 tct gag agc ttg gat gat ggc tcg cca tgt aca gac tgg tac cag gag          960
Ser Glu Ser Leu Asp Asp Gly Ser Pro Cys Thr Asp Trp Tyr Gln Glu
305                 310                 315                 320 ctc cca gtg acc aaa atc cta cac agc ttg ttg aag aaa gaa ttg gtt         1008
Leu Pro Val Thr Lys Ile Leu His Ser Leu Leu Lys Lys Glu Leu Val
                325                 330                 335 ccc ctg gct acc tta ctg atc acg atc aag acc tgg ttt gtg aga gat         1056
Pro Leu Ala Thr Leu Leu Ile Thr Ile Lys Thr Trp Phe Val Arg Asp
            340                 345                 350 ctt aag gcc tca tta gtg aat cca tgc ttt gta caa att aca ggg ttc         1104
Leu Lys Ala Ser Leu Val Asn Pro Cys Phe Val Gln Ile Thr Gly Phe
        355                 360                 365
```

-continued

| | | |
|---|---|---|
| aca ggg gac gac cta cgg gta tat ttc atg aga cac ttt gat gac tca<br>Thr Gly Asp Asp Leu Arg Val Tyr Phe Met Arg His Phe Asp Asp Ser<br>370                              375                         380 | 1152 |

```
aca ggg gac gac cta cgg gta tat ttc atg aga cac ttt gat gac tca      1152
Thr Gly Asp Asp Leu Arg Val Tyr Phe Met Arg His Phe Asp Asp Ser
    370                 375                 380 agt gaa gtt gag aaa atc ctg cag cag cta aga aaa aac gaa act ctc      1200
Ser Glu Val Glu Lys Ile Leu Gln Gln Leu Arg Lys Asn Glu Thr Leu
385                 390                 395                 400 ttt cat tcc tgc agt gcc ccc atg gtg tgt tgg act gta tgt tcc tgt      1248
Phe His Ser Cys Ser Ala Pro Met Val Cys Trp Thr Val Cys Ser Cys
                405                 410                 415 ctg aag cag ccg aag gtg agg tat tac gat ctc cag tca atc act cag      1296
Leu Lys Gln Pro Lys Val Arg Tyr Tyr Asp Leu Gln Ser Ile Thr Gln
            420                 425                 430 act acc acc agt ctg tat gcc tat ttt ttc tcc aac ttg ttc tcc aca      1344
Thr Thr Thr Ser Leu Tyr Ala Tyr Phe Phe Ser Asn Leu Phe Ser Thr
        435                 440                 445 gca gag gta gat ttg gca gat gac agc tgg cca gga caa tgg agg gcc      1392
Ala Glu Val Asp Leu Ala Asp Asp Ser Trp Pro Gly Gln Trp Arg Ala
450                 455                 460 ctc tgc agc ctg gcc ata gaa ggg ctg tgg tct atg aac ttc aca ttt      1440
Leu Cys Ser Leu Ala Ile Glu Gly Leu Trp Ser Met Asn Phe Thr Phe
465                 470                 475                 480 aac aaa gaa gac act gag att gag ggc ctg gaa gtg cct ttc att gat      1488
Asn Lys Glu Asp Thr Glu Ile Glu Gly Leu Glu Val Pro Phe Ile Asp
                485                 490                 495 tct ctc tac gag ttc aat att ctt caa aag atc aat gac tgt ggg ggt      1536
Ser Leu Tyr Glu Phe Asn Ile Leu Gln Lys Ile Asn Asp Cys Gly Gly
            500                 505                 510 tgc act act ttc acc cac cta agt ttc cag gag ttt ttt gca gcc atg      1584
Cys Thr Thr Phe Thr His Leu Ser Phe Gln Glu Phe Phe Ala Ala Met
        515                 520                 525 tcc ttt gtg cta gag gaa cct aga gaa ttc cct ccc cat tcc aca aag      1632
Ser Phe Val Leu Glu Glu Pro Arg Glu Phe Pro Pro His Ser Thr Lys
530                 535                 540 cca caa gag atg aag atg tta ctg caa cac gtc ttg ctt gac aaa gaa      1680
Pro Gln Glu Met Lys Met Leu Leu Gln His Val Leu Leu Asp Lys Glu
545                 550                 555                 560 gcc tac tgg act cca gtg gtt ctg ttc ttc ttt ggt ctt tta aat aaa      1728
Ala Tyr Trp Thr Pro Val Val Leu Phe Phe Phe Gly Leu Leu Asn Lys
                565                 570                 575 aac ata gca aga gaa ctg gaa gat act ttg cat tgt aaa ata tct ccc      1776
Asn Ile Ala Arg Glu Leu Glu Asp Thr Leu His Cys Lys Ile Ser Pro
            580                 585                 590 agg gta atg gag gaa tta tta aag tgg gga gaa gag tta ggt aag gct      1824
Arg Val Met Glu Glu Leu Leu Lys Trp Gly Glu Glu Leu Gly Lys Ala
        595                 600                 605 gaa agt gcc tct ctc caa ttt cac att cta cga ctt ttt cac tgc cta      1872
Glu Ser Ala Ser Leu Gln Phe His Ile Leu Arg Leu Phe His Cys Leu
610                 615                 620 cac gag tcc cag gag gaa gac ttc aca aag aag atg ttg ggt cgt atc      1920
His Glu Ser Gln Glu Glu Asp Phe Thr Lys Lys Met Leu Gly Arg Ile
625                 630                 635                 640 ttt gaa gtt gac ctt aat att ttg gag gac gaa gaa ctc caa gct tct      1968
Phe Glu Val Asp Leu Asn Ile Leu Glu Asp Glu Glu Leu Gln Ala Ser
                645                 650                 655 tca ttt tgc cta aag cac tgt aaa agg tta aat aag cta agg ctt tct      2016
Ser Phe Cys Leu Lys His Cys Lys Arg Leu Asn Lys Leu Arg Leu Ser
            660                 665                 670 gtt agc agt cac atc ctt gaa agg gac ttg gaa att ctg gag tgc aaa      2064
Val Ser Ser His Ile Leu Glu Arg Asp Leu Glu Ile Leu Glu Cys Lys
        675                 680                 685
```

```
tcg gta act cct gag tgg gtt ctg cag gac ctc att att gcc ctt cag     2112
Ser Val Thr Pro Glu Trp Val Leu Gln Asp Leu Ile Ile Ala Leu Gln
        690                 695                 700 ggt aac agc aag ctg acc cat ctg aac ttc agc tct aac aag ctg gga     2160
Gly Asn Ser Lys Leu Thr His Leu Asn Phe Ser Ser Asn Lys Leu Gly
705                 710                 715                 720 atg act gtc ccc ctg att ctt aaa gct ttg aga cac tca gct tgc aac     2208
Met Thr Val Pro Leu Ile Leu Lys Ala Leu Arg His Ser Ala Cys Asn
                725                 730                 735 ctc aag tat ctg tgc ctg gag aaa tgc aac ttg tcg gca gcc agc tgt     2256
Leu Lys Tyr Leu Cys Leu Glu Lys Cys Asn Leu Ser Ala Ala Ser Cys
            740                 745                 750 cag gac cta gcc ttg ttt ctc acc agc atc caa cac gta act cga ttg     2304
Gln Asp Leu Ala Leu Phe Leu Thr Ser Ile Gln His Val Thr Arg Leu
        755                 760                 765 tgc ctg gga ttt aat cgg ctc caa gat gat ggc ata aag cta ttg tgt     2352
Cys Leu Gly Phe Asn Arg Leu Gln Asp Asp Gly Ile Lys Leu Leu Cys
    770                 775                 780 gcg gcc ctg act cac ccc aag tgt gcc tta gag aga ctg gag ctc tgg     2400
Ala Ala Leu Thr His Pro Lys Cys Ala Leu Glu Arg Leu Glu Leu Trp
785                 790                 795                 800 ttt tgc cag ctg gca gca ccc gct tgc aag cac ttg tca gat gct ctc     2448
Phe Cys Gln Leu Ala Ala Pro Ala Cys Lys His Leu Ser Asp Ala Leu
                805                 810                 815 ctg cag aac agg agc ctg aca cac ctg aat ctg agc aag aac agc ctg     2496
Leu Gln Asn Arg Ser Leu Thr His Leu Asn Leu Ser Lys Asn Ser Leu
            820                 825                 830 aga gac gag gga gtc aag ttc ctg tgt gag gcc ttg ggt cgc cca gat     2544
Arg Asp Glu Gly Val Lys Phe Leu Cys Glu Ala Leu Gly Arg Pro Asp
        835                 840                 845 ggt aac ctg cag agc ctg aat ttg tca ggt tgt tct ttc aca aga gag     2592
Gly Asn Leu Gln Ser Leu Asn Leu Ser Gly Cys Ser Phe Thr Arg Glu
    850                 855                 860 ggc tgt gga gag ctg gct aat gcc ctc agc cat aat cat aat gtg aaa     2640
Gly Cys Gly Glu Leu Ala Asn Ala Leu Ser His Asn His Asn Val Lys
865                 870                 875                 880 atc ttg gat ttg gga gaa aat gat ctt cag gat gat gga gtg aag cta     2688
Ile Leu Asp Leu Gly Glu Asn Asp Leu Gln Asp Asp Gly Val Lys Leu
                885                 890                 895 ctg tgt gag gct ctg aaa cca cat cgt gca ttg cac aca ctt ggg ttg     2736
Leu Cys Glu Ala Leu Lys Pro His Arg Ala Leu His Thr Leu Gly Leu
            900                 905                 910 gcg aaa tgc aat ctg aca act gct tgc tgc cag cat ctc ttc tct gtt     2784
Ala Lys Cys Asn Leu Thr Thr Ala Cys Cys Gln His Leu Phe Ser Val
        915                 920                 925 ctc agc agc agt aag agc ctg gtc aat ctg aac ctt cta ggc aat gaa     2832
Leu Ser Ser Ser Lys Ser Leu Val Asn Leu Asn Leu Leu Gly Asn Glu
    930                 935                 940 ttg gat act gat ggt gtc aag atg cta tcc tct atc ctc gtg tct tta     2880
Leu Asp Thr Asp Gly Val Lys Met Leu Ser Ser Ile Leu Val Ser Leu
945                 950                 955                 960 gat tta gac ccc ttg ttc ttc gag cca ctt ccg gac tgc caa att aga     2928
Asp Leu Asp Pro Leu Phe Phe Glu Pro Leu Pro Asp Cys Gln Ile Arg
                965                 970                 975 ctt cag tta aaa gac ttt agc tcc tgg ccc ccc gtc agc ccc tcc ggt     2976
Leu Gln Leu Lys Asp Phe Ser Ser Trp Pro Pro Val Ser Pro Ser Gly
            980                 985                 990 gat gtg cag gac atg gag gta gaa tgg gac cct gtt tac agg aat aat     3024
Asp Val Gln Asp Met Glu Val Glu Trp Asp Pro Val Tyr Arg Asn Asn
```

```
                     995                  1000                 1005
att cag gtt aat aca aaa cca tcg taa                                      3051
Ile Gln Val Asn Thr Lys Pro Ser
    1010                1015

<210> SEQ ID NO 19
<211> LENGTH: 1016
<212> TYPE: PRT
<213> ORGANISM: Homo sapiens

<400> SEQUENCE: 19

Met Tyr Glu Phe Tyr Ile His Lys Gly Tyr Asp Asp Val Ser Ser Asp
  1               5                  10                  15

Asn Ser Arg Glu Lys Ile Lys Gly Glu Pro Ser Glu Cys Glu Leu Gly
                 20                  25                  30

His Phe Pro Arg Ile Pro Trp Ala Asn Leu Arg Ala Ala Asp Pro Leu
             35                  40                  45

Asn Leu Ser Phe Leu Leu Asp Glu His Phe Pro Lys Gly Gln Ala Trp
         50                  55                  60

Lys Val Leu Gly Ile Phe Gln Thr Met Asn Leu Thr Ser Leu Cys
 65                  70                  75                  80

Glu Lys Val Arg Ala Glu Met Lys Glu Asn Val Gln Thr Gln Glu Leu
                 85                  90                  95

Gln Asp Pro Thr Gln Glu Asp Leu Glu Met Leu Glu Ala Ala Ala Gly
            100                 105                 110

Asn Met Gln Thr Gln Gly Cys Gln Asp Pro Asn Gln Glu Glu Leu Asp
        115                 120                 125

Glu Leu Glu Glu Glu Thr Gly Asn Val Gln Ala Gln Gly Cys Gln Asp
    130                 135                 140

Pro Asn Gln Glu Glu Pro Glu Met Leu Glu Glu Ala Asp His Arg Arg
145                 150                 155                 160

Lys Tyr Arg Glu Asn Met Lys Ala Glu Leu Glu Thr Trp Asp Asn
                165                 170                 175

Ile Ser Trp Pro Lys Asp His Val Tyr Ile Arg Asn Thr Ser Lys Asp
            180                 185                 190

Glu His Glu Glu Leu Gln Arg Leu Leu Asp Pro Asn Arg Thr Arg Ala
        195                 200                 205

Gln Ala Gln Thr Ile Val Leu Val Gly Arg Ala Gly Val Gly Lys Thr
    210                 215                 220

Thr Leu Ala Met Arg Ala Met Leu His Trp Ala Asn Gly Val Leu Phe
225                 230                 235                 240

Gln Gln Arg Phe Ser Tyr Val Phe Tyr Leu Ser Cys His Lys Ile Arg
                245                 250                 255

Tyr Met Lys Glu Thr Thr Phe Ala Glu Leu Ile Ser Leu Asp Trp Pro
            260                 265                 270

Asp Phe Asp Ala Pro Ile Glu Phe Met Ser Gln Pro Glu Lys Leu
        275                 280                 285

Leu Phe Ile Ile Asp Gly Phe Glu Glu Ile Ile Ser Glu Ser Arg
    290                 295                 300

Ser Glu Ser Leu Asp Asp Gly Ser Pro Cys Thr Asp Trp Tyr Gln Glu
305                 310                 315                 320

Leu Pro Val Thr Lys Ile Leu His Ser Leu Lys Lys Glu Leu Val
                325                 330                 335

Pro Leu Ala Thr Leu Leu Ile Thr Ile Lys Thr Trp Phe Val Arg Asp
            340                 345                 350
```

```
Leu Lys Ala Ser Leu Val Asn Pro Cys Phe Val Gln Ile Thr Gly Phe
        355                 360                 365

Thr Gly Asp Asp Leu Arg Val Tyr Phe Met Arg His Phe Asp Asp Ser
    370                 375                 380

Ser Glu Val Glu Lys Ile Leu Gln Gln Leu Arg Lys Asn Glu Thr Leu
385                 390                 395                 400

Phe His Ser Cys Ser Ala Pro Met Val Cys Trp Thr Val Cys Ser Cys
                405                 410                 415

Leu Lys Gln Pro Lys Val Arg Tyr Tyr Asp Leu Gln Ser Ile Thr Gln
            420                 425                 430

Thr Thr Thr Ser Leu Tyr Ala Tyr Phe Phe Ser Asn Leu Phe Ser Thr
        435                 440                 445

Ala Glu Val Asp Leu Ala Asp Asp Ser Trp Pro Gly Gln Trp Arg Ala
    450                 455                 460

Leu Cys Ser Leu Ala Ile Glu Gly Leu Trp Ser Met Asn Phe Thr Phe
465                 470                 475                 480

Asn Lys Glu Asp Thr Glu Ile Glu Gly Leu Glu Val Pro Phe Ile Asp
                485                 490                 495

Ser Leu Tyr Glu Phe Asn Ile Leu Gln Lys Ile Asn Asp Cys Gly Gly
            500                 505                 510

Cys Thr Thr Phe Thr His Leu Ser Phe Gln Glu Phe Ala Ala Met
        515                 520                 525

Ser Phe Val Leu Glu Glu Pro Arg Glu Phe Pro Pro His Ser Thr Lys
530                 535                 540

Pro Gln Glu Met Lys Met Leu Leu Gln His Val Leu Leu Asp Lys Glu
545                 550                 555                 560

Ala Tyr Trp Thr Pro Val Val Leu Phe Phe Gly Leu Leu Asn Lys
                565                 570                 575

Asn Ile Ala Arg Glu Leu Glu Asp Thr Leu His Cys Lys Ile Ser Pro
            580                 585                 590

Arg Val Met Glu Glu Leu Leu Lys Trp Gly Glu Glu Leu Gly Lys Ala
        595                 600                 605

Glu Ser Ala Ser Leu Gln Phe His Ile Leu Arg Leu Phe His Cys Leu
    610                 615                 620

His Glu Ser Gln Glu Glu Asp Phe Thr Lys Lys Met Leu Gly Arg Ile
625                 630                 635                 640

Phe Glu Val Asp Leu Asn Ile Leu Glu Asp Glu Glu Leu Gln Ala Ser
                645                 650                 655

Ser Phe Cys Leu Lys His Cys Lys Arg Leu Asn Lys Leu Arg Leu Ser
            660                 665                 670

Val Ser Ser His Ile Leu Glu Arg Asp Leu Glu Ile Leu Glu Cys Lys
        675                 680                 685

Ser Val Thr Pro Glu Trp Val Leu Gln Asp Leu Ile Ile Ala Leu Gln
    690                 695                 700

Gly Asn Ser Lys Leu Thr His Leu Asn Phe Ser Ser Asn Lys Leu Gly
705                 710                 715                 720

Met Thr Val Pro Leu Ile Leu Lys Ala Leu Arg His Ser Ala Cys Asn
                725                 730                 735

Leu Lys Tyr Leu Cys Leu Glu Lys Cys Asn Leu Ser Ala Ala Ser Cys
            740                 745                 750

Gln Asp Leu Ala Leu Phe Leu Thr Ser Ile Gln His Val Thr Arg Leu
        755                 760                 765
```

```
Cys Leu Gly Phe Asn Arg Leu Gln Asp Asp Gly Ile Lys Leu Leu Cys
    770                 775                 780
Ala Ala Leu Thr His Pro Lys Cys Ala Leu Glu Arg Leu Glu Leu Trp
785                 790                 795                 800
Phe Cys Gln Leu Ala Ala Pro Ala Cys Lys His Leu Ser Asp Ala Leu
                    805                 810                 815
Leu Gln Asn Arg Ser Leu Thr His Leu Asn Leu Ser Lys Asn Ser Leu
            820                 825                 830
Arg Asp Glu Gly Val Lys Phe Leu Cys Glu Ala Leu Gly Arg Pro Asp
        835                 840                 845
Gly Asn Leu Gln Ser Leu Asn Leu Ser Gly Cys Ser Phe Thr Arg Glu
    850                 855                 860
Gly Cys Gly Glu Leu Ala Asn Ala Leu Ser His Asn His Asn Val Lys
865                 870                 875                 880
Ile Leu Asp Leu Gly Glu Asn Asp Leu Gln Asp Gly Val Lys Leu
                    885                 890                 895
Leu Cys Glu Ala Leu Lys Pro His Arg Ala Leu His Thr Leu Gly Leu
            900                 905                 910
Ala Lys Cys Asn Leu Thr Thr Ala Cys Cys Gln His Leu Phe Ser Val
        915                 920                 925
Leu Ser Ser Ser Lys Ser Leu Val Asn Leu Asn Leu Leu Gly Asn Glu
    930                 935                 940
Leu Asp Thr Asp Gly Val Lys Met Leu Ser Ser Ile Leu Val Ser Leu
945                 950                 955                 960
Asp Leu Asp Pro Leu Phe Glu Pro Leu Pro Asp Cys Gln Ile Arg
                    965                 970                 975
Leu Gln Leu Lys Asp Phe Ser Ser Trp Pro Val Ser Pro Ser Gly
            980                 985                 990
Asp Val Gln Asp Met Glu Val Glu Trp Asp Pro Val Tyr Arg Asn Asn
        995                 1000                1005
Ile Gln Val Asn Thr Lys Pro Ser
    1010                1015

<210> SEQ ID NO 20
<211> LENGTH: 3048
<212> TYPE: DNA
<213> ORGANISM: Homo sapiens

<400> SEQUENCE: 20
atgtatgagt tttatattca caaaggttat gatgatgtgt cttcagacaa cagcagagag      60
aaaatcaaag gtgaaccctc tgaatgtgag ttggggcact tcccgcgtat ccctgggca     120 aacttgagag ctgccgaccc tttgaatctg tcctttcttt tggatgaaca cttcccaaaa     180
ggtcaggcat ggaaagtggt cctcggcatc ttccagacaa tgaatctgac ctcactgtgt     240
gagaaagtta gagccgagat gaagagaat gtgcagaccc aagagctgca agatccaacc     300
caggaagatc tagagatgct agaagcagca gcagggaata tgcagaccca gggatgccaa     360
gatccaaacc aagaagaact agacgagcta aagaagaaa cagggaatgt acaggcccag     420
ggatgccaag atccaaacca agaagaacca gagatgctag aggaagcaga ccacagaaga     480
aaatacagag agaacatgaa ggctgaacta ctggagacat gggacaacat cagttggcct     540
aaagaccacg tatatatccg taatacatca aaggacgaac atgaggaact gcagcgccta     600
ctggatccta ataggactag agcccaggcc cagacgatag tcttggtggg gagggcaggg     660
gttgggaaga ccaccttggc aatgcgggct atgctgcact gggcaaatgg agttctcttt     720
```

```
cagcaaaggt tctcctatgt tttctatctc agctgccata aaataaggta catgaaggaa    780
actacctttg ctgaattgat ttctttggat tggcccgatt ttgatgcccc cattgaagag    840
ttcatgtctc aaccagagaa gctcctgttt attattgatg ctttgagga ataatcata     900
tctgagtcac gctctgagag cttggatgat ggctcgccat gtacagactg gtaccaggag    960
ctcccagtga ccaaaatcct acacagcttg ttgaagaaag aattggttcc cctggctacc   1020
ttactgatca cgatcaagac ctggtttgtg agagatctta aggcctcatt agtgaatcca   1080
tgctttgtac aaattacagg gttcacaggg gacgacctac gggtatattt catgagacac   1140
tttgatgact caagtgaagt tgagaaaatc ctgcagcagc taagaaaaaa cgaaactctc   1200
tttcattcct gcagtgcccc catggtgtgt tggactgtat gttcctgtct gaagcagccg   1260
aaggtgaggt attacgatct ccagtcaatc actcagacta ccaccagtct gtatgcctat   1320
tttttctcca acttgttctc cacagcagag gtagatttgg cagatgacag ctggccagga   1380
caatggaggg ccctctgcag cctggccata aagggctgt ggtctatgaa cttcacattt    1440
aacaaagaag acactgagat tgagggcctg gaagtgcctt tcattgattc tctctacgag   1500
ttcaatattc ttcaaaagat caatgactgt gggggttgca ctactttcac ccacctaagt   1560
ttccaggagt tttttgcagc catgtccttt gtgctagagg aacctagaga attccctccc   1620
cattccacaa agccacaaga gatgaagatg ttactgcaac acgtcttgct tgacaaagaa   1680
gcctactgga ctccagtggt tctgttcttc tttggtcttt taaataaaaa catagcaaga   1740
gaactggaag atactttgca ttgtaaaata tctcccaggg taatggagga attattaaag   1800
tggggagaag agttaggtaa ggctgaaagt gcctctctcc aatttcacat tctacgactt   1860
tttcactgcc tacacgagtc ccaggaggaa gacttcacaa agaagatgtt gggtcgtatc   1920
tttgaagttg accttaatat tttggaggac gaagaactcc aagcttcttc attttgccta   1980
aagcactgta aaaggttaaa taagctaagg ctttctgtta gcagtcacat ccttgaaagg   2040
gacttggaaa ttctggagtg caaatcggta actcctgagt gggttctgca ggacctcatt   2100
attgcccttc agggtaacag caagctgacc catctgaact tcagctctaa caagctggga   2160
atgactgtcc ccctgattct taaagctttg agacactcag cttgcaacct caagtatctg   2220
tgcctggaga atgcaacttt gtcggcagcc agctgtcagg acctagcctt gtttctcacc   2280
agcatccaac acgtaactcg attgtgcctg ggatttaatc ggctccaaga tgatggcata   2340
aagctattgt gtgcggccct gactcacccc aagtgtgcct tagagagact ggagctctgg   2400
ttttgccagc tggcagcacc cgcttgcaag cacttgtcag atgctctcct gcagaacagg   2460
agcctgacac acctgaatct gagcaagaac agcctgagag acgagggagt caagttcctg   2520
tgtgaggcct tgggtcgccc agatggtaac ctgcagagcc tgaatttgtc aggttgttct   2580
ttcacaagag agggctgtgg agagctggct aatgccctca gccataatca taatgtgaaa   2640
atcttggatt tgggagaaaa tgatcttcag gatgatggag tgaagctact gtgtgaggct   2700
ctgaaaccac atcgtgcatt gcacacactt gggttggcga aatgcaatct gacaactgct   2760
tgctgccagc atctcttctc tgttctcagc agcagtaaga gcctggtcaa tctgaacctt   2820
ctaggcaatg aattggatac tgatggtgtc aagatgctat cctctatcct cgtgtctttta  2880
gatttagacc ccttgttctt cgagccactt ccggactgcc aaattagact tcagttaaaa   2940
gactttagct cctggccccc cgtcagcccc tccggtgatg tgcaggacat ggaggtagaa   3000
tgggaccctg tttacaggaa taatattcag gttaatacaa aaccatcg                3048
```

```
<210> SEQ ID NO 21
<211> LENGTH: 3439
<212> TYPE: DNA
<213> ORGANISM: Homo sapiens
<220> FEATURE:
<221> NAME/KEY: CDS
<222> LOCATION: (100)...(3198)

<400> SEQUENCE: 21
ccacgcgtcc ggccaaggag acctggtggc agggttgatc tcatatttct tgtgcctcaa      60
aatcccttct ctgaagtctg ccttccctgg agaagcaag atg gca gaa tcg gat       114
                                            Met Ala Glu Ser Asp
                                              1               5 tct act gac ttt gac ctg ctg tgg tat cta gag aat ctc agt gac aag      162
Ser Thr Asp Phe Asp Leu Leu Trp Tyr Leu Glu Asn Leu Ser Asp Lys
             10                  15                  20 gaa ttt cag agt ttt aag aag tat ctg gca cgc aag att ctt gat ttc      210
Glu Phe Gln Ser Phe Lys Lys Tyr Leu Ala Arg Lys Ile Leu Asp Phe
         25                  30                  35 aaa ctg cca cag ttt cca ctg ata cag atg aca aaa gaa gaa ctg gct      258
Lys Leu Pro Gln Phe Pro Leu Ile Gln Met Thr Lys Glu Glu Leu Ala
     40                  45                  50 aac gtg ttg cca atc tct tat gag gga cag tat ata tgg aat atg ctc      306
Asn Val Leu Pro Ile Ser Tyr Glu Gly Gln Tyr Ile Trp Asn Met Leu
 55                  60                  65 ttc agc ata ttt tca atg atg cgt aag gaa gat ctt tgt agg aag atc      354
Phe Ser Ile Phe Ser Met Met Arg Lys Glu Asp Leu Cys Arg Lys Ile
                 70                  75                  80                  85 att ggc aga cga aac cgc aat cag gag gca tgc aaa gct gtc atg agg      402
Ile Gly Arg Arg Asn Arg Asn Gln Glu Ala Cys Lys Ala Val Met Arg
                 90                  95                 100 aga aaa ttc atg ctg caa tgg gaa agt cac act ttt gga aaa ttt cat      450
Arg Lys Phe Met Leu Gln Trp Glu Ser His Thr Phe Gly Lys Phe His
                105                 110                 115 tat aaa ttt ttt cgt gac gtt tcg tca gat gtg ttc tac ata ctt caa      498
Tyr Lys Phe Phe Arg Asp Val Ser Ser Asp Val Phe Tyr Ile Leu Gln
            120                 125                 130 tta gcc tat gat tct acc agc tat tat tca gca aac aat ctc aat gtg      546
Leu Ala Tyr Asp Ser Thr Ser Tyr Tyr Ser Ala Asn Asn Leu Asn Val
135                 140                 145 ttc ctg atg gga gag aga gca tct gga aaa act att gtt ata aat ctg      594
Phe Leu Met Gly Glu Arg Ala Ser Gly Lys Thr Ile Val Ile Asn Leu
150                 155                 160                 165 gct gtg ttg agg tgg atc aag ggt gag atg tgg cag aac atg atc tcg      642
Ala Val Leu Arg Trp Ile Lys Gly Glu Met Trp Gln Asn Met Ile Ser
                170                 175                 180 tac gtc gtt cac ctc act tct cac gaa ata aac cag atg acc aac agc      690
Tyr Val Val His Leu Thr Ser His Glu Ile Asn Gln Met Thr Asn Ser
            185                 190                 195 agc ttg gct gag cta atc gcc aag gac tgg cct gac ggc cag gct ccc      738
Ser Leu Ala Glu Leu Ile Ala Lys Asp Trp Pro Asp Gly Gln Ala Pro
        200                 205                 210 att gca gac atc ctg tct gat ccc aag aaa ctc ctt ttc atc ctc gag      786
Ile Ala Asp Ile Leu Ser Asp Pro Lys Lys Leu Leu Phe Ile Leu Glu
    215                 220                 225 gac ttg gac aac ata aga ttc gag tta aat gtc aat gaa agt gct ttg      834
Asp Leu Asp Asn Ile Arg Phe Glu Leu Asn Val Asn Glu Ser Ala Leu
230                 235                 240                 245 tgt agt aac agc acc cag aaa gtt ccc att cca gtt ctc ctg gtc agt      882
Cys Ser Asn Ser Thr Gln Lys Val Pro Ile Pro Val Leu Leu Val Ser
```

-continued

```
                    250                 255                 260
ttg ctg aag aga aaa atg gct cca ggc tgc tgg ttc ctc atc tcc tca         930
Leu Leu Lys Arg Lys Met Ala Pro Gly Cys Trp Phe Leu Ile Ser Ser
            265                 270                 275 agg ccc aca cgt ggg aat aat gta aaa acg ttc ttg aaa gag gta gat         978
Arg Pro Thr Arg Gly Asn Asn Val Lys Thr Phe Leu Lys Glu Val Asp
            280                 285                 290 tgc tgc acg acc ttg cag ctg tcg aat ggg aag agg gag ata tat ttt        1026
Cys Cys Thr Thr Leu Gln Leu Ser Asn Gly Lys Arg Glu Ile Tyr Phe
        295                 300                 305 aac tct ttc ttt aaa gac cgc cag agg gcg tcg gca gcc ctc cag ctt        1074
Asn Ser Phe Phe Lys Asp Arg Gln Arg Ala Ser Ala Ala Leu Gln Leu
310                 315                 320                 325 gta cat gag gat gaa ata ctc gtg ggt ctg tgc cga gtc gcc atc tta        1122
Val His Glu Asp Glu Ile Leu Val Gly Leu Cys Arg Val Ala Ile Leu
                330                 335                 340 tgc tgg atc acg tgt act gtc ctg aag cgg cag atg gac aag ggg cgt        1170
Cys Trp Ile Thr Cys Thr Val Leu Lys Arg Gln Met Asp Lys Gly Arg
                345                 350                 355 gac ttc cag ctc tgc tgc caa aca ccc act gat cta cat gcc cac ttt        1218
Asp Phe Gln Leu Cys Cys Gln Thr Pro Thr Asp Leu His Ala His Phe
            360                 365                 370 ctt gct gat gcg ttg aca tca gag gct gga ctt act gcc aat cag tat        1266
Leu Ala Asp Ala Leu Thr Ser Glu Ala Gly Leu Thr Ala Asn Gln Tyr
375                 380                 385 cac cta ggt ctc cta aaa cgt ctg tgt ttg ctg gct gca gga gga ctg        1314
His Leu Gly Leu Leu Lys Arg Leu Cys Leu Leu Ala Ala Gly Gly Leu
390                 395                 400                 405 ttt ctg agc acc ctg aat ttc agt ggt gaa gac ctc aga tgt gtt ggg        1362
Phe Leu Ser Thr Leu Asn Phe Ser Gly Glu Asp Leu Arg Cys Val Gly
                410                 415                 420 ttt act gag gct gat gtc tct gtg ttg cag gcc gcg aat att ctt ttg        1410
Phe Thr Glu Ala Asp Val Ser Val Leu Gln Ala Ala Asn Ile Leu Leu
                425                 430                 435 ccg agc aac act cat aaa gac cgt tac aag ttc ata cac ttg aac gtc        1458
Pro Ser Asn Thr His Lys Asp Arg Tyr Lys Phe Ile His Leu Asn Val
            440                 445                 450 cag gag ttt tgt aca gcc att gca ttt ctg atg gca gta ccc aac tat        1506
Gln Glu Phe Cys Thr Ala Ile Ala Phe Leu Met Ala Val Pro Asn Tyr
        455                 460                 465 ctg atc ccc tca ggc agc aga gag tat aaa gag aag aga gaa caa tac        1554
Leu Ile Pro Ser Gly Ser Arg Glu Tyr Lys Glu Lys Arg Glu Gln Tyr
470                 475                 480                 485 tct gac ttt aat caa gtg ttt act ttc att ttt ggt ctt cta aat gca        1602
Ser Asp Phe Asn Gln Val Phe Thr Phe Ile Phe Gly Leu Leu Asn Ala
                490                 495                 500 aac agg aga aag att ctt gag aca tcc ttt gga tac cag cta ccg atg        1650
Asn Arg Arg Lys Ile Leu Glu Thr Ser Phe Gly Tyr Gln Leu Pro Met
            505                 510                 515 gta gac agc ttc aag tgg tac tcg gtg gga tac atg aaa cat ttg gac        1698
Val Asp Ser Phe Lys Trp Tyr Ser Val Gly Tyr Met Lys His Leu Asp
                520                 525                 530 cgt gac ccg gaa aag ttg acg cac cat atg cct ttg ttt tac tgt ctc        1746
Arg Asp Pro Glu Lys Leu Thr His His Met Pro Leu Phe Tyr Cys Leu
535                 540                 545 tat gag aat cgg gaa gaa gaa ttt gtg aag acg att gtg gat gct ctc        1794
Tyr Glu Asn Arg Glu Glu Glu Phe Val Lys Thr Ile Val Asp Ala Leu
550                 555                 560                 565 atg gag gtt aca gtt tac ctt caa tca gac aag gat atg atg gtc tca        1842
```

```
                                                       -continued

Met Glu Val Thr Val Tyr Leu Gln Ser Asp Lys Asp Met Met Val Ser
        570                 575                 580 tta tac tgt ctg gat tac tgc tgt cac ctg agg aca ctt aag ttg agc      1890
Leu Tyr Cys Leu Asp Tyr Cys Cys His Leu Arg Thr Leu Lys Leu Ser
        585                 590                 595 gtt cag cgc atc ttt caa aac aaa gag cca ctt ata agg cca act gct      1938
Val Gln Arg Ile Phe Gln Asn Lys Glu Pro Leu Ile Arg Pro Thr Ala
        600                 605                 610 agt caa atg aag agc ctt gtc tac tgg aga gag atc tgc tct ctt ttt      1986
Ser Gln Met Lys Ser Leu Val Tyr Trp Arg Glu Ile Cys Ser Leu Phe
        615                 620                 625 tat aca atg gag agc ctc cgg gag ctg cat atc ttt gac aat gac ctt      2034
Tyr Thr Met Glu Ser Leu Arg Glu Leu His Ile Phe Asp Asn Asp Leu
630                 635                 640                 645 aat ggt att tca gaa agg att ctg tct aaa gcc ctg gag cat tct agc      2082
Asn Gly Ile Ser Glu Arg Ile Leu Ser Lys Ala Leu Glu His Ser Ser
                650                 655                 660 tgt aaa ctt cgc aca ctc aag ttg tcc tat gtc tcg act gct tct ggt      2130
Cys Lys Leu Arg Thr Leu Lys Leu Ser Tyr Val Ser Thr Ala Ser Gly
                665                 670                 675 ttt gaa gac tta ctc aag gct ttg gct cgt aat cgg agc ctg aca tac      2178
Phe Glu Asp Leu Leu Lys Ala Leu Ala Arg Asn Arg Ser Leu Thr Tyr
                680                 685                 690 ctg agt atc aac tgt acg tcc att tcc cta aat atg ttt tca ctt ctg      2226
Leu Ser Ile Asn Cys Thr Ser Ile Ser Leu Asn Met Phe Ser Leu Leu
        695                 700                 705 cat gac atc ctg cac gag ccc aca tgc caa ata agt cat ctg agc ttg      2274
His Asp Ile Leu His Glu Pro Thr Cys Gln Ile Ser His Leu Ser Leu
710                 715                 720                 725 atg aaa tgt gat ttg cga gcc agc gaa tgc gaa gaa atc gcc tct ctc      2322
Met Lys Cys Asp Leu Arg Ala Ser Glu Cys Glu Glu Ile Ala Ser Leu
                730                 735                 740 ctc atc agt ggc ggg agt ctg aga aaa ctg acc tta tcc agc aat ccg      2370
Leu Ile Ser Gly Gly Ser Leu Arg Lys Leu Thr Leu Ser Ser Asn Pro
                745                 750                 755 ctg agg agc gac ggg atg aac ata ctg tgt gat gcc ttg ctt cat ccc      2418
Leu Arg Ser Asp Gly Met Asn Ile Leu Cys Asp Ala Leu Leu His Pro
        760                 765                 770 aac tgc act ctt ata tca ctg gtg tta gtc ttc tgc tgt ctc act gaa      2466
Asn Cys Thr Leu Ile Ser Leu Val Leu Val Phe Cys Cys Leu Thr Glu
        775                 780                 785 aat tgc tgc agc gcc ctt gga aga gtg ctt ctg ttc agc cca act cta      2514
Asn Cys Cys Ser Ala Leu Gly Arg Val Leu Leu Phe Ser Pro Thr Leu
790                 795                 800                 805 aga caa cta gac ctg tgt gtg aat cgc tta aaa aat tac gga gtg ttg      2562
Arg Gln Leu Asp Leu Cys Val Asn Arg Leu Lys Asn Tyr Gly Val Leu
                810                 815                 820 cat gtg acg ttt ccc ttg ctg ttt cca acc tgt cag tta gag gag ctt      2610
His Val Thr Phe Pro Leu Leu Phe Pro Thr Cys Gln Leu Glu Glu Leu
                825                 830                 835 cat ctg tct ggc tgt ttc ttt agc agc gat atc tgt caa tat att gcc      2658
His Leu Ser Gly Cys Phe Phe Ser Ser Asp Ile Cys Gln Tyr Ile Ala
        840                 845                 850 ata gtt att gct act aat gaa aaa ctg agg agc ctg gag att ggg agc      2706
Ile Val Ile Ala Thr Asn Glu Lys Leu Arg Ser Leu Glu Ile Gly Ser
855                 860                 865 aac aaa ata gaa gat gca gga atg cag ctg cta tgt ggt ggt ttg aga      2754
Asn Lys Ile Glu Asp Ala Gly Met Gln Leu Leu Cys Gly Gly Leu Arg
870                 875                 880                 885
```

```
cat ccc aac tgc atg ttg gtg aat att ggg cta gaa gag tgc atg tta      2802
His Pro Asn Cys Met Leu Val Asn Ile Gly Leu Glu Glu Cys Met Leu
            890                 895                 900 acc agt gcc tgc tgt cga tct ctt gcc tct gtt ctt acc acc aac aaa      2850
Thr Ser Ala Cys Cys Arg Ser Leu Ala Ser Val Leu Thr Thr Asn Lys
            905                 910                 915 aca cta gaa aga ctc aac ttg ctt caa aat cac ttg ggc aat gat gga      2898
Thr Leu Glu Arg Leu Asn Leu Leu Gln Asn His Leu Gly Asn Asp Gly
            920                 925                 930 gtt gca aaa ctt ctt gag agc ttg atc agc cca gat tgt gta ctt aag      2946
Val Ala Lys Leu Leu Glu Ser Leu Ile Ser Pro Asp Cys Val Leu Lys
            935                 940                 945 gta gtt ggg ctt cca tta act ggc ctg aac aca caa acc cag cag ttg      2994
Val Val Gly Leu Pro Leu Thr Gly Leu Asn Thr Gln Thr Gln Gln Leu
950                 955                 960                 965 ctg atg act gta aag gaa aga aaa ccc agt ttg atc ttt ctg tct gaa      3042
Leu Met Thr Val Lys Glu Arg Lys Pro Ser Leu Ile Phe Leu Ser Glu
            970                 975                 980 act tgg tct tta aag gaa ggc aga gaa att ggt gtg aca cct gct tct      3090
Thr Trp Ser Leu Lys Glu Gly Arg Glu Ile Gly Val Thr Pro Ala Ser
            985                 990                 995 cag cca ggt tca ata ata cct aat tct aat ttg gat tac atg ttt ttc      3138
Gln Pro Gly Ser Ile Ile Pro Asn Ser Asn Leu Asp Tyr Met Phe Phe
            1000                1005                1010 aaa ttt ccc aga atg tct gca gcc atg aga acg tca aat aca gca tct      3186
Lys Phe Pro Arg Met Ser Ala Ala Met Arg Thr Ser Asn Thr Ala Ser
            1015                1020                1025 agg caa ccc ctt tgatcatgtt gtacgtaaac agtatttatt ataaattact         3238
Arg Gln Pro Leu
1030 accgtgactg ggatgcaaga gaattaggac tataattttc ctatttgatg tgtgtgtgtg   3298 tgtgtgtgtg tgtgtgtgtg tgtgtgtgtg tgtgtgacct tgatccagtc aaccacttca   3358 aattcctaca ctgtctcaag agtattaaaa ggattatatg aagtaataaa ggataaaatg   3418 cattggaaaa aaaaaaaaaa a                                             3439
```

<210> SEQ ID NO 22
<211> LENGTH: 1033
<212> TYPE: PRT
<213> ORGANISM: Homo sapiens

<400> SEQUENCE: 22

```
Met Ala Glu Ser Asp Ser Thr Asp Phe Asp Leu Leu Trp Tyr Leu Glu
1               5                   10                  15

Asn Leu Ser Asp Lys Glu Phe Gln Ser Phe Lys Lys Tyr Leu Ala Arg
            20                  25                  30

Lys Ile Leu Asp Phe Lys Leu Pro Gln Phe Pro Leu Ile Gln Met Thr
        35                  40                  45

Lys Glu Glu Leu Ala Asn Val Leu Pro Ile Ser Tyr Glu Gly Gln Tyr
    50                  55                  60

Ile Trp Asn Met Leu Phe Ser Ile Phe Ser Met Met Arg Lys Glu Asp
65                  70                  75                  80

Leu Cys Arg Lys Ile Ile Gly Arg Arg Asn Arg Asn Gln Glu Ala Cys
                85                  90                  95

Lys Ala Val Met Arg Arg Lys Phe Met Leu Gln Trp Glu Ser His Thr
            100                 105                 110

Phe Gly Lys Phe His Tyr Lys Phe Arg Asp Val Ser Ser Asp Val
        115                 120                 125
```

-continued

```
Phe Tyr Ile Leu Gln Leu Ala Tyr Asp Ser Thr Ser Tyr Ser Ala
        130                 135                 140
Asn Asn Leu Asn Val Phe Leu Met Gly Glu Arg Ala Ser Gly Lys Thr
145                 150                 155                 160
Ile Val Ile Asn Leu Ala Val Leu Arg Trp Ile Lys Gly Glu Met Trp
                165                 170                 175
Gln Asn Met Ile Ser Tyr Val Val His Leu Thr Ser His Glu Ile Asn
            180                 185                 190
Gln Met Thr Asn Ser Ser Leu Ala Glu Leu Ile Ala Lys Asp Trp Pro
        195                 200                 205
Asp Gly Gln Ala Pro Ile Ala Asp Ile Leu Ser Asp Pro Lys Lys Leu
210                 215                 220
Leu Phe Ile Leu Glu Asp Leu Asp Asn Ile Arg Phe Glu Leu Asn Val
225                 230                 235                 240
Asn Glu Ser Ala Leu Cys Ser Asn Ser Thr Gln Lys Val Pro Ile Pro
                245                 250                 255
Val Leu Leu Val Ser Leu Leu Lys Arg Lys Met Ala Pro Gly Cys Trp
                260                 265                 270
Phe Leu Ile Ser Ser Arg Pro Thr Arg Gly Asn Asn Val Lys Thr Phe
            275                 280                 285
Leu Lys Glu Val Asp Cys Cys Thr Thr Leu Gln Leu Ser Asn Gly Lys
290                 295                 300
Arg Glu Ile Tyr Phe Asn Ser Phe Phe Lys Asp Arg Gln Arg Ala Ser
305                 310                 315                 320
Ala Ala Leu Gln Leu Val His Glu Asp Glu Ile Leu Val Gly Leu Cys
                325                 330                 335
Arg Val Ala Ile Leu Cys Trp Ile Thr Cys Thr Val Leu Lys Arg Gln
            340                 345                 350
Met Asp Lys Gly Arg Asp Phe Gln Leu Cys Cys Gln Thr Pro Thr Asp
        355                 360                 365
Leu His Ala His Phe Leu Ala Asp Ala Leu Thr Ser Glu Ala Gly Leu
    370                 375                 380
Thr Ala Asn Gln Tyr His Leu Gly Leu Leu Lys Arg Leu Cys Leu Leu
385                 390                 395                 400
Ala Ala Gly Gly Leu Phe Leu Ser Thr Leu Asn Phe Ser Gly Glu Asp
                405                 410                 415
Leu Arg Cys Val Gly Phe Thr Glu Ala Asp Val Ser Val Leu Gln Ala
                420                 425                 430
Ala Asn Ile Leu Leu Pro Ser Asn Thr His Lys Asp Arg Tyr Lys Phe
            435                 440                 445
Ile His Leu Asn Val Gln Glu Phe Cys Thr Ala Ile Ala Phe Leu Met
    450                 455                 460
Ala Val Pro Asn Tyr Leu Ile Pro Ser Gly Ser Arg Glu Tyr Lys Glu
465                 470                 475                 480
Lys Arg Glu Gln Tyr Ser Asp Phe Asn Gln Val Phe Thr Phe Ile Phe
                485                 490                 495
Gly Leu Leu Asn Ala Asn Arg Arg Lys Ile Leu Glu Thr Ser Phe Gly
                500                 505                 510
Tyr Gln Leu Pro Met Val Asp Ser Phe Lys Trp Tyr Ser Val Gly Tyr
            515                 520                 525
Met Lys His Leu Asp Arg Asp Pro Glu Lys Leu Thr His His Met Pro
530                 535                 540
```

-continued

| | | | | | | | | | | | | | | | |
|---|---|---|---|---|---|---|---|---|---|---|---|---|---|---|---|
|Leu|Phe|Tyr|Cys|Leu|Tyr|Glu|Asn|Arg|Glu|Glu|Phe|Val|Lys|Thr| |
|545| | | |550| | | |555| | | |560| | | |
|Ile|Val|Asp|Ala|Leu|Met|Glu|Val|Thr|Val|Tyr|Leu|Gln|Ser|Asp|Lys|
| | | | |565| | | |570| | | |575| | | |
|Asp|Met|Met|Val|Ser|Leu|Tyr|Cys|Leu|Asp|Tyr|Cys|Cys|His|Leu|Arg|
| | | |580| | | | |585| | | |590| | | |
|Thr|Leu|Lys|Leu|Ser|Val|Gln|Arg|Ile|Phe|Gln|Asn|Lys|Glu|Pro|Leu|
| | |595| | | | |600| | | | |605| | | |
|Ile|Arg|Pro|Thr|Ala|Ser|Gln|Met|Lys|Ser|Leu|Val|Tyr|Trp|Arg|Glu|
| |610| | | | |615| | | | |620| | | | |
|Ile|Cys|Ser|Leu|Phe|Tyr|Thr|Met|Glu|Ser|Leu|Arg|Glu|Leu|His|Ile|
|625| | | | |630| | | | |635| | | | |640|
|Phe|Asp|Asn|Asp|Leu|Asn|Gly|Ile|Ser|Glu|Arg|Ile|Leu|Ser|Lys|Ala|
| | | |645| | | | |650| | | | |655| | |
|Leu|Glu|His|Ser|Ser|Cys|Lys|Leu|Arg|Thr|Leu|Lys|Leu|Ser|Tyr|Val|
| | | |660| | | | |665| | | | |670| | |
|Ser|Thr|Ala|Ser|Gly|Phe|Glu|Asp|Leu|Leu|Lys|Ala|Leu|Ala|Arg|Asn|
| | |675| | | | |680| | | | |685| | | |
|Arg|Ser|Leu|Thr|Tyr|Leu|Ser|Ile|Asn|Cys|Thr|Ser|Ile|Ser|Leu|Asn|
| |690| | | | |695| | | | |700| | | | |
|Met|Phe|Ser|Leu|Leu|His|Asp|Ile|Leu|His|Glu|Pro|Thr|Cys|Gln|Ile|
|705| | | | |710| | | | |715| | | | |720|
|Ser|His|Leu|Ser|Leu|Met|Lys|Cys|Asp|Leu|Arg|Ala|Ser|Glu|Cys|Glu|
| | | |725| | | | |730| | | | |735| | |
|Glu|Ile|Ala|Ser|Leu|Leu|Ile|Ser|Gly|Gly|Ser|Leu|Arg|Lys|Leu|Thr|
| | | |740| | | | |745| | | | |750| | |
|Leu|Ser|Ser|Asn|Pro|Leu|Arg|Ser|Asp|Gly|Met|Asn|Ile|Leu|Cys|Asp|
| | |755| | | | |760| | | | |765| | | |
|Ala|Leu|Leu|His|Pro|Asn|Cys|Thr|Leu|Ile|Ser|Leu|Val|Leu|Val|Phe|
| |770| | | | |775| | | | |780| | | | |
|Cys|Cys|Leu|Thr|Glu|Asn|Cys|Cys|Ser|Ala|Leu|Gly|Arg|Val|Leu|Leu|
|785| | | | |790| | | | |795| | | | |800|
|Phe|Ser|Pro|Thr|Leu|Arg|Gln|Leu|Asp|Leu|Cys|Val|Asn|Arg|Leu|Lys|
| | | |805| | | | |810| | | | |815| | |
|Asn|Tyr|Gly|Val|Leu|His|Val|Thr|Phe|Pro|Leu|Leu|Phe|Pro|Thr|Cys|
| | | |820| | | | |825| | | | |830| | |
|Gln|Leu|Glu|Glu|Leu|His|Leu|Ser|Gly|Cys|Phe|Phe|Ser|Ser|Asp|Ile|
| | | |835| | | | |840| | | | |845| | |
|Cys|Gln|Tyr|Ile|Ala|Ile|Val|Ile|Ala|Thr|Asn|Glu|Lys|Leu|Arg|Ser|
| | | |850| | | | |855| | | | |860| | |
|Leu|Glu|Ile|Gly|Ser|Asn|Lys|Ile|Glu|Asp|Ala|Gly|Met|Gln|Leu|Leu|
|865| | | | |870| | | | |875| | | | |880|
|Cys|Gly|Gly|Leu|Arg|His|Pro|Asn|Cys|Met|Leu|Val|Asn|Ile|Gly|Leu|
| | | | |885| | | | |890| | | | |895| | |
|Glu|Glu|Cys|Met|Leu|Thr|Ser|Ala|Cys|Cys|Arg|Ser|Leu|Ala|Ser|Val|
| | | |900| | | | |905| | | | |910| | |
|Leu|Thr|Thr|Asn|Lys|Thr|Leu|Glu|Arg|Leu|Asn|Leu|Gln|Asn|His|
| | | |915| | | | |920| | | | |925| | | |
|Leu|Gly|Asn|Asp|Gly|Val|Ala|Lys|Leu|Leu|Glu|Ser|Leu|Ile|Ser|Pro|
| | | |930| | | | |935| | | | |940| | | |
|Asp|Cys|Val|Leu|Lys|Val|Val|Gly|Leu|Pro|Leu|Thr|Gly|Leu|Asn|Thr|
|945| | | | |950| | | | |955| | | | |960|
|Gln|Thr|Gln|Gln|Leu|Leu|Met|Thr|Val|Lys|Glu|Arg|Lys|Pro|Ser|Leu|

965                 970                 975
Ile Phe Leu Ser Glu Thr Trp Ser Leu Lys Glu Gly Arg Glu Ile Gly
            980                 985                 990

Val Thr Pro Ala Ser Gln Pro Gly Ser Ile Ile Pro Asn Ser Asn Leu
            995                 1000                1005

Asp Tyr Met Phe Phe Lys Phe Pro Arg Met Ser Ala Ala Met Arg Thr
        1010                1015                1020

Ser Asn Thr Ala Ser Arg Gln Pro Leu
1025                1030

<210> SEQ ID NO 23
<211> LENGTH: 3099
<212> TYPE: DNA
<213> ORGANISM: Homo sapiens

<400> SEQUENCE: 23

| | | | | | |
|---|---|---|---|---|---|
| atggcagaat | cggattctac | tgactttgac | ctgctgtggt | atctagagaa | tctcagtgac | 60 |
| aaggaatttc | agagttttaa | gaagtatctg | gcacgcaaga | ttcttgattt | caaactgcca | 120 |
| cagtttccac | tgatacagat | gacaaaagaa | gaactggcta | acgtgttgcc | aatctcttat | 180 |
| gagggacagt | atatatggaa | tatgctcttc | agcatatttt | caatgatgcg | taaggaagat | 240 |
| ctttgtagga | agatcattgg | cagacgaaac | cgcaatcagg | aggcatgcaa | agctgtcatg | 300 |
| aggagaaaat | tcatgctgca | atgggaaagt | cacacttttg | gaaaatttca | ttataaattt | 360 |
| tttcgtgacg | tttcgtcaga | tgtgttctac | atacttcaat | tagcctatga | ttctaccagc | 420 |
| tattattcag | caaacaatct | caatgtgttc | ctgatgggag | agagagcatc | tggaaaaact | 480 |
| attgttataa | atctggctgt | gttgaggtgg | atcaagggtg | agatgtggca | gaacatgatc | 540 |
| tcgtacgtcg | ttcacctcac | ttctcacgaa | ataaaccaga | tgaccaacag | cagcttggct | 600 |
| gagctaatcg | ccaaggactg | gcctgacggc | aggctcccca | ttgcagacat | cctgtctgat | 660 |
| cccaagaaac | tcctttcat | cctcgaggac | ttggacaaca | taagattcga | gttaaatgtc | 720 |
| aatgaaagtg | ctttgtgtag | taacagcacc | cagaaagttc | ccattccagt | tctcctggtc | 780 |
| agtttgctga | agagaaaaat | ggctccaggc | tgctggttcc | tcatctcctc | aaggcccaca | 840 |
| cgtgggaata | atgtaaaaac | gttcttgaaa | gaggtagatt | gctgcacgac | cttgcagctg | 900 |
| tcgaatggga | agagggagat | atattttaac | tctttcttta | aagaccgcca | gagggcgtcg | 960 |
| gcagccctcc | agcttgtaca | tgaggatgaa | atactcgtgg | gtctgtgccg | agtcgccatc | 1020 |
| ttatgctgga | tcacgtgtac | tgtcctgaag | cggcagatga | caaggggcg | tgacttccag | 1080 |
| ctctgctgcc | aaacacccac | tgatctacat | gcccactttc | ttgctgatgc | gttgacatca | 1140 |
| gaggctggac | ttactgccaa | tcagtatcac | ctaggtctcc | taaaacgtct | gtgtttgctg | 1200 |
| gctgcaggag | gactgtttct | gagcaccctg | aatttcagtg | gtgaagacct | cagatgtgtt | 1260 |
| gggtttactg | aggctgatgt | ctctgtgttg | caggccgcga | atattctttt | gccgagcaac | 1320 |
| actcataaag | accgttacaa | gttcatacac | ttgaacgtcc | aggagttttg | tacagccatt | 1380 |
| gcatttctga | tggcagtacc | caactatctg | atcccctcag | gcagcagaga | gtataaagag | 1440 |
| aagagagaac | aatactctga | ctttaatcaa | gtgtttactt | tcattttttgg | tcttctaaat | 1500 |
| gcaaacagga | gaaagattct | tgagacatcc | tttggatacc | agctaccgat | ggtagacagc | 1560 |
| ttcaagtggt | actcggtggg | atacatgaaa | catttggacc | gtgacccgga | aaagttgacg | 1620 |
| caccatatgc | ctttgttta | ctgtctctat | gagaatcggg | aagaagaatt | tgtgaagacg | 1680 |
| attgtggatg | ctctccatgga | ggttacagtt | taccttcaat | cagacaagga | tatgatggtc | 1740 |

```
tcattatact gtctggatta ctgctgtcac ctgaggacac ttaagttgag cgttcagcgc   1800
atctttcaaa acaaagagcc acttataagg ccaactgcta gtcaaatgaa gagccttgtc   1860
tactggagag agatctgctc tcttttttat acaatggaga gcctccggga gctgcatatc   1920
tttgacaatg accttaatgg tatttcagaa aggattctgt ctaaagccct ggagcattct   1980
agctgtaaac ttcgcacact caagttgtcc tatgtctcga ctgcttctgg ttttgaagac   2040
ttactcaagg ctttggctcg taatcggagc ctgacatacc tgagtatcaa ctgtacgtcc   2100
atttccctaa atatgttttc acttctgcat gacatcctgc acgagcccac atgccaaata   2160
agtcatctga gcttgatgaa atgtgatttg cgagccagcg aatgcgaaga aatcgcctct   2220
ctcctcatca gtggcgggag tctgagaaaa ctgaccttat ccagcaatcc gctgaggagc   2280
gacgggatga acatactgtg tgatgccttg cttcatccca actgcactct tatatcactg   2340
gtgttagtct tctgctgtct cactgaaaat tgctgcagcg cccttggaag agtgcttctg   2400
ttcagcccaa ctctaagaca actagacctg tgtgtgaatc gcttaaaaaa ttacggagtg   2460
ttgcatgtga cgtttccctt gctgtttcca acctgtcagt tagaggagct tcatctgtct   2520
ggctgtttct ttagcagcga tatctgtcaa tatattgcca tagttattgc tactaatgaa   2580
aaactgagga gcctggagat tgggagcaac aaaatagaag atgcaggaat gcagctgcta   2640
tgtggtggtt tgagacatcc caactgcatg ttggtgaata ttgggctaga agagtgcatg   2700
ttaaccagtg cctgctgtcg atctcttgcc tctgttctta ccaccaacaa aacactagaa   2760
agactcaact tgcttcaaaa tcacttgggc aatgatggag ttgcaaaact tcttgagagc   2820
ttgatcagcc cagattgtgt acttaaggta gttgggcttc cattaactgg cctgaacaca   2880
caaacccagc agttgctgat gactgtaaag gaaagaaaac ccagtttgat ctttctgtct   2940
gaaacttggt cttaaagga aggcagagaa attggtgtga cacctgcttc tcagccaggt   3000
tcaataaatac ctaattctaa tttggattac atgttttttca aatttcccag aatgtctgca   3060
gccatgagaa cgtcaaatac agcatctagg caaccccttt                         3099
```

GENE ENCODING PROMOTER DOMAIN OF TUMOR SUPPRESSOR GENE P51 AND USE THEREOF

This application is a 371 of PCT/JP00/04261 filed on Jun. 28, 2000.

TECHNICAL FIELD

The present invention relates to a gene encoding the promoter region of a protein p51 which is capable of inducing cell death, suppressing cell growth, etc. and a gene encoding the 5'-untranslated region of p51. The present invention also relates to a series of uses of these genes.

BACKGROUND ART

The tumor suppressor gene p53 encodes a protein having a variety of functions such as the induction of apoptosis, cell cycle arrest, the repairing of DNA damages, and the like. It has also been shown that p53 is a transcription factor which regulates the expression of various proteins. Currently this protein is believed to play a central role in the control of cell growth. It has also been reported that p53 mutation is observed in about half of tumor cells which is mainly responsible for abnormal growth and resistance against anti-cancer agents. Although no proteins were known that have a p53-like structure and function until very recently, but two novel p53-like molecules were recently reported. One is p73 (Cell, 90:809–819, 1997), and the other is p51 (Nature Medicine, 4:839–843, 1998). Concerning p51, a protein encoded by the same gene is reported as p63 (Molecular Cell, 2:305–316, 1998). Structurally p51 is very similar to p53, and like p53 it is capable of activating the transcription of a cell cycle progression suppressor protein p21, suggesting that it is homologous to p53 functionally as well. Furthermore, it is reported that p51, as is p53, is capable of inducing cell death, suppressing cell growth, and the like. It has been shown, however, that p51 is different from p53 in that no mutation in p51 has been observed in tumor cells. It is being elucidated that p51 is expressed in very limited organs such as muscle cells.

DISCLOSURE OF THE INVENTION

It is an object of the present invention to identify the gene encoding the promoter region of a tumor suppressor gene p51 and the gene encoding the 5'-untranslated region of p51, thereby to provide a method of cloning these genes, a method of screening novel drugs using these genes, and a novel method of gene therapy using these genes, and the like.

After intensive and extensive research to find a gene fragment containing the p51 promoter in a human genomic library, the inventor of the present invention has identified a gene sequence having the p51 promoter region, and a gene sequence encoding the 5'-untranslated region of p51, and thereby has completed the present invention.

Thus, a human genome fragment containing a same sequence as cDNA complementary to p51 mRNA was screened and isolated by the plaque hybridization screening method. Furthermore, the base sequence of this gene fragment was determined to confirm that it contains regions that are estimated to be the p51 promoter region and the 5'-untranslated region of p51. A plasmid was also constructed in which the gene fragment is ligated to the luciferase reporter gene, and it was then introduced into a human cell line to construct a transformant. By further analyzing this transformant, it was found out that said gene can work as a promoter. Furthermore, there was found a method of screening an agent that acts on the p51 promoter using transformant, and a possibility that a pharmaceutical agent that enhances this promoter activity acts as a therapeutic agent such as an anti-cancer agent for diseases in which abnormality in p53-dependent apoptosis is involved.

Thus, the present invention relates to a gene encoding the p51 promoter region shown in the following (1), (2), (3), (4), (5), or (6):

(1) DNA that encodes the p51 promoter region having the base sequence as set forth in SEQ ID NO: 1 of the sequence listing;

(2) DNA that has a base sequence in which one or a plurality of bases have been deleted, substituted, or added in the base sequence as set forth in SEQ ID NO: 1 of the sequence listing, and that has p51 promoter activity;

(3) DNA that hybridizes to the base sequence as set forth in SEQ ID NO: 1 of the sequence listing under a stringent condition, and that has p51 promoter activity;

(4) DNA that has the base sequence as set forth in SEQ ID NO: 2 of the sequence listing, and that encodes the p51 promoter region and the 5'-untranslated region of p51;

(5) DNA that has a base sequence in which one or a plurality of bases have been deleted, substituted, or added in the base sequence as set forth in SEQ ID NO: 2 of the sequence listing, and that has p51 promoter activity; and (6) DNA that hybridizes to the base sequence as set forth in SEQ ID NO: 2 of the sequence listing under a stringent condition, and that has p51 promoter activity.

The present invention also relates to a gene encoding the 5'-untranslated region of p51 shown in the following (7), (8), or (9):

(7) DNA that has a base sequence of positions from 5677 to 5960 in the base sequence as set forth in SEQ ID NO: 2 of the sequence listing;

(8) DNA that has a base sequence in which one or a plurality of bases have been deleted, substituted, or added in a base sequence of positions from 5677 to 5960 in the base sequence as set forth in SEQ ID NO: 2 of the sequence listing, and that has a function similar to that of DNA in the above (7); and (9) DNA that hybridizes to DNA comprising the base sequence of positions from 5677 to 5960 in the base sequence as set forth in SEQ ID NO: 2 of the sequence listing under a stringent condition, and that has a function similar to that of DNA in the above (7).

The present invention further relates to a recombinant plasmid comprising the gene in the above (1) to (6).

The present invention further relates to a transformant or a transductant comprising the above recombinant plasmid.

The present invention further relates to nucleic acid probes comprising all or parts of the base sequence of the gene in the above (1) to (9).

The present invention further relates to a method of cloning p51 promoter by hybridization using the above nucleic acid probe.

The present invention further relates to a DNA sequence that is an antisense to all or part of the base sequence of the gene in the above (1) to (9), and that can modify the function of p51 promoter activity.

The present invention further relates to a RNA sequence that is an antisense to all or part of the base sequence of the gene in the above (1) to (9), and that can modify the function of p51 promoter activity.

The present invention further relates to a method of screening drugs that act on the p51 promoter using the above transformant or the above transductant.

The present invention further relates to a compound that enhances or inhibits the expression of p51 gene, said compound being selected by the above screening method.

The present invention further relates to a pharmaceutical formulation comprising the above DNA or the above RNA.

BEST MODE FOR CARRYING OUT THE INVENTION

Figure 1:
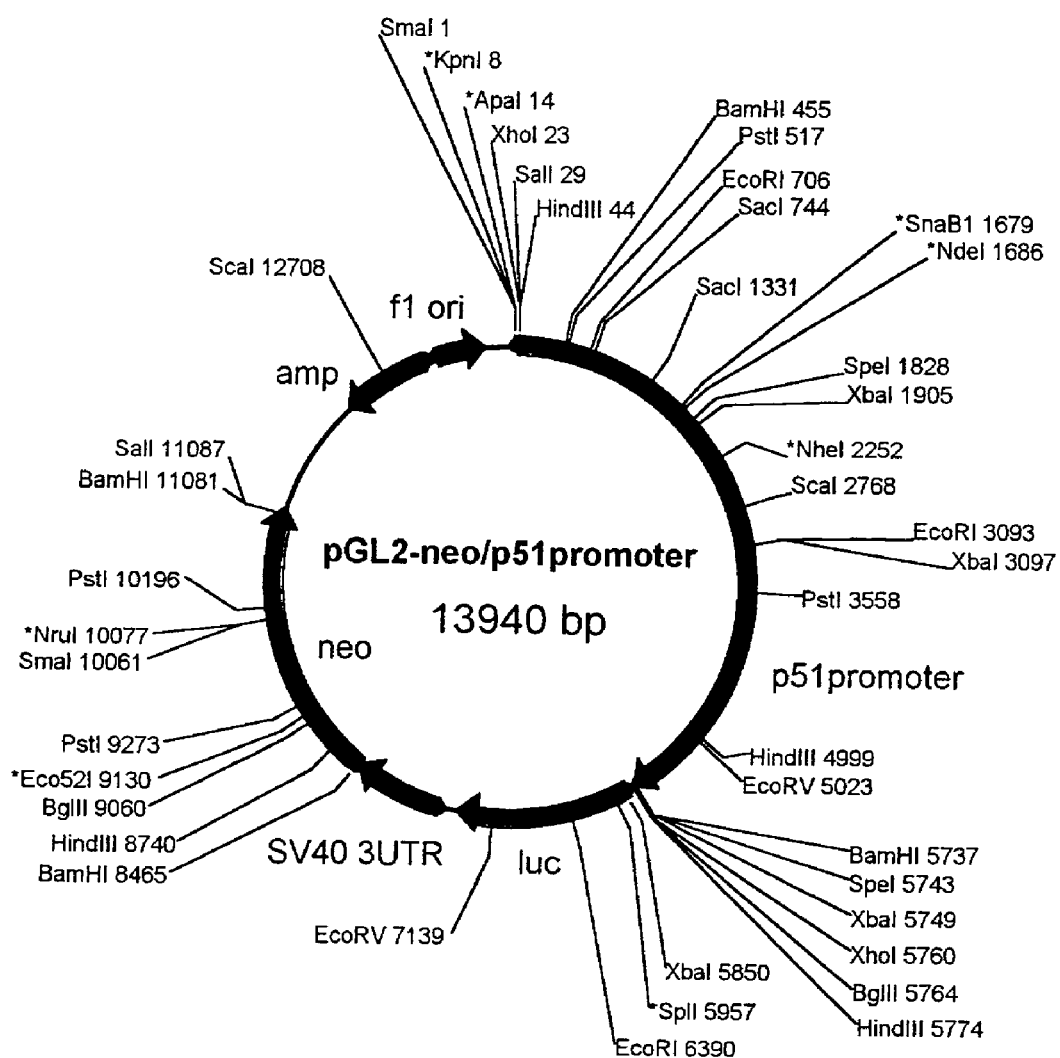
FIG. 1 is a diagram showing a restriction map of pGL2-neo/p51 promoter. In the figure, amp represents an ampicillin-resistant gene, neo represents a neomycin-resistant gene, and luc represents the luciferase gene. The name of a restriction enzyme that has a * mark on the left means that the vector can be only cleaved at the point.

The present invention will now be explained in further details below.

(1) Gene Having the p51 Promoter Region of the Present Invention (1-1) In order to isolate a gene having the p51 promoter region of the present invention, a human genomic DNA library is constructed, and from the library, using part of the sequence described in the above-mentioned article in Nature Medicine, a cDNA molecule that hybridizes to a cDNA complementary to the 5'-untranslated region of p51 mRNA can be isolated and cloned resulting in the isolation of a gene encoding the p51 promoter region.

The base sequence of a gene encoding the p51 promoter region of the present invention is as set forth in SEQ ID NO: 1. In this gene sequence, TATA boxes have been observed in the bases in positions from 5630 to 5636 and in positions from 5659 to 5665 of the above same sequence listing. They are located at 47 bases and 18 bases upstream of a gene sequence (GenBank AB016072) reported as the sequence of p51A protein mRNA (p51AmRNA), respectively. Furthermore, the binding site of MEF2 known to be a muscle cell-specific transcription factor is located in the bases at positions from 1211 to 1220 of the same sequence listing. In a search of the database for genes having a homology with the gene encoding The p51 promoter region as set forth in SEQ ID NO: 1 of the sequence listing, no sequences had a homology of 30% or higher over the entire length.

Furthermore, for the purpose of confirming the function of the gene having the base sequence as set forth in SEQ ID NO: 1 of the sequence listing, as shown in the following Example, a plasmid was constructed in which a gene having the base sequence as set forth in SEQ ID NO: 1 of the sequence listing and the luciferase reporter gene were ligated, which was then expressed in a cultured human cell line to construct a transformant. The transformant significantly expressed the luciferase reporter gene as compared to the control group. Furthermore, a simple screening using the transformant led to the discovery of the p51 promoter activating ability in trichostatin A. One µg/ml of trichostatin A (manufactured by Wako Pure Chemical Industries, Ltd.) transactivates p51 in the cultured human cell line, and it was confirmed under this condition that the promoter activity of the gene having the isolated p51 promoter region was further remarkably enhanced. Thus, these results demonstrate that the gene having the base sequence as set forth in SEQ ID NO: 1 of the sequence listing has a function as a p51 promoter.

(1-2) DNA that has a base sequence in which one or a plurality of bases have been deleted, substituted, or added in the base sequence as set forth in SEQ ID NO: 1 of the sequence listing, and that has p51 promoter activity, is also encompassed in the scope of the present invention. The deletion, substitution, or addition of bases is to a degree that does not substantially affect the structure and function of the entire promoter. The degree of deletion, substitution, or addition of these bases is acceptable when it has p51 promoter activity and it has a homology with the original base sequence of 80% or higher, preferably 90% or higher, and more preferably 99% or higher.

(1-3) DNA that hybridizes to DNA comprising the base sequence as set forth in SEQ ID NO: 1 of the sequence listing under a stringent condition and that has a p51 promoter activity is also encompassed in the scope of the present invention. Such hybridizing DNA mutants include DNA sequences partially altered by the mutation, deletion, ligation etc. of DNA fragments by site-directed mutagenesis, mutagen-treated random mutation, cleavage with restriction enzymes. The degree to which these DNA mutants hybridize to the coding gene as set forth in SEQ ID NO: 1 is a stringent condition: for example, the above membrane is incubated in a hybridization solution (50 mM Tris-HCl, pH 7.5, 1 M sodium chloride, 1% sodium dodecylsulfate, 10% dextran sulfate, 0.2 mg/ml yeast RNA, 0.2 mg/ml salmon sperm DNA) at 65° C. for one hour as prehybridization, then a radioisotope-labeled cDNA fragment is added to one million dpm/ml in terms of the amount of radioisotope and incubated at 65° C. for 16 hours as hybridization, and subsequently the membrane is washed in a 2×SSC solution (300 mM sodium chloride, 30 mM trisodium citrate) containing 0.1% sodium dodecylsulfate at 65° C. for 30 minutes, followed by autoradiography analysis to confirm hybridization on an X-ray film.

(1-4) DNA that is shown in SEQ ID NO: 2 of the sequence listing and that encodes the p51 promoter region and the 5'-untranslated region of p51 is also encompassed in the scope of the present invention. The base sequence of positions from 5677 to 5960 in the SEQ ID NO: 2 corresponds to DNA encoding 5'-untranslated region. Among them, the base sequence of positions from 5767 to 5960 corresponds to the intron region.

(1-5) DNA that has a base sequence in which one or a plurality of bases have been deleted, substituted, or added in the base sequence as set forth in SEQ ID NO: 2 of the sequence listing and that has p51 promoter activity is also encompassed in the scope of the present invention. The deletion, substitution, or addition of bases is to a degree that does not substantially affect the structure and function of the entire promoter. The degree of deletion, substitution, or addition of these bases is acceptable when it has p51 promoter activity and it has a homology with the original base sequence of 80% or higher, preferably 90% or higher, and more preferably 99% or higher.

(1-6) DNA that hybridizes to DNA comprising the base sequence as set forth in SEQ ID NO: 2 of the sequence listing under a stringent condition and that has p51 promoter activity is also encompassed in the scope of the present invention. Such hybridizing DNA mutants include those similar to those exhibited in the above (1-3). The degree to which these DNA mutants hybridize to the gene as set forth in SEQ ID NO: 2 is such that hybridization is confirmed under a stringent condition similar to the one described in the above (1-3).

(2) Gene Encoding the 5'-Untranslated Region of p51 of the Present Invention (2-1) DNA that has a base sequence of positions from 5677 to 5960 in the base sequence as set forth in SEQ ID NO: 2 of the sequence listing is DNA that encodes the 5'-untranslated region of p51 located downstream of the p51 promoter region, and such DNA is also encompassed in the scope of the present invention. Among them, the base sequence of positions from 5767 to 5960 corresponds to the intron region. Part or all of DNA that encodes the 5'-untranslated region of p51 may be used as a nucleic acid probe, for example, for cloning a gene as described below.

(2-2) DNA that has a base sequence in which one or a plurality of bases have been deleted, substituted, or added in a base sequence of positions from 5677 to 5960 in the base sequence as set forth in SEQ ID NO: 2 of the sequence listing, and that has a function similar to that of the DNA in the above (2-1) is also encompassed in the scope of the present invention. The deletion, substitution, or addition of bases is to a degree that it does not substantially effect the structure and function of the DNA. The degree of deletion, substitution, or addition of these bases is acceptable when it has a function similar to DNA described in the above (2-1) and it has a homology with the original base sequence of 80% or higher, preferably 90% or higher, and more preferably 99% or higher.

(2-3) DNA that hybridizes to DNA comprising the base sequence of positions from 5677 to 5960 in the base sequence as set forth in SEQ ID NO: 2 of the sequence listing under a stringent condition, and that has a function similar to that of DNA in the above (2-1) is also encompassed in the scope of the present invention. Such hybridizing DNA mutants include those similar to those exhibited in the above (1-3). The degree to which these DNA mutants hybridize to the gene as set forth in SEQ ID NO: 2 is such that hybridization is confirmed under a stringent condition similar to the one described in the above (1-3).

(3) A Recombinant Plasmid Containing a Gene Having the p51 Promoter Region of the Present Invention By constructing a recombinant plasmid containing a gene having the p51 promoter region of the present invention, it is possible to allow *Escherichia coli* etc. to stably retain said gene, whereupon vectors used include any commonly used ones such as pBluescript II SK(−). In the examples described below, there is exhibited the pBS/p51 promoter in which a gene having the p51 promoter region has been integrated into pBluescript II SK(−). After cleaving these plasmids with an appropriate restriction enzyme as needed, they can be ligated to an suitable vector to make plasmids for determining promoter activity. As a plasmid for determining promoter activity, a plasmid such as pGL2 can be used as a vector.

(4) A Transformant or a Transductant

The above recombinant plasmid can be introduced into an appropriate host to construct a transformant or a transductant. *Escherichia coli*, yeast, and mammalian cells can be used. A transformant that retains a plasmid for determining promoter activity can be obtained by transforming into an appropriate host a recombinant plasmid that has been integrated into a vector for determining activity as described above. For example, a recombinant plasmid as shown in FIG. 1 may be introduced into a cultured mamallian cell to obtain a transformant. A transformant or a transductant may be cultured in an appropriate nutrient culture medium and the amount of the reporter gene expressed in the cell may be measured to determine the promoter activity.

(5) A Nucleic Acid Probe, and Gene Cloning and Detection Using it.

In accordance with the present invention, part or all of the gene having the p51 promoter region of the present invention or part or all of the gene encoding the 5'-untranslated region of p51 of the present invention may be used as a nucleic acid probe for use in gene cloning etc. described below. As a nucleic acid probe comprising part of the gene of the present invention, there may be mentioned a nucleic acid probe comprising an oligonucleotide of 15 nucleotides or more. Said nucleic acid probe may be prepared by ligating the above gene of the present invention or a gene fragment thereof to a suitable vector, which is then introduced into a bacterium, replicated, extracted from the debris of cell homogenate with phenol etc., cleaving with the restriction enzyme that recognizes the site at which the vector is ligated, electrophoresing, and excising the probe from the gel. Said nucleic acid probe may also be prepared, based on the base sequence as set forth in SEQ ID NO: 1 or 2 of the sequence listing, by chemical synthesis using a DNA synthesizer or by a gene amplification technology with polymerase chain reaction (PCR). Said nucleic acid probe may be labeled with a radioisotope or fluorescence to enhance detection sensitivity at the time of use.

Said nucleic acid probe may be used in the cloning method of genes other than the above having a promoter activity or the cloning method of the protein-encoding genes located downstream thereof. Thus, by searching the genome library of various biological tissues by the hybridization method or the PCR method using said nucleic acid probe, it is possible to isolate genes having a similar function to the gene of the present invention or protein-encoding genes located downstream thereof.

(6) Antisense DNA and Antisense RNA

In accordance with the present invention, there may also be provided antisense DNAs and antisense RNAs of genes having the above-mentioned p51 promoter region as well as antisense DNAs and antisense RNAs of genes having the 5'-untranslated region of p51. By introducing these antisense DNAs and antisense RNAs into a cell, the expression of genes encoding p51 can be suppressed or enhanced. As the antisense DNA to be introduced, there can be used, for example, an antisense DNA or part thereof corresponding to SEQ ID NO: 1 or 2 of the sequence listing. An example of said antisense DNA is shown in SEQ ID NO: 3 of the sequence listing. This represents the sequence of the antisense DNA of a gene having the p51 promoter activity of SEQ ID NO: 1 of the sequence listing. As antisense DNA, for example, there can be used a fragment obtained by suitably cleaving part of these antisense DNAs or DNAs synthesized based on the DNA sequences of these antisense DNAs.

As antisense RNA, for example, there can be used antisense RNA or part thereof corresponding to SEQ ID NO: 1 or 2 of the sequence listing. An example of said antisense RNA is shown in SEQ ID NO: 4 of the sequence listing. This represents the sequence of the antisense RNA of the gene having the p51 promoter activity of SEQ ID NO: 1 of the sequence listing. As antisense RNA, for example, there can be used a fragment obtained by suitably cleaving part of these antisense RNAs or RNAs synthesized based on the RNA sequences of these antisense RNAs. A gene SEQ ID NO: 1 of the sequence listing having the p51 promoter activity or part thereof may be ligated to an appropriate vector, which is then introduced into a bacterium, replicated, extracted from the debris of cell homogenate with phenol etc., which is used as a template to allow RNA polymerase to act in an in vitro transcription system to synthesize RNA to be used. Antisense DNAs and antisense RNAs may be chemically modified so that they are refractory to in vivo decomposition and they can pass through cell membrane. The antisense DNAs and antisense RNAs thus prepared can be used for the treatment of various diseases including malignant tumor.

(7) Drug Screening

In accordance with the present invention, there is provided a screening method for novel drugs using the transformant or the transductant of the present invention. For example, an agent that has the p51 promoter region activation activity and that enhances the expression of p51 protein can be discovered by screening drugs that enhance luciferase activity using a cultured cell that has integrated a recombinant plasmid in which the luciferase reporter gene and said gene have been ligated.

As cultured cells into which a recombinant plasmid is to be introduced, any cultured cell lines that can be passaged can be used including a cultured colon cancer cell line HCT-116. As recombinant plasmids, any vector can be used that contains a reporter gene including pGL2-neo vector in which the neomycin gene has been ligated to the pGL2 plasmid used in Examples. In the construction of a screening system, a cultured cell line is selected into which a vector for screening is introduced by the lipofectin method, etc. By culturing this transformed cell together with the selection drug, cells that contain the vector for screening can only be grown. These cells may be used as they are in screening or may be cloned to be prepared as a single cell line and then used in screening. By adding a sample to these cells and then determining the activity of the reporter protein, agents that regulate the transcription of p51 can be searched. As samples, for example, microbial secondary metabolites may be used, or synthetic compounds may be used. Agents that activates the p51 promoter enhance the production of p51 protein and exhibit a growth suppressing effect on tumor cells, even if p53 is mutated in these cells, and thereby are expected to become novel anti-cancer agents.

(8) Pharmaceutical Preparation

The p51's expression is only observed in highly localized tissues such as muscle cells. Thus, it can be used as a gene therapy vector by ligating a gene of interest downstream of the gene having the p51 promoter activity of the present invention, and allowing it to express the gene of interest only in specific tissues. The above antisense DNAs and antisense RNAs can be therapeutic agents for various disease including malignant tumor, also.

Now, the present invention will be specifically explained below. It is to be noted, however, that the present invention is not limited by these examples in any way.

EXAMPLE 1

Isolation of a Novel Gene Fragment Encoding the p51 Promoter Region (1-1) Preparation of a probe for screening A probe for screening a novel gene fragment that encodes the p51 promoter region was prepared. As such a method, the RT-PCR method was used. The experimental procedure is shown below. From a six µg of human muscle-derived RNA (manufactured by OriGene), cDNA was prepared using 200 units of a reverse transcriptase Superscript (manufactured by GIBCO BRL). With this as the template, the amplification of a p51 mRNA-derived gene fragment was attempted by a PCR method using a primer set shown in SEQ ID NO: 5 and 6 and a primer set shown in SEQ ID NO: 7 and 8. The gene amplified using the former primer set encodes 143 bases of the 5'-untranslated region of p51A mRNA reported until now and 165 bases of the 5'-terminal end of the open reading frame, and the gene amplified using the latter primer set encodes the full-length of the p51A mRNA open reading frame. The base sequence of the former gene is shown in SEQ ID NO: 9 of the sequence listing. In performing the PCR method, a DNA polymerase EX Taq (manufactured by Takara Shuzo) was used, and the PCR condition comprised 30 cycles of amplification with each cycle comprising 95° C. for one minute, 55° C. for one minute, and 72° C. for one minute. PCR amplified products were subjected to phenol treatment and chloroform treatment to remove protein, and then to ethanol precipitation. Then this DNA was washed in 70% ethanol and dissolved in a sterile water. After these purified DNAs and 20 ng of E. coli vector pBluescript KS(+) (manufactured by Toyobo) which was cleaved with a restriction enzyme EcoRV (manufactured by Takara Shuzo), and in which one thymine was added (referred to hereinafter as pBS/EcoRV TA), were ligated using a DNA ligation kit (manufactured by Takara Shuzo) (the plasmid containing the amplified gene obtained with the primer set shown in SEQ ID NO: 5 and 6 is hereinafter referred to as pBS/p51-1, and the gene containing the amplified gene obtained with the primer set shown in SEQ ID NO: 7 and 8 is hereinafter referred to as pBS/p51A ORF). The absence of mutation in the amplified genes was confirmed by determining the base sequences of pBS/p51-1 and pBS/p51A ORF. The determination of the base sequence was performed using an automated sequencer LONG READIR4200 (manufactured by LICOR). Subsequently, pBS/p51-1 was cleaved with restriction enzymes EcoRV and PstI (manufactured by Toyobo), which were then fractionated on a 0.8% agarose electrophoresis, extracted, and purified. For purification, EASYTRAP (manufactured by Takara Shuzo) was used. This purified DNA was used as a template for the screening probe.

(1-2) Screening of a Novel Gene Fragment Encoding the p51 promoter region

Subsequently, the screening of gene fragments of a gene encoding the p51 promoter region from a human genomic library was attempted. As the human genomic library, Easy-to-Handle Eukaryotic Genomic Library from human (manufactured by Mo Bi Tec) was used. The infection efficiency of this library was three million plaque forming units per microliter. Using this library, a membrane for plaque hybridization was prepared in the following manner. 0.02 µl of the library solution and 0.9 ml of C600 E. coli solution (E. coli strain C600 was cultured under shaking in 50 ml of the LB medium (0.5% yeast extract, 1% peptone, 0.5% sodium chloride) containing 0.2% maltose and 10 mM magnesium sulfate) at 37° C. for 16 hours, centrifuged at 5000 rpm for 5 minutes, recovered, and then suspended in 25 ml of 10 mM magnesium sulfate) were mixed, and incubated at 37° C. for 15 minutes so as to be infected with phage. Seven ml of LB soft agar (0.7% agar was added to 0.5% yeast extract, 1% peptone, 0.5% sodium chloride and 10 mM magnesium sulfate to prepare an agar medium) that was incubated at 47° C. after melting was added thereto, gently mixed, and then was plated onto a LB-magnesium sulfate plate (1.5% agar was added to 0.5% yeast extract, 1% peptone, 0.5% sodium chloride and 10 mM magnesium sulfate to prepare an agar medium) with an internal diameter of 150 mm. By this procedure, 60,000 plaques appeared per plate. A similar procedure was used to plate on a total of 23 plates. They were incubated at 37° C. for 16 hours to form plaques. After the plate was cooled at 4° C. for one hour, the plaques were adhered to a nylon membrane, Colony plaque screen (manufactured by NEN). After this membrane was dried, it was allowed to denature in 500 ml of an alkaline solution (0.2 N sodium hydroxide, 1.5 M sodium chloride) at room temperature for 2 minutes followed by neutralization in 500 ml of a neutralizing solution (0.5 M Tris-HCl, pH 7.2, 1.5 M sodium chloride, 1 mM ethylenediaminetetraacetic acid disodium salt) at room temperature for 2 minutes. This membrane was then incubated in a 3×SSC solution (450 mM sodium chloride, 45 mM trisodium citrate) at 55° C. for one hour, and dried to prepare a membrane for plaque hybridization. Fifty ng of the above purified cDNA fragment obtained by cleaving pBS/p51-1 with restriction enzymes EcoRV and PstI was labeled using Prime-It II (manufactured by Stratagene) to prepare a probe for screening.

Then the membrane was used for plaque hybridization. The above membrane was incubated in 50 ml of a hybridization solution (50 mM Tris-HCl, pH 7.5, 1 M sodium chloride, 1% sodium dodecylsulfate, 10% dextran sulfate, 0.2 mg/ml yeast RNA, 0.2 mg/ml salmon sperm DNA) at 65° C. for one hour as prehybridization. Then a radioisotope-labeled cDNA fragment was added to one million dpm/ml in terms of the amount of radioisotope and incubated at 65° C. for 16 hours as hybridization. Subsequently the membrane was washed in a 2×SSC solution (300 mM sodium chloride, 30 mM trisodium citrate) containing 0.1% sodium dodecylsulfate at 65° C. for 30 minutes. The washing was performed twice. Then, the membrane was subjected to autoradiography to detect positive plaques.

Then, plaque groups containing plaques corresponding to positive signal were isolated, and suspended in one ml of the SM buffer solution (50 mM Tris-HCl, pH 7.5, 100 mM sodium chloride, 10 mM magnesium sulfate, 0.01% gelatin). The solution was incubated at 4° C. for 16 hours to elute phage, and the phage was recovered in the supernatant fluid after centrifuging at 13000 rpm for 10 minutes. The phage solution was plated on a LB-magnesium sulfate plate in a manner similar to the above to screen positive plaques. As a result, positive plaques were successfully isolated as completely isolated plaques. From these plaques, phage was isolated in a manner similar to the above.

Subsequently, the following experiment was performed in order to determine the base sequence of the library DNA contained in this phage. The library has been made using lambda PS phage (manufactured by Mo Bi Tec). The phage has the recombinant site of loxP in the base sequence thereof, and thereby it can be introduced into an E. coli strain BNN132 having Cre recombinase in order to excise the vector portion containing the genome library sequence from the phage. This procedure was carried out as described below. Twenty µl of the phage solution was mixed with 200 µl of the BNN132 E. coli solution (E. coli strain BNN132 was cultured under shaking in 50 ml of the LB medium containing 0.2% maltose and 10 mM magnesium sulfate at 37° C. for 16 hours, and then recovered by centrifuging at 5000 rpm for 5 minutes, which was then suspended in 25 ml solution of 10 mM magnesium sulfate) and incubated at 37° C. for 30 minutes. The mixture was then plated onto the LB-ampicillin plate (1.5% agar was added to 0.5% yeast extract, 1% peptone, 0.5% sodium chloride and 0.1 mg/ml ampicillin sodium to prepare an agar medium), and the plasmid of interest was prepared from the colonies appeared. The preparation of the plasmid was performed according to the procedure described in Lab Manual Gene Engineering (Published by Maruzen, edited by Masami Muramatsu, 1990) on pages 53-55. The plasmid was found to contain about 15 kb of the library gene. This is referred to hereinafter as pPS/library.

(1-3) Sequencing of the Gene Fragment Encoding the p51 Promoter Region

Then, part of the base sequence of the library gene in pPS/library was determined using an automated sequencer LONG READIR4200 to confirm that it contains part of the cDNA sequence complementing p51A mRNA. It was also found that a 0.6 kb gene fragment obtained by cleaving of pPS/library with a restriction enzyme EcoRV contains part of the cDNA sequence that complements p51A mRNA. The pPS/library was then cleaved with a restriction enzyme PvuII (manufactured by Toyobo), fractionated on 0.8% agarose electrophoresis, and blotted on a nylon membrane Hybond N+ (manufactured by Amersham). Blotting of the plasmid fragment was performed according to the procedure described in Lab Manual Human Genome Mapping (published by Maruzen, eddited by Masaaki Hori and Yusuke Nakamura, 1991) on pages 26-36. This membrane was used in Southern blotting according to the following procedure. As a cDNA fragment for probing, pPS/library was used and cleaved with a restriction enzyme EcoRV, and after fractionation on a 0.8% agarose electrophoresis a 0.6 kb gene fragment was excised and purified using EASYTRAP. This purified cDNA was radiolabeled using Prime-It II to prepare a probe. The membrane was incubated in a hybridization solution for Southern blotting (10% sodium dodecylsulfate, 7% PEG8000) at 65° C. for one hour as prehybridization. Then the above probe was added to one million dpm/ml in terms of the amount of radioisotope and incubated at 65° C. for 16 hours for hybridization. Subsequently, the membrane was washed in a 2×SSC solution containing 0.1% sodium dodecylsulfate at 65° C. for 30 minutes. The washing was performed twice. Then, the membrane was subjected to autoradiography to demonstrate that a PvuII-cleaved fragment containing the immediate upstream region of p51A mRNA was 5.5 kb in length. Then, pPS/library was cleaved with a restriction enzyme PvuII, and after fractionation on a 0.8% agarose electrophoresis a 5.5 kb gene fragment was excised and purified using EASYTRAP. The purified cDNA fragment was ligated, using the DNA ligation kit, to pBluescript II Sk(+) that had been cleaved with a restriction enzyme EcoRV followed by dephosphorylation with shrimp alkaline phosphatase. The plasmid is referred to hereinafter as pBS/PvuII5.5. Its base sequence was determined using the automated sequencer LONG READIR 4200. The base sequence and the partial base sequence of the pPS/library determined above were combined to obtain the base sequence as set forth in SEQ ID NO: 2 of the sequence listing. Furthermore, a base sequence obtained by removing the part that encodes the 5'-untranslated region of p51 from the base sequence as set forth in SEQ ID NO: 2 of the sequence listing is shown in SEQ ID NO: 1 of the sequence listing. The 3'-terminal of this PvuII-cleaved fragment was found to be located about 0.22 kb upstream of the base at position 1 of SEQ ID NO: 9 of the sequence listing that is a cDNA sequence corresponding to p51A mRNA.

Accordingly, in order to prepare a plasmid containing bases up to the base at position 1 of SEQ ID NO: 9 of the sequence listing that is cDNA corresponding to part of p51A mRNA, the following procedure was performed. The pPS/library was cleaved with a restriction enzyme EcoRV, which was fractionated on a 0.8% agarose electrophoresis and then a 0.6 kb gene fragment was excised and purified using EASYTRAP, which was ligated using a DNA ligation kit to pBS/PvuII5.5 that had been cleaved with a restriction enzyme EcoRV and a restriction enzyme SmaI (manufactured by Takara Shuzo) followed by dephosphorylation with shrimp alkaline phosphatase. The plasmid obtained was analyzed and the plasmid that was ligated in the correct direction was isolated. The plasmid is referred to hereinafter as pBS/p51 promoter.

In order to demonstrate that the base sequence is surely present on the genome, the following experiment was performed. From a colon cancer cell line HCT116, genomic DNA was prepared, which was used as a template in a PCR. The genomic DNA was prepared according to Cell Engineering Experimental Protocol (published by Shujunsha, edited by Tokyo University, the Institute of Medical Science, Department of Anti-Cancer Research, 1993) on pages 16-19. The primers used are those shown in SEQ ID NO: 10 and 11. Respectively, they correspond to the sense strand of the bases at positions from 3543 to 3570 and the antisense strand of the bases at positions from 5458 to 5487 of the base sequence as set forth in SEQ ID NO: 1 of the sequence listing. Polymerase used was LA Taq (manufactured by Takara Shuzo), and PCR comprised 30 cycles of amplification with each cycle comprising 94° C. for one minute and 68° C. for three minutes. The PCR products were subjected to a 0.8% agarose electrophoresis to confirm that a gene fragment of 1.9 kb was specifically amplified. Furthermore, after the fragment was excised, it was purified using EASYTRAP, and ligated to pBS/EcoRV TA using a DNA ligation kit. The base sequence of this plasmid was determined using an automated sequencer LONG READIR 4200, and it was confirmed to completely match the base sequence in the pBS/p51 promoter.

(1-4) Construction of a Luciferase Vector Containing the p51 Promoter Region

In order to confirm that promoter activity is present on the isolated region, a vector in which the gene sequence was ligated upstream of the luciferase reporter gene was prepared according to the following method. As the vector having the luciferase reporter gene, pGL2 (manufactured by Promega) was used. First, to allow for integration of pGL2 and selection in mammalian cells, and a neomycin-resistant gene was introduced into this vector. The pGL2 cleaved with a restriction enzyme BamHI (manufactured by Toyobo) was ligated using a DNA ligation kit to a 2617-base neomycin-resistant gene, being obtained by cleaving pMAM neo (manufactured by Toyobo) with BamHI and fractionating on a 0.8% agarose gel electrophoresis excised and purified using EASYTRAP. The plasmid is referred to hereinafter as pGL2-neo. Subsequently, pGL2-neo was cleaved with a restriction enzyme XhoI (manufactured by Toyobo), precipitated with ethanol, washed in 70% ethanol, and dissolved in purified water. The cleaved end of this DNA was blunt-ended using a DNA blunting kit (manufactured by Takara Shuzo), precipitated with ethanol, washed in 70% ethanol, and dissolved in purified water. Then, this DNA was cleaved with a restriction enzyme KpnI (manufactured by Boehringer Mannheim), treated with phenol, treated with chloroform to remove protein, precipitated with ethanol, washed in 70% ethanol, and dissolved in sterile water. This DNA is referred to hereinafter as pGL2-neo/XhoI (blunting), KpnI.

Subsequently, the pBS/p51 promoter was cleaved with a restriction enzyme NotI (manufactured by Boehringer Mannheim), precipitated with ethanol, washed in 70% ethanol, and dissolved in purified water. After the cleaved end of this DNA was blunt-ended using a DNA blunting kit (manufactured by Takara Shuzo), precipitated with ethanol, washed in 70% ethanol, and dissolved in purified water. Then, this DNA was cleaved with a restriction enzyme KpnI (manufactured by Boehringer Mannheim), fractionated on a 0.8% agarose electrophoresis, and a 5.7 kb gene fragment was excised and purified using EASYTRAP. This gene fragment is referred to hereinafter as pBS/p51 promoter/NotI (blunting), KpnI5.7. Then, pGL2-neo/XhoI (blunting), KpnI and pBS/p51 promoter/NotI (blunting), KpnI5.7 were ligated using a DNA ligation kit. This plasmid is referred to hereinafter as pGL2-neo/p51 promoter. The gene sequence of this plasmid is shown in SEQ ID NO: 12 of the sequence listing. The restriction map of this plasmid is shown in FIG. 1.

(1-5) Effect of Various Drugs on the Amount of p51 Transcribed

1) Northern Hybridization

A variety of stimulations including stimulation with a drug were applied to a cell line HCT116 derived from colon cancer to investigate changes in the amount expressed of p51 by Northern blotting. 200,000 cells of HCT116 cells were plated on a culture dish with a diameter of 60 mm, and cultured in the presence of 5% carbon dioxide at 37° C. for two days. The medium used was McCOY's 5A (manufactured by Nisseiken) to which fetal bovine serum (FBS) was added to a final concentration of 10% (referred to hereinafter as McCOY's 5A/10% FBS). Then it was treated with A23187 (0.1 µM, 1 µM), cisplatin (1 µg/ml, 10 µg/ml), CPTcAMP (0.1 µM, 1 µM), etoposide (10 µg/ml, 0.1 µg/ml), genistein (1 µM, 10 µM), ML-236B (1 µg/ml, 10 µg/ml), milurinone (1 µM, 10 µM), mitomycin C (5 µg/ml, 50 µg/ml), NKH477 (0.1 µM, 1 µM), okadaic acid (1 nM, 10 nM), radicicol (0.1 µg/ml, 1 µg/ml), staurosporin (1 nM, 10 nM), taxol (1 µg/ml, 10 µg/ml), trichostatin A (0.1 µg/ml, 1 µg/ml), radiation (50 J/m$^2$, 100 J/m$^2$), vitamin D$_3$ (10 nM, 100 nM), vincristine (1 µg/ml, 10 µg/ml), and wortmannin (0.1 µM, 1 aM), and further cultured in the presence of 5% carbon dioxide at 37° C. for 24 hours. Then, from the cells, RNA was prepared using ISOGEN (manufactured by Nippongene). 20 µg each of RNA was fractionated on a 1% agarose electrophoresis containing formamldehyde, and blotted on a nylon membrane HybondN+ according to the method in the above New Cell Engineering Experimental Protocol on pages 194–197. As the probe, pBS/p51A ORF was cleaved with a restriction enzyme EcoRI (manufactured by Toyobo), fractionated on a 0.8% agarose electrophoresis, and then a 0.6 kb gene fragment was excised and purified using EASYTRAP, which was radiolabeled with Prime-It II and used. The membrane was incubated in 10 ml of a prehybridization solution (25 mM phosphate buffer solution, pH 7.0, 6×SSC, 50% formamide, 5× Denhardt's solution, 0.1% sodium dodecylsulfate, 0.2 mg/ml salmon sperm DNA) at 42° C. for four hours as prehybridization. Then it was replaced with 10 ml of a hybridization solution (20 mM phosphate buffer solution, pH 7.0, 6×SSC, 50% formamide, 1× Denhardt's solution, 0.1% sodium dodecylsulfate, 0.1 mg/ml salmon sperm DNA, 4% dextran sulfate), and then the above radiolabeled probe was added to one million dpm/ml and incubated at 42° C. for 16 hours as hybridization. Subsequently, it was washed in a 2×SSC solution containing 0.1% sodium dodecylsulfate at 65° C. for 30 minutes. The washing was performed twice. Then, the membrane was analyzed on autoradiography.

2) Result

Figure 2:
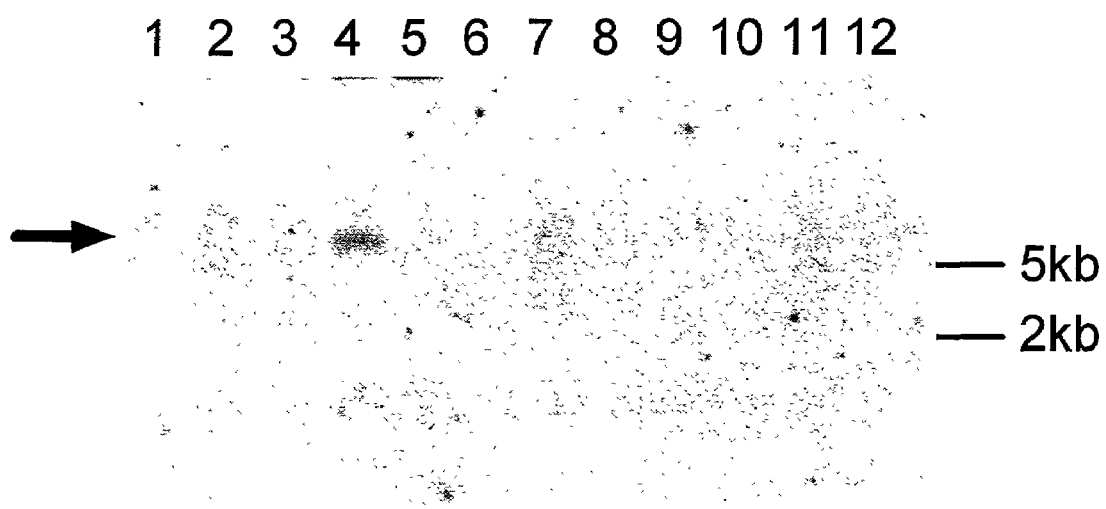
FIG. 2 shows an analysis in which the amount of p51 expressed was analyzed using the technique of Northern blotting after a cell line HCT116 derived from colon cancer, was subjected to various stimulations. In each lane is blotted 20 µg of RNA from: lane 1, 2: cells treated with taxol (1 µg/ml, 10 µg/ml), lane 3, 4: cells treated with trichostatin A (0.1 µg/ml, 1 µg/ml), lane 5, 6: cells treated with radiation (50 J/m$^2$, 100 J/m$^2$), lane 7, 8: cells treated with vitamin D$_3$ (10 nM, 100 nM), lane 9, 10: cells treated with vincristine (1 µg/ml, 10 µg/ml), and lane 11, 12: cells treated with wortmannin (0.1 µm, 1 µm). A band that reacts with the p51 probe is observed at the position indicated by an arrow.

As a result, a specific band that reacts with p51A-derived cDNA was only observed in the cells treated with 1 µg/ml trichostatin A. In any other stimulation, no increases in the amount of p51A mRNA were observed. FIG. 2 shows an increase in the amount of p51A mRNA with trichostatin A treatment. FIG. 2 shows blotting of 20 µg of RNA from: lane 1 and 2: cells treated with taxol (1 µg/ml, 10 µg/ml), lane 3 and 4: cells treated with trichostatin A (0.1 µg/ml, 1 µg/ml), lane 5 and 6: cells treated with radiation (50 J/m$^2$, 100 J/m$^2$), lane 7 and 8: cells treated with vitamin D$_3$ (10 nM, 100 nM), lane 9 and 10: cells treated with vincristine (1 µg/ml, 10 µg/ml), and lane 11 and 12: cells treated with wortmannin (0.1 µM, 1 µM).

(1-6) Functional Analysis of the p51 Promoter Region

Subsequently, the following experiment was carried out in order to perform functional analysis of the p51 promoter region. 200,000 cells of HCT116 were plated on a culture dish with a diameter of 60 mm. The medium used was McCOY's 5A/10% FBS. These were cultured in the presence of 5% carbon dioxide at 37° C. for 48 hours. The medium was replaced with McCOY's 5A containing no serum. Subsequently, 2 µg each of pGL2-neo/p51 promoter or pGL2-neo vector was introduced. The plasmid was introduced using the lipofectamine plus reagent (manufactured by GIBCO BRL). Thus, 125 µl of McCOY's 5A and 8 µl of the plus solution were added to the plasmid solution, stirred well, and then incubated at room temperature for 15 minutes. To this solution, 125 µl of McCOY's 5A and 12 µl of lipofectamine solution were added, stirred well, and then incubated at room temperature for further 15 minutes. This was added to the HCT116 cells incubated by the above procedure, gently mixed, and cultured in the presence of 5% carbon dioxide at 37° C. for three hours to introduce plasmid. Subsequently, the medium was replaced with McCOY's 5A/10% FBS, and cultured in the presence of 5% carbon dioxide at 37° C. for 21 hours. Then, trichostatin A was added to two groups of cells to a final concentration of 0 or 1 µg/ml, and cultured in the presence of 5% carbon dioxide at 37° C. for 24 hours. For these cells, the luciferase activity was determined to investigate promoter activity. As a negative control, cells containing no luciferase gene, pcDNA3/lacZ (the lacZ gene ligated to the mammalian cell expression vector pcDNA3) was transfected in a procedure similar to the above. The luciferase activity was determined according to the following method.

Figure 3:
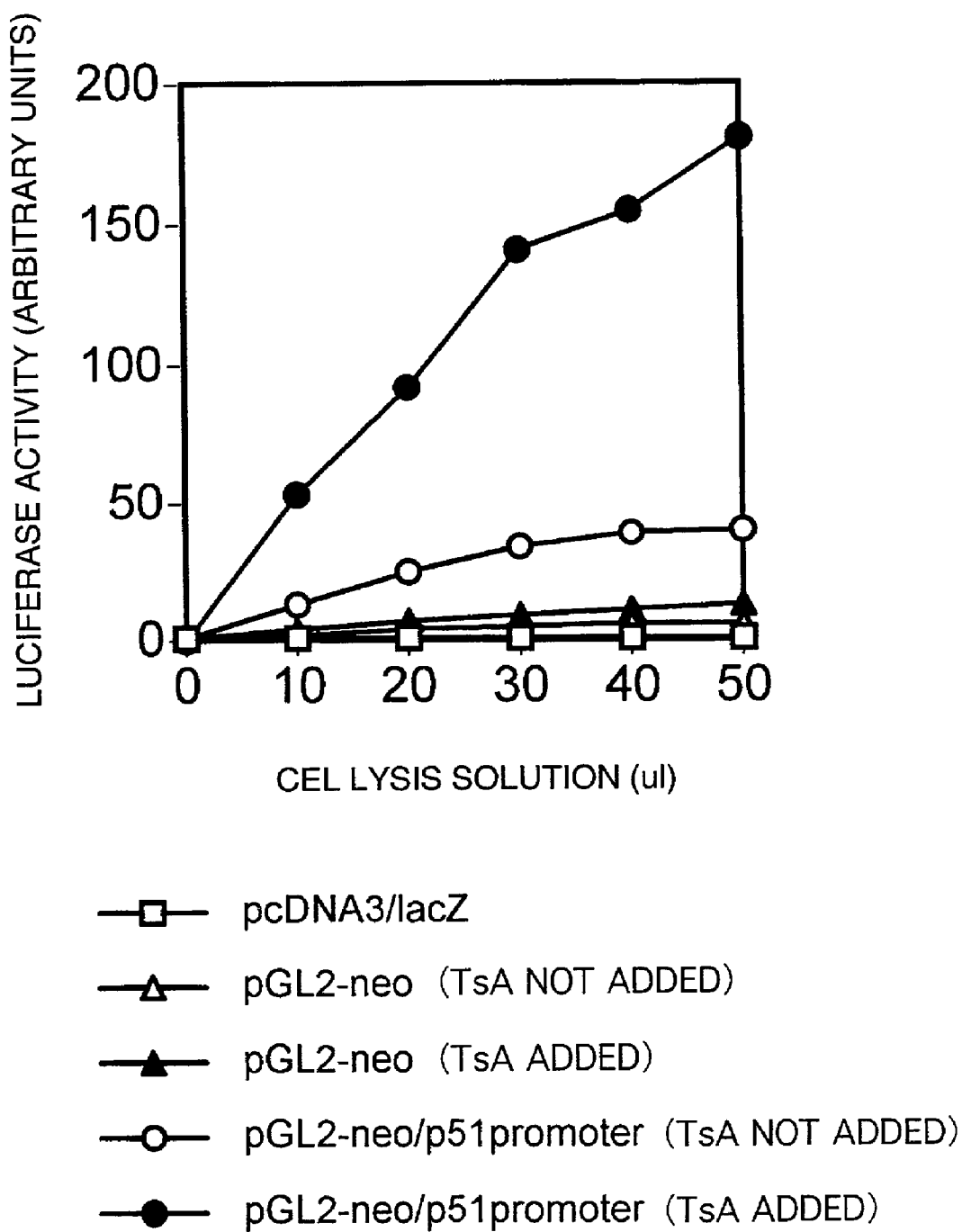
FIG. 3 shows a cell line HCT116 derived from colon cancer, into which 2 µg each of pGL2-neo/p51 promoter or pGL2-neo vector was introduced and 24 hours later, 0 or 1 µg/ml trichostatin A (TsA) was added and was further cultured for 24 hours. By determining the luciferase activity in these cells, the promoter activity of the isolated gene fragments was examined. As a negative control cell, cells into which 2 µg of pcDNA3/lacZ was introduced were used. As a result, it was found that an extract of the pGL2-neo/p51 promoter-introduced cells exhibits a significantly higher fluorescence intensity than that of the pGL2-neo-introduced cells. The administration of trichostatin A further enhanced the chemilumicescence intensity in the extract of the pGL2-neo/p51 promoter-introduced cells.

The medium in the cell culture dish was removed, and 5 ml of the cell lysis reagent (25 mM Tris-HCl, pH 7.8, 2 mM dithiothreitol, 2 mM CDTA, 0.2% triton X-100, 10% glycerol) was added and incubated at room temperature for 15 minutes. The cell lysis solution was taken at 10, 20, 30, 40, and 50 µl aliquotes, to which 50 µl of the substrate solution (20 mM Tricine-sodium hydroxide, pH 7.8, 1.07 mM basic magnesium carbonate, 2.67 mM magnesium sulfate, 0.1 mM ethylenediaminetetraacetic acid disodium salt, 33.3 mM dithiothreitol, 270 µM coenzyme A, 470 µM luciferine, 530 µM adenosine triphosphate) was added, and incubated at room temperature for 15 seconds, and its chemiluminescence intensity was determined using a luminometer LUMINOSKAN (manufactured by Dainippon Pharmaceutical). The result is shown in FIG. 3.

These results demonstrated that pGL2-neo/p51 promoter-introduced cell lysis solution exhibits a significantly high fluorescence intensity compared to pGL2-neo. The administration of trichostatin A also markedly enhanced fluorescence intensity in the pGL2-neo/p51 promoter. The result is in agreement with the above result in FIG. 2.

The above experimental data demonstrated that the isolated gene fragment is a functional p51 promoter region.

EXAMPLE 2

Screening of Drugs that Modify the p51 Promoter Function (2-1) Preparation of a Cultured Cell Line for Screening The cultured cell line retaining the pGL2-neo/p51 promoter plasmid can be used as cells for screening drugs that modify the p51 promoter function. Said drug is effective for treatment of various diseases including cancer. Said cells were prepared according to the following procedure.

As the plasmid-introduced cells, the HCT116 cell line was used. 500,000 cells of HCT116 cell were plated on a cuture dish with a diameter of 60 mm. The medium used was McCOY's 5A/10% FBS. These were cultured in the presence of 5% carbon dioxide at 37° C. for 48 hours. The medium was replaced with McCOY's 5A containing no serum. As the plasmid for introduction, two µg of pGL2-neo/p51 promoter was dissolved in 4 µl of the TE solution to prepare a plasmid solution. The plasmid was introduced using the lipofectamine plus reagent (manufactured by GIBCO BRL). Thus, 125 µl of McCOY's 5A and 8 µl of the plus solution were added to the plasmid solution, stirred well, and then incubated at room temperature for 15 minutes. To this solution, 125 µl of McCOY's 5A and 12 µl of the lipofectamine solution were added, stirred well, and then incubated at room temperature for further 15 minutes. This was added to the HCT116 cells cultured by the above procedure, gently mixed, and incubated in the presence of 5% carbon dioxide at 37° C. for three hours to permit the introduction of the plasmid. Subsequently, the medium was replaced with McCOY's 5A/10% FBS, and incubated in the presence of 5% carbon dioxide at 37° C. for 21 hours. Then, the cells were recovered from the culture dish with PBS containing 0.25% trypsin and 0.02% EDTA, and 1% amount thereof was plated onto a culture dish with a diameter of 100 mm. It was further cultured in McCOY's 5A/10% FBS medium in the presence of 5% carbon dioxide at 37° C. for further 72 hours, and then 1.2 mg/ml of geneticin (manufactured by Nacalai Tesque) was added as a selection drug. By replacing the medium every three days, and further culturing in the above condition for further two weeks, the cells into whose genes the plasmid gene was introduced, and became geneticin-resistant, were selected. Subsequently, 50 clones were isolated from the cell group that formed colonies on the dish, and were plated on a 24-well culture dish to continue being cultured.

These clones are expected to exhibit an enhanced luciferase activity to stimulation such as the activation of the p51 promoter function. Thus, the reactivity of these clones to trichostatin A was investigated by the following procedure. 500,000 cells each of the cloned cells were plated on a cuture dish with a diameter of 60 mm. The medium used was McCOY's 5A/10% FBS. These were cultured in the presence of 5% carbon dioxide at 37° C. for 48 hours. Then, trichostatin A was added to the two groups of cells to a final concentration of 0 or 0.1 µg/ml, and cultured in the presence of 5% carbon dioxide at 37° C. for 24 hours. For these cells, their luciferase activity was determined to examine the effect on the p51 promoter activity. The luciferase activity was determined according to the above method. As a result, several clones were obtained that exhibit a significantly enhanced luciferase activity to 0.1 µg/ml trichostatin A, from among which HCT116/p51 promoter clone #9 was selected as the cell for screening. The result of luciferase assay is shown in Table 1.

TABLE 1

| Clone No. | #5 | #9 | #17 | #18 |
|---|---|---|---|---|
| Without TsA | 3.9 | 1.0 | 17.0 | 6.8 |
| With TsA | 29.5 | 33.3 | 44.1 | 14.0 |

In the Table, TsA represents trichostatin A. The trichostatin A treatment group received at 0.1 µg/ml. Values in the table show the measured values of luciferase activity (2-2) Screening of Drugs that Modify the p51 Promoter Function HCT116/p51 promoter clone #9 cultured cell line is useful for screening drugs that induce the activation of the p51 promoter function. Said screening was performed according to the following procedure. 10,000 cells of HCT116/p51 promoter clone #9 cultured cell line were plated onto a 96-well culture dish, and cultured in 200 µl of RPMI1640/ 10% FBS in the presence of 5% carbon dioxide at 37° C. for 24 hours. Subsequently, a drug for screening was added, culturing was continued for 24 hours, and the luciferase activity was determined. As the drug, synthetic compounds or microbial secondary metabolites were used. 1200 compounds and 9600 microbial secondary metabolites were screened and 71 samples that is capable of activating the p51 promoter activity at a level equal to or greater than that of 0.1 µg/ml trichostatin A. Substances that activate the p51 promoter are expected to become therapeutic agents for treating diseases including cancer.

INDUSTRIAL APPLICABILITY

In accordance with the present invention, there are provided a gene encoding the promoter region of protein p51 which is capable of inducing cell death, and a gene encoding the 5'-untranslated region of p51. They are useful in diagnosing and treating diseases including cancer caused by abnormal regulation of cell propagation. Furthermore, in accordance with the present invention, there are provided the antisense DNAs and the antisense RNAs of these genes, nucleic acid probes comprising parts or all of these genes, methods of detecting the above genes of the present invention or analogous genes using said nucleic acid probes, transformants in which the above gene of the present invention has been introduced, and methods of screening drugs using them. These genes are also useful in diagnosing and treating diseases including cancer, etc.

Sequence Listing Free Text

The base sequences of SEQ ID NO: 5-8, 10 and 11 of the sequence listing show PCR primers.

The base sequence of SEQ ID NO: 9 of the sequence listing shows the 5'-untranslated region of p51A mRNA and encodes 165 bases at the 5'-end of the open reading frame of p51A mRNA.

The base sequences of SEQ ID NO: 12 of the sequence listing shows the DNA sequence of a plasmid containing the p51 promoter and the neomycin-resistant gene.

The invention claimed is:

1. An isolated nucleic acid encoding the p51 promoter region having the base sequence as set forth in SEQ ID NO: 1 of the sequence listing.

2. A recombinant plasmid comprising the nucleic acid of claim 1.

3. An isolated transformant or transductant comprising the recombinant plasmid of claim 2.

* * * * *